US008802681B2

(12) United States Patent
Jenkins et al.

(10) Patent No.: US 8,802,681 B2
(45) Date of Patent: Aug. 12, 2014

(54) PHARMACEUTICAL COMPOSITIONS WITH ATTENUATED RELEASE OF PHENOLIC OPIOIDS

(75) Inventors: Thomas E. Jenkins, Half Moon Bay, CA (US); Julie D. Seroogy, San Carlos, CA (US); Jonathan W. Wray, San Francisco, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 202 days.

(21) Appl. No.: 13/121,335

(22) PCT Filed: Oct. 16, 2009

(86) PCT No.: PCT/US2009/061068
§ 371 (c)(1),
(2), (4) Date: Jun. 9, 2011

(87) PCT Pub. No.: WO2010/045599
PCT Pub. Date: Apr. 22, 2010

(65) Prior Publication Data
US 2011/0281886 A1      Nov. 17, 2011

Related U.S. Application Data

(60) Provisional application No. 61/106,400, filed on Oct. 17, 2008.

(51) Int. Cl.
A61K 31/497        (2006.01)
A61K 31/4965       (2006.01)
A61K 31/44         (2006.01)
A61K 31/485        (2006.01)
A61K 31/155        (2006.01)

(52) U.S. Cl.
CPC ............. *A61K 31/485* (2013.01); *A61K 31/155* (2013.01)
USPC .................. 514/253.02; 514/255.01; 514/282

(58) Field of Classification Search
CPC ........................... A61K 31/155; A61K 31/485
See application file for complete search history.

(56) References Cited

U.S. PATENT DOCUMENTS

| | | | |
|---|---|---|---|
| 4,454,338 A | 6/1984 | Fujii et al. | |
| 4,532,255 A | 7/1985 | Fujii et al. | |
| 5,109,118 A * | 4/1992 | Mizushima | 424/180.1 |
| 5,352,704 A | 10/1994 | Okuyama et al. | |
| 6,388,122 B1 | 5/2002 | Kido et al. | |
| 6,586,196 B1 | 7/2003 | Bronstein et al. | |
| 7,060,290 B1 | 6/2006 | Morimoto et al. | |
| 7,189,414 B2 | 3/2007 | Rubinstein et al. | |
| 7,893,105 B2 | 2/2011 | Xiang et al. | |
| 2003/0180352 A1 | 9/2003 | Patel et al. | |
| 2004/0063628 A1 | 4/2004 | Piccariello et al. | |
| 2005/0176644 A1 | 8/2005 | Mickle et al. | |
| 2007/0082929 A1 | 4/2007 | Gant et al. | |
| 2007/0123468 A1 | 5/2007 | Jenkins et al. | |
| 2007/0203055 A1 | 8/2007 | Mickle et al. | |
| 2009/0136980 A1 | 5/2009 | Bebbington et al. | |
| 2009/0137618 A1 | 5/2009 | Jenkins et al. | |
| 2009/0192093 A1 | 7/2009 | Mickle et al. | |
| 2009/0209569 A1 | 8/2009 | Arnelle et al. | |
| 2010/0035826 A1 | 2/2010 | Jenkins et al. | |
| 2010/0080797 A1 | 4/2010 | Yeomans et al. | |
| 2010/0092562 A1 | 4/2010 | Hollenbeck et al. | |
| 2010/0227921 A1 | 9/2010 | Franklin et al. | |
| 2010/0286186 A1 | 11/2010 | Franklin et al. | |

FOREIGN PATENT DOCUMENTS

| | | |
|---|---|---|
| WO | 2007140272 | 12/2007 |
| WO | WO 2007140272 A2 * | 12/2007 |
| WO | 2008012046 | 1/2008 |
| WO | 2008101187 | 8/2008 |
| WO | 2008101202 | 8/2008 |
| WO | 2009067703 | 5/2009 |
| WO | 2010045599 | 4/2010 |
| WO | 2010100477 | 9/2010 |
| WO | 2011133346 | 4/2011 |

OTHER PUBLICATIONS

Bernkop-Schnurch, The use of inhibitory agents to overcome the enzymatic barrier to perorally administered therapeutic peptides and proteins, Journal of Controlled Release, 1998, vol. 52, pp. 1-16.*
Nafamostat (PubChem, National Center for Biotechnology Information dated Dec. 20, 2005).*
Camostat mesilate (http://www.scbt.com/datasheet-203867-camostat-mesylate.html (downloaded on Nov. 14, 2013)).*
Bernkop-Schnurch "The use of inhibitory agents to overcome the enzymatic barrier to perorally administered therapeutic peptides and proteins" J. Control. Release (1998), vol. 50, No. 1-2, pp. 1-16.
Birk et al., "Trypsin and chymotrypsin inhibitors from soybeans" Methods in Enzymology (1976) vol. 45, pp. 700-707.
Geratz et al., "Novel bis(benzamidine) compounds with an aromatic central link. Inhibitors of thrombin, pancreatic kallikrein, trypsin, and complement" J. Med. Chem. (1976), vol. 19, pp. 634-639.
Göke et al., "Effect of a Specific Serine Protease Inhibitor on the Rat Pancreas: Systemic Administration of Camostate and Exocrine" Digestion (1984) vol. 30, pp. 171-178.
Gomes et al., "Cyclization-activated prodrugs" Molecules, (2007), vol. 12, pp. 2484-2506.
Hijikata et al., "Selective Inhibition of Trypsin by (2R,4R)-4-Phenyl-1-[N!-(7-methoxy-2-naphthalenesulfonyl)-L-arginyl]-2-piperidinecarboxylic Acid" J. Biochem. (2000), vol. 275, pp. 18995-18999.
Kunze et al., "Effects of the serine protease inhibitors FOY and FOY 305 on phospholipase A I (EC 3.1.1.32) activity in rat—liver lysosomes" Pharm. Research Com. (1983), vol. 15, pp. 451-459.

(Continued)

*Primary Examiner* — Michael G Hartley
*Assistant Examiner* — Sun Y Kim
(74) *Attorney, Agent, or Firm* — Carol L. Francis; Bozicevic, Field & Francis LLP

(57) ABSTRACT

Pharmaceutical compositions and their methods of use are provided, where the pharmaceutical compositions comprise a phenolic opioid prodrug that provides enzymatically-controlled release of a phenolic opioid, and an enzyme inhibitor that interacts with the enzyme(s) that mediates the enzymatically-controlled release of the phenolic opioid from the prodrug so as to attenuate enzymatic cleavage of the prodrug.

54 Claims, 5 Drawing Sheets

(56) References Cited

OTHER PUBLICATIONS

Lin et al., "The 0.25-nm X-ray structure of the Bowman-Birk type inhibitor from mung bean in ternary complex with porcine trypsin" Eur. J. Biochem., (1993), vol. 212, pp. 549-555.

Markwardt et al., "Comparative studies on the inhibition of trypsin, plasmin, and thrombin by derivatives of benzylamine and benzylamidine" Eur. J. Biochem, (1968), vol. 6, pp. 502-506.

Ozawa et al., "The reactive site of trypsin inhibitors" J. Biol. Chem. (1966), vol. 241, pp. 3955-3961.

Ramjee et al. "The Kinetic and Structural Characterization of the Reaction of Nafamostat with Bovine Pancreatic Trypsin" Thrmb Res. (2000), vol. 98, No. 6, pp. 559-569.

Renatus et al. "Structural and Functional Analyses of Benzamidine-Based Inhibitors in Complex with Trypsin: Implications for the Inhibition of Factor Xa, tPA, and Urokinase" j. Med. Chem., (1998), vol. 41, No. 27 pp. 5445-5456.

Tanizawa et al. "Inverse Substrates for Tryspin and Tryspin-like Enzymes" Acc. Chem. Res., (1987), vol. 20, pp. 337-343.

Testa et al, "Hydrolysis in Drug and Prodrug Metabolism" Verlag Helvetica Chimica Acta, Postfach, CH-8042, Switzerland (2003) pp. 420-534.

Umezawa et al., "Structure and activities of protease inhibitors of microbial origin" Methods in Enzymology (1976) vol. 45, pp. 678-695.

Tirkkonen et al., "Drug interactions with the potential to prevent prodrug activation as a common source of irrational prescribing in hospital inpatients" Clinical Pharmacology and Therapeutics, (2004) vol. 76, No. 6, pp. 639-647.

Katragadda et al. (2006) "Simultaneous Modulation of Transport and Metabolism of Acyclovir Prodrugs across Rabbit Cornea: An approach Involving Enzyme Inhibitors" Int J Pharm 320(1-2):104-113.

Pauletti et al. (1997) "Esterase-Sensitive Cyclic Prodrugs of Peptides: Evaluation of a Phenylpropionic Acid Promoiety in a Model Hexapeptide" Pharm Res 14(1):11-17.

Song et al. (2002) "Synthesis of a Novel Cyclic Prodrug of RGD Peptidomimetic to Improve Its Cell Membrane Permeation" Bioorg Chem 30(4):285-301.

* cited by examiner

PHARMACEUTICAL COMPOSITIONS WITH ATTENUATED RELEASE OF PHENOLIC OPIOIDS

CROSS-REFERENCE TO RELATED APPLICATION

This application claims priority benefit under 35 U.S.C. §119(e) to U.S. Provisional Patent Application No. 61/106,400, filed on Oct. 17, 2008.

INTRODUCTION

Phenolic opioids are susceptible to abuse. Access to these drugs therefore needs to be to controlled. The control of access to the drugs is expensive to administer and can result in denial of treatment for patients that are not able to present themselves for dosing. For example, patients suffering from acute pain may be denied treatment with an opioid unless they have been admitted to a hospital.

International patent application, publication number WO 2007/140272 describes certain prodrugs that afford controlled release of phenolic opioids. The prodrugs are resistant to abuse, being stable in the presence of household chemicals such as vinegar or baking soda, and require enzyme activation in the gut to initiate release of the phenolic opioid. The prodrugs are believed to release the phenolic opioid through an enzyme-activated cyclisation release mechanism. Thus, enzyme-induced cleavage of an amide bond is believed to afford a nucleophilic nitrogen atom, which then undergoes a cyclisation-release reaction.

The prodrugs described in WO 2007/140272 resist releasing phenolic opioid when subjected to conditions commonly used by those who wish to abuse the drug, but release phenolic opioid when administered orally. This provides substantial protection against abuse. However, there are situations in which oral consumption of such a prodrug could potentially result in overexposure to the phenolic opioid, whether by abuse or accidental over-consumption.

SUMMARY

The present disclosure provides pharmaceutical compositions, and their methods of use, where the pharmaceutical compositions comprise a phenolic opioid prodrug that provides enzymatically-controlled release of a phenolic opioid, and an enzyme inhibitor that interacts with the enzyme(s) that mediates the enzymatically-controlled release of the phenolic opioid from the prodrug so as to attenuate enzymatic cleavage of the prodrug.

According to one aspect, therefore, the embodiments of the invention include pharmaceutical compositions, which comprise a trypsin inhibitor and a compound of general formula (I):

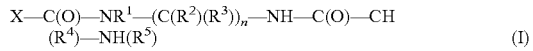  (I)

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ represents a (1-4C)alkyl group;

R$^2$ and R$^3$ each independently represents a hydrogen atom or a (1-4C)alkyl group;

n represents 2 or 3;

R$^4$ represents —CH$_2$CH$_2$CH$_2$NH(C=NH)NH$_2$ or —CH$_2$CH$_2$CH$_2$CH$_2$NH$_2$, the configuration of the carbon atom to which R$^4$ is attached corresponding with that in an L-amino acid; and R$^5$ represents a hydrogen atom, an N-acyl group, or a residue of an amino acid, a dipeptide, or an N-acyl derivative of an amino acid or dipeptide.

The embodiments provide a pharmaceutical composition, which comprises a trypsin inhibitor and a compound of general formula (II):

  (II)

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ is selected from alkyl, substituted alkyl, arylalkyl, substituted arylalkyl, aryl and substituted aryl;

each R$^2$ is independently selected from hydrogen, alkyl, substituted alkyl, aryl, substituted aryl, acyl, and aminoacyl;

each R$^3$ is independently selected from hydrogen, alkyl, substituted alkyl, aryl, substituted aryl, acyl, and aminoacyl;

or R$^2$ and R$^3$ together with the carbon to which they are attached form a cycloalkyl and substituted cycloalkyl group, or two R$^2$ or R$^3$ groups on adjacent carbon atoms, together with the carbon atoms to which they are attached, form a cycloalkyl or substituted cycloalkyl group;

n represents an integer from 2 to 4;

R$^4$ represents —CH$_2$CH$_2$CH$_2$NH(C=NH)NH$_2$ or —CH$_2$CH$_2$CH$_2$CH$_2$NH$_2$, the configuration of the carbon atom to which R$^4$ is attached corresponding with that in an L-amino acid; and R$^5$ represents a hydrogen atom, an N-acyl group (including N-substituted acyl), a residue of an amino acid, a dipeptide, an N-acyl derivative (including N-substituted acyl derivative) of an amino acid or dipeptide.

The embodiments provide a pharmaceutical composition, which comprises a trypsin inhibitor and a compound of general formula (III):

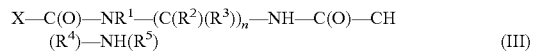  (III)

or pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

R$^1$ represents a (1-4C)alkyl group;

R$^2$ and R$^3$ each independently represents a hydrogen atom or a (1-4C)alkyl group;

n represents 2 or 3;

R$^4$ represents —CH$_2$CH$_2$CH$_2$NH(C=NH)NH$_2$ or —CH$_2$CH$_2$CH$_2$CH$_2$NH$_2$, the configuration of the carbon atom to which R$^4$ is attached corresponding with that in an L-amino acid; and R$^5$ represents a hydrogen atom, an N-acyl group (including N-substituted acyl), a residue of an amino acid, a dipeptide, an N-acyl derivative (including N-substituted acyl derivative) of an amino acid or dipeptide.

The embodiments provide a pharmaceutical composition, which comprises a trypsin inhibitor and a compound of general formula (IV):

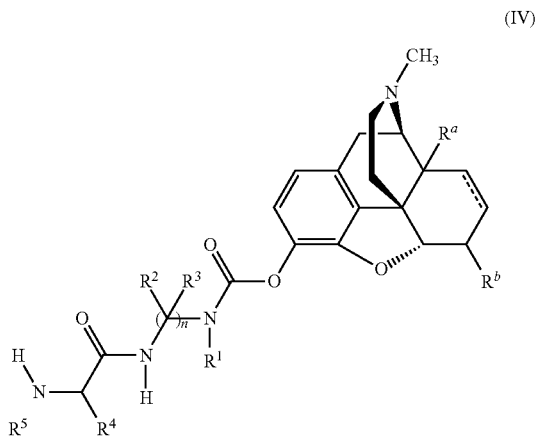

(IV)

or pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group, or a residue of an amino acid, a dipeptide, or an N-acyl derivative of an amino acid or dipeptide.

The embodiments provide a pharmaceutical composition, which comprises a trypsin inhibitor and a compound of general formula (V):

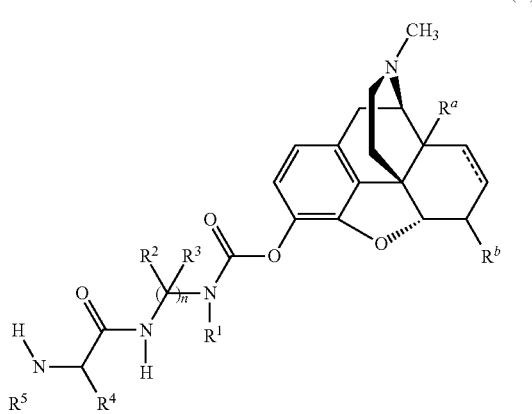

(V)

or pharmaceutically acceptable salt thereof, in which:
$R^a$ is hydrogen or hydroxyl;
$R^b$ is oxo (=O) or hydroxyl;
the dashed line is a double bond or single bond;
$R^1$ is selected from alkyl, substituted alkyl, arylalkyl, substituted arylalkyl, aryl and substituted aryl;
each $R^2$ is independently selected from hydrogen, alkyl, substituted alkyl, aryl, substituted aryl, acyl, and aminoacyl;
each $R^3$ is independently selected from hydrogen, alkyl, substituted alkyl, aryl, substituted aryl, acyl, and aminoacyl;
or $R^2$ and $R^3$ together with the carbon to which they are attached form a cycloalkyl and substituted cycloalkyl group, or two $R^2$ or $R^3$ groups on adjacent carbon atoms, together with the carbon atoms to which they are attached, form a cycloalkyl or substituted cycloalkyl group;
n represents an integer from 2 to 4;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group (including N-substituted acyl), a residue of an amino acid, a dipeptide, an N-acyl derivative (including N-substituted acyl derivative) of an amino acid or dipeptide.

The embodiments provide a pharmaceutical composition, which comprises a trypsin inhibitor and a compound of general formula (VI):

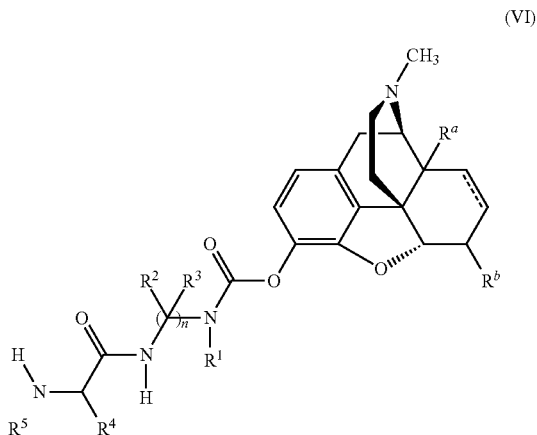

(VI)

or pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group (including N-substituted acyl), a residue of an amino acid, a dipeptide, an N-acyl derivative (including N-substituted acyl to derivative) of an amino acid or dipeptide.

BRIEF DESCRIPTION OF THE FIGURES

FIG. 7A depicts the disappearance of Compound 4, and FIG. 7B depicts the appearance of hydromorphone, over time under these conditions.

DEFINITIONS

Figure 1:
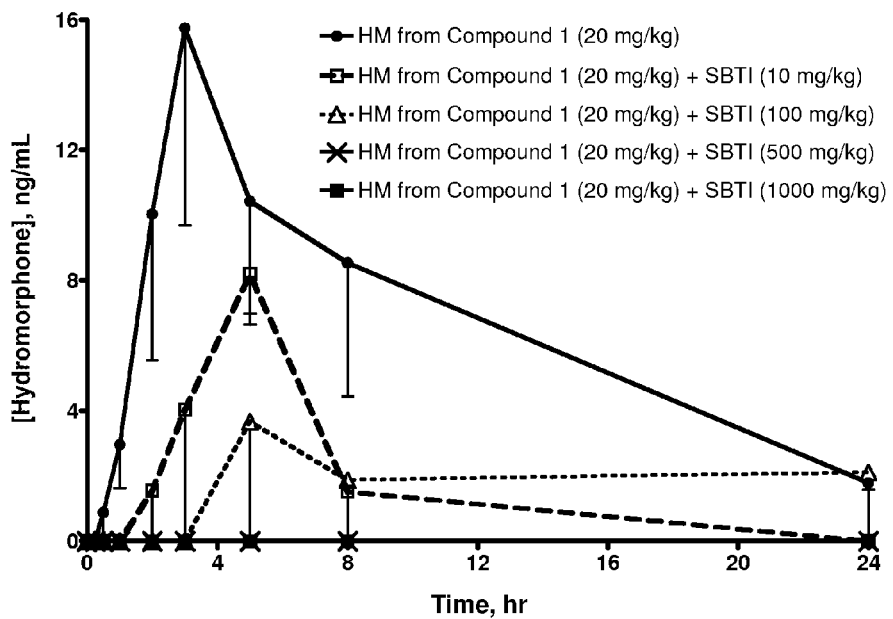
FIG. 1 is a graph that compares mean blood concentrations over time of hydromorphone (HM) following PO administration to rats of Compound 1 alone and Compound 1 with various amounts of trypsin inhibitor from *Glycine max* (soybean) (SBTI).

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl, piperonyl, and the like. Substituted acyl refers to substituted versions of acyl and include, for example, but not limited to, succinyl and malonyl.

The term "aminoacyl" and "amide" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms. In other embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenyleth-1-yl, naphthylmethyl, 2-naphthyleth-1-yl, naphthobenzyl, 2-naphthophenyleth-1-yl and the like. In some embodiments, an arylalkyl group is ($C_7$-$C_{30}$) arylalkyl, e.g., the alkyl moiety of the arylalkyl group is ($C_1$-$C_{10}$) and the aryl moiety is ($C_6$-$C_{20}$). In other embodiments, an arylalkyl group is ($C_7$-$C_{20}$) arylalkyl, e.g., the alkyl moiety of the arylalkyl group is ($C_1$-$C_8$) and the aryl moiety is ($C_6$-$C_{12}$).

Compounds may be identified either by their chemical structure and/or chemical name. The compounds described herein may contain one or more chiral centers and/or double bonds and therefore, may exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. Certain compounds may exist in multiple crystalline or amorphous forms. In general, all physical forms are equivalent for the uses contemplated herein and are intended to be within the scope of the present disclosure.

"Cycloalkyl" by itself or as part of another substituent refers to a saturated cyclic alkyl radical. Typical cycloalkyl groups include, but are not limited to, groups derived from cyclopropane, cyclobutane, cyclopentane, cyclohexane and the like. In some embodiments, the cycloalkyl group is ($C_3$-$C_{10}$) cycloalkyl. In other embodiments, the cycloalkyl group is ($C_3$-$C_7$) cycloalkyl.

"Cycloheteroalkyl" by itself or as part of another substituent, refers to a saturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkenyl and Heteroalkynyl" by themselves or as part of another substituent refer to alkyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5-20 membered heteroaryl. In other embodiments, the heteroaryl group is from 5-10 membered heteroaryl. In still other embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. In some embodiments, the heteroarylalkyl group is a 6-30 membered heteroarylalkyl, e.g., the alkyl moiety of the heteroarylalkyl is 1-10 membered and the heteroaryl moiety is a 5-20-membered heteroaryl. In other embodiments, the heteroarylalkyl group is 6-20 membered heteroarylalkyl, e.g., the alkyl moiety of the heteroarylalkyl is 1-8 membered and the heteroaryl moiety is a 5-12-membered heteroaryl.

"Opioid" refers to a chemical substance that exerts its pharmacological action by interaction at opioid receptors. "Phenolic opioid" refers to a subset of the opioids that contains a phenol group. Examples of phenolic opioids are provided below.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutical composition" refers to at least one compound and a pharmaceutically acceptable vehicle, with which the compound is administered to a patient.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, i.e. a compound of the embodiments or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable vehicle" refers to a diluent, adjuvant, excipient or carrier with, or in which a compound is administered.

"Patient" includes humans, and also other mammals, such as livestock, zoo animals and companion animals, such as a cat, dog or horse.

"Preventing" or "prevention" or "prophylaxis" refers to a reduction in risk of occurrence of a condition, such as pain.

"Prodrug" refers to a derivative of an active agent that requires a transformation within the body to release the active agent. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, alkylenedioxy (such as methylenedioxy), -M, $—R^{60}$, $—O^-$, $=O$, $—OR^{60}$, $—SR^{60}$, $—S^-$, $=S$, $—NR^{60}R^{61}$, $=NR^{60}$, $—CF_3$, CN, $—OCN$, $—SCN$, $—NO$, $—NO_2$, $=N_2$, $—N_3$, $—S(O)_2O^-$, $—S(O)_2OH$, $—S(O)_2R^{60}$, $—OS(O)_2O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $—NR^{62}C(NR^{63})NR^{60}R^{61}$ and $—C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound that, when to administered to a patient for preventing or treating a condition such as pain, is sufficient to effect such treatment. The "therapeutically effective amount" will vary depending on the compound, the condition and its severity and the age, weight, etc., of the patient.

Detailed Description

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as to described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

It has now been found that attenuated release of a phenolic opioid can be achieved by administering a trypsin inhibitor derived from soybean in combination with a particular prodrug described in WO 2007/140272.

Representative Embodiments

The present disclosure provides pharmaceutical compositions, and their methods of use, where the pharmaceutical compositions comprise a phenolic opioid prodrug that provides enzymatically-controlled release of a phenolic opioid, and an enzyme inhibitor that interacts with the enzyme(s) that mediates the enzymatically-controlled release of the phenolic opioid from the prodrug so as to attenuate enzymatic cleavage of the prodrug. The disclosure provides pharmaceutical compositions which comprise a trypsin inhibitor and a phenolic opioid prodrug that contains a trypsin-labile moiety that, when cleaved, facilitates release of phenolic opioid. Examples of phenolic opioid prodrugs and trypsin inhibitors are described below.

Phenolic Opioid Prodrugs

According to certain embodiments, there is provided a phenolic opioid prodrug which provides enzymatically-controlled release of a phenolic opioid. The phenolic opioid prodrug is a corresponding compound in which the phenolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a phenolic opioid.

The enzyme capable of cleaving the enzymatically-cleavable moiety may be a peptidase—the enzymatically-cleavable moiety being linked to the nucleophilic nitrogen through an amide (e.g. a peptide: —NHCO—) bond. In some embodiments, the enzyme is a digestive enzyme of a protein.

Formulae I-VI

As shown herein, Formula I describes compounds of Formula II, in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

Formula III describes compounds of Formula II, in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

Formula IV describes compounds of Formula I, wherein "X" is replaced structurally with certain phenolic opioids.

As also shown herein, Formula IV describes compounds of Formula V, in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

Formula VI describes compounds of Formula V, in which $R^1$ is (1-4C)alkyl group; $R^2$ and $R^3$ each independently represents a hydrogen atom or a (1-4C)alkyl group; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

For Formulae I-III, X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$).

As disclosed above, "opioid" refers to a chemical substance that exerts its pharmacological action by interaction at opioid receptors. "Phenolic opioid" refers to a subset of the opioids that contain a phenol group. For example, phenolic opioids include, but are not limited to, buprenorphine, dihydroetorphine, diprenorphine, etorphine, hydromorphone, levorphanol, morphine (and metabolites thereof), nalmefene, naloxone, N-methylnaloxone, naltrexone, N-methylnaltrexone, oxymorphone, oripavin, ketobemidone, to dezocine, pentazocine, phenazocine, butorphanol, nalbuphine, meptazinol, O-desmethyltramadol, tapentado, nalorphine. The structures of the aforementioned phenolic opioids are shown below:

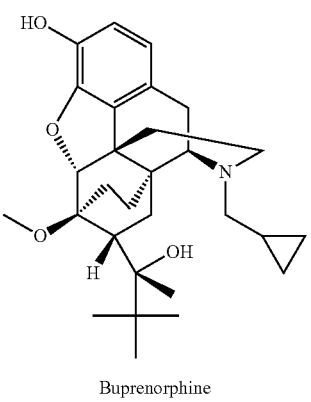

Buprenorphine

-continued
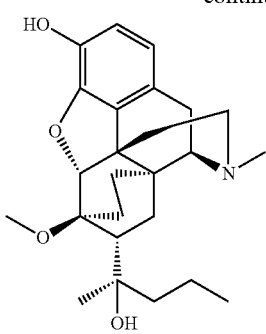
Dihydroetorphine
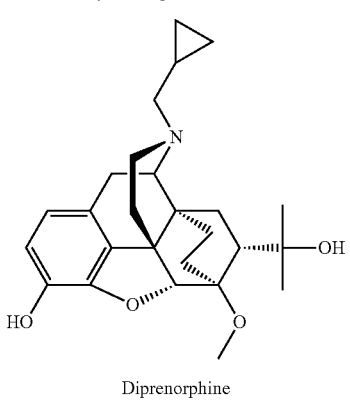
Diprenorphine
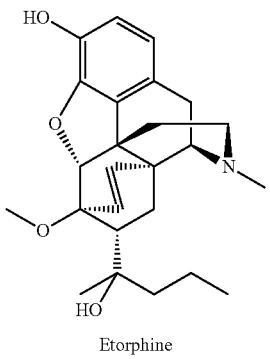
Etorphine
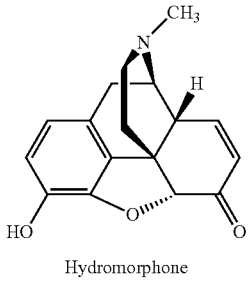
Hydromorphone
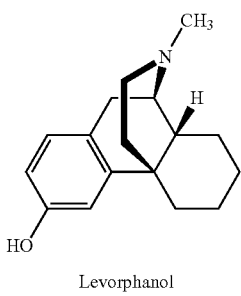
Levorphanol
-continued
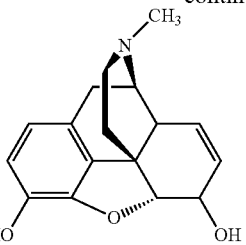
Morphine
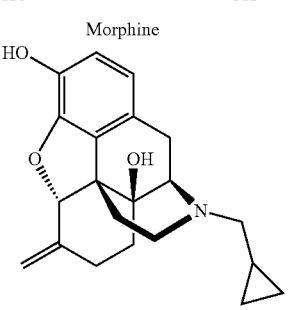
Nalmefene
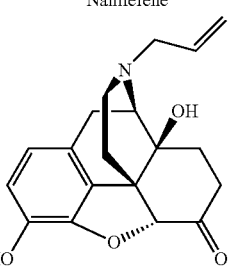
Naloxone
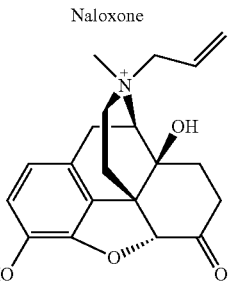
N-Methylnaloxone
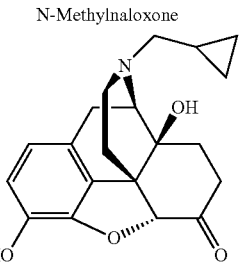
Naltrexone
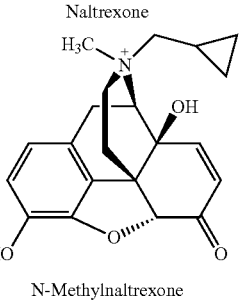
N-Methylnaltrexone

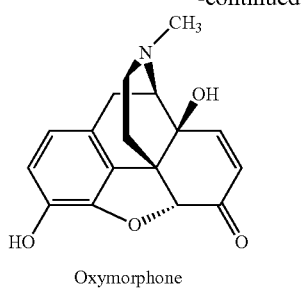
Oxymorphone
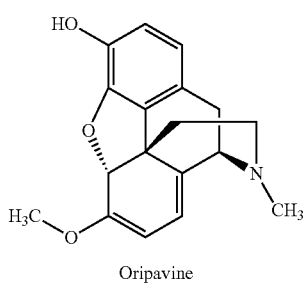
Oripavine
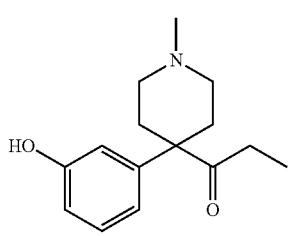
Ketobemidone
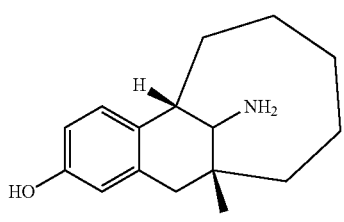
Dezocine
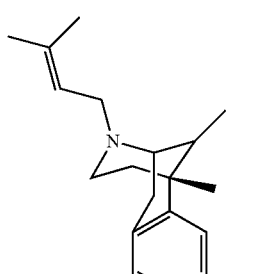
Pentazocine
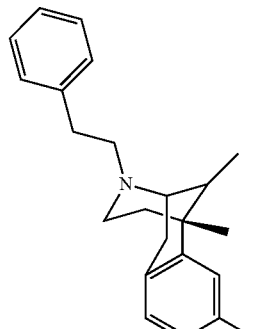
Phenazocine
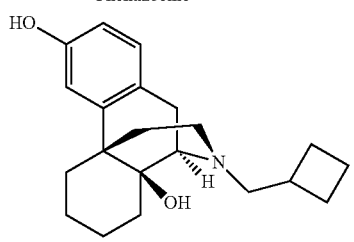
Butorphanol
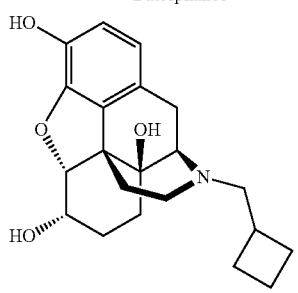
Nalbuphine
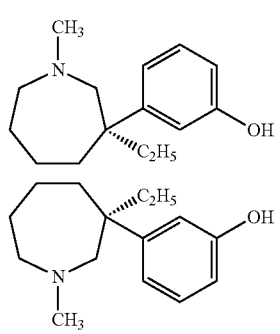
Meptazinol
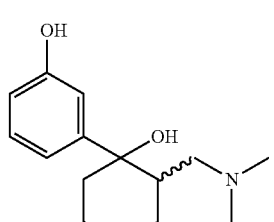
o-Desmethyltramadol

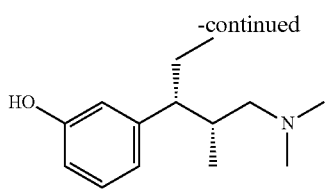

Tapentadol

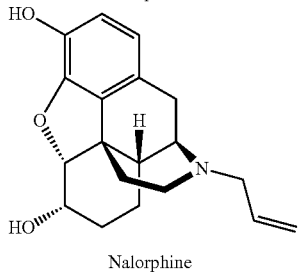

Nalorphine

In certain embodiments, the phenolic opioid is oxymorphone, hydromorphone, or morphine.

Formulae I-VI are now described in more detail below.

Formula I

The compounds of formula (I) correspond with compounds disclosed in WO 2007/140272 in which the nucleophilic nitrogen atom is bound to a residue of L-arginine or L-lysine.

Examples of values for the phenolic opioid as provided in X are oxymorphone, hydromorphone and morphine.

Examples of values for $R^1$ are methyl and ethyl groups.

Examples of values for each of $R^2$ and $R^3$ are hydrogen atoms.

An example of a value for n is 2.

In one embodiment, $R^4$ represents —$CH_2CH_2CH_2NH$ (C=NH)$NH_2$.

An amino acid can be a naturally occurring amino acid. It will be appreciated that naturally occurring amino acids usually have the L-configuration.

Referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In one embodiment, $R^5$ represents N-acetyl, glycinyl or N-acetylglycinyl, such as N-acetyl.

An example of the group represented by —C(O)—CH($R^4$)—NH($R^5$) is N-acetylarginyl.

In a particular embodiment, the compound of formula (I) is hydromorphone 3-(N-methyl-N-(2-N'-acetylarginylamino)) ethylcarbamate, or a pharmaceutically acceptable salt thereof. This compound is described in Example 3 of WO 2007/140272.

Formula II

The embodiments provide a compound of general formula (II):

$$X—C(O)—NR^1—(C(R^2)(R^3))_n—NH—C(O)—CH(R^4)—NH(R^5) \quad (II)$$

or a pharmaceutically acceptable salt thereof, in which:

X represents a residue of a phenolic opioid, wherein the hydrogen atom of the phenolic hydroxyl group is replaced by a covalent bond to —C(O)—NR$^1$—(C(R$^2$)(R$^3$))$_n$—NH—C(O)—CH(R$^4$)—NH(R$^5$);

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl and substituted cycloalkyl group, or two $R^2$ or $R^3$ groups on adjacent carbon atoms, together with the carbon atoms to which they are attached, form a cycloalkyl or substituted cycloalkyl group;

n represents an integer from 2 to 4;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

In formula II, examples of values for the phenolic opioid as provided in X are oxymorphone, hydromorphone and morphine.

In formula II, $R^1$ can be selected from alkyl, substituted alkyl, arylalkyl, substituted arylalkyl, aryl and substituted aryl. In certain instances, $R^1$ is (1-6C)alkyl. In other instances, $R^1$ is (1-4C)alkyl. In other instances, $R^1$ is methyl or ethyl. In other instances, $R^1$ is methyl. In some instances, $R^1$ is ethyl.

In certain instances, $R^1$ is substituted alkyl. In certain instances, $R^1$ is an alkyl group substituted with carboxyl or carboxyl ester. In certain instances, $R^1$ is —$(CH_2)_5$—COOH, —$(CH_2)_5$—COOCH$_3$, or —$(CH_2)_5$—COOCH$_2$CH$_3$.

In certain instances, in formula II, $R^1$ is arylalkyl or substituted arylalkyl. In certain instances, in formula II, $R^1$ is arylalkyl. In certain instances, $R^1$ is substituted arylalkyl. In certain instances, $R^1$ is an arylalkyl group substituted with carboxyl or carboxyl ester. In certain instances, $R^1$ is —$(CH_2)_q(C_6H_4)$—COOH, —$(CH_2)_q(C_6H_4)$—COOCH$_3$, or —$(CH_2)_q(C_6H_4)$—COOCH$_2$CH$_3$, where q is an integer from one to 10. In certain instances, $R^1$ is —$CH_2(C_6H_4)$—COOH, —$CH_2(C_6H_4)$—COOCH$_3$, or —$CH_2(C_6H_4)$—COOCH$_2$CH$_3$.

In certain instances, in formula II, $R^1$ is aryl. In certain instances, $R^1$ is substituted aryl. In certain instances, $R^1$ is an aryl group substituted with carboxyl or carboxyl ester. In certain instances, $R^1$ is —$(C_6H_4)$—COOH, —$(C_6H_4)$—COOCH$_3$, or —$(C_6H_4)$—COOCH$_2$CH$_3$.

In formula II, each $R^2$ can be independently selected from hydrogen, alkyl, substituted alkyl, aryl, substituted aryl, acyl, and aminoacyl. In certain instances, $R^2$ is hydrogen or alkyl.

In certain instances, $R^2$ is hydrogen. In certain instances, $R^1$ is alkyl. In certain instances, $R^2$ is acyl. In certain instances, $R^2$ is aminoacyl.

In formula II, each $R^3$ can be independently selected from hydrogen, alkyl, substituted alkyl, aryl, substituted aryl, acyl, and aminoacyl. In certain instances, $R^3$ is hydrogen or alkyl. In certain instances, $R^3$ is hydrogen. In certain instances, $R^3$ is alkyl. In certain instances, $R^3$ is acyl. In certain instances, $R^3$ is aminoacyl.

In certain instances, $R^2$ and $R^3$ are hydrogen. In certain instances, $R^2$ and $R^3$ on the same carbon are both alkyl. In certain instances, $R^2$ and $R^3$ on the same carbon are methyl. In certain instances, $R^2$ and $R^3$ on the same carbon are ethyl.

In formula II, $R^2$ and $R^3$ together with the carbon to which they are attached can form a cycloalkyl and substituted cycloalkyl group, or two $R^2$ or $R^3$ groups on adjacent carbon atoms, together with the carbon atoms to which they are attached, can form a cycloalkyl or substituted cycloalkyl group. In certain instances, $R^2$ and $R^3$ together with the carbon to which they are attached can form a cycloalkyl group. Thus, in certain instances, $R^2$ and $R^3$ on the same carbon form a spirocycle. In certain instances, $R^2$ and $R^3$ together with the carbon to which they are attached can form a substituted cycloalkyl group. In certain instances, two $R^2$ or $R^3$ groups on adjacent carbon atoms, together with the carbon atoms to which they are attached, can form a cycloalkyl group. In certain instances, two $R^2$ or $R^3$ groups on adjacent carbon atoms, together with the carbon atoms to which they are attached, can form a substituted cycloalkyl group.

In certain instances, one of $R^2$ and $R^3$ is aminoacyl.

In certain instances, one of $R^2$ and $R^3$ is aminoacyl comprising phenylenediamine. In certain instances, one of $R^2$ and $R^3$ is

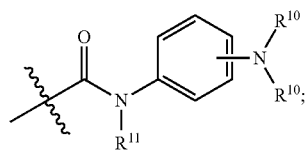

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^2$ and $R^3$ is

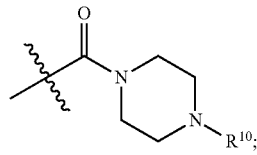

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, $R^2$ or $R^3$ can modulate a rate of intramolecular cyclization. $R^2$ or $R^3$ can speed up a rate of intramolecular cyclization, when compared to the corresponding molecule where $R^2$ and $R^3$ are both hydrogen. In certain instances, $R^2$ or $R^3$ comprise an electron-withdrawing group or an electron-donating group. In certain instances, $R^2$ or $R^3$ comprise an electron-withdrawing group. In certain instances, $R^2$ or $R^3$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $-[C(R^2)(R^3)]_n-$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(F)CH_2-$; $-CH_2C(F_2)CH_2-$; $-CH_2CH(C(O)NR^{20}R^{21})-$; $-CH_2CH(C(O)OR^{22})-$; $-CH_2CH(C(O)OH)-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; $-CH_2CH_2CH(CH_2F)-$; $-CH_2CH_2CH(C(O)NR^{23}R^{24})-$; $-CH_2CH_2CH(C(O)OR^{25})-$; and $-CH_2CH_2CH(C(O)OH)-$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula II, n represents an integer from 2 to 4. An example of a value for n is 2. An example of a value for n is 3. An example of a value for n is 4.

In formula II, in one embodiment, $R^4$ represents $-CH_2CH_2CH_2NH(C=NH)NH_2$. In another embodiment, $R^4$ represents $-CH_2CH_2CH_2CH_2NH_2$.

An amino acid can be a naturally occurring amino acid. It will be appreciated that naturally occurring amino acids usually have the L-configuration.

In formula II, referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In formula II, examples of particular values for $R^5$ are:
a hydrogen atom;
for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula II, in one embodiment, $R^5$ represents N-acetyl, glycinyl or N-acetylglycinyl, such as N-acetyl.

In formula II, an example of the group represented by —C(O)—CH($R^4$)—NH($R^5$) is N-acetylarginyl or N-acetyllysinyl.

In formula II, in certain instances, $R^5$ represents substituted acyl. In certain instances, $R^5$ can be malonyl or succinyl.

In formula II, in certain instances, the group represented by —C(O)—CH($R^4$)—NH($R^5$) is N-malonylarginyl, N-malonyllysinyl, N-succinylarginyl and N-succinyllysinyl.

Formula III

The embodiments provide a compound of general formula (III):

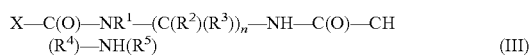

(III)

or a pharmaceutically acceptable salt thereof, in which:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, an N-acyl derivative (including N-substituted acyl derivative) of an amino acid or dipeptide.

In formula III, examples of values for the phenolic opioid as provided in X are oxymorphone, hydromorphone and morphine.

In formula III, examples of values for $R^1$ are methyl and ethyl groups.

In formula III, examples of values for each of $R^2$ and $R^3$ are hydrogen atoms.

In formula III, an example of a value for n is 2.

In formula III, in one embodiment, $R^4$ represents —$CH_2CH_2CH_2NH(C=NH)NH_2$. In another embodiment, $R^4$ represents —$CH_2CH_2CH_2CH_2NH_2$.

An amino acid can be a naturally occurring amino acid. It will be appreciated that naturally occurring amino acids usually have the L-configuration.

In formula III, referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In formula III, examples of particular values for $R^5$ are: a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula III, in one embodiment, $R^5$ represents N-acetyl, glycinyl or N-acetylglycinyl, such as N-acetyl.

In formula III, an example of the group represented by —C(O)—CH($R^4$)—NH($R^5$) is N-acetylarginyl or N-acetyllysinyl.

In formula III, in certain instances, $R^5$ represents substituted acyl. In certain instances, $R^5$ can be malonyl or succinyl.

In formula III, in certain instances, the group represented by —C(O)—CH($R^4$)—NH($R^5$) is N-malonylarginyl, N-malonyllysinyl, N-succinylarginyl and N-succinyllysinyl.

Formula IV

The embodiments provide a compound of general formula (IV):

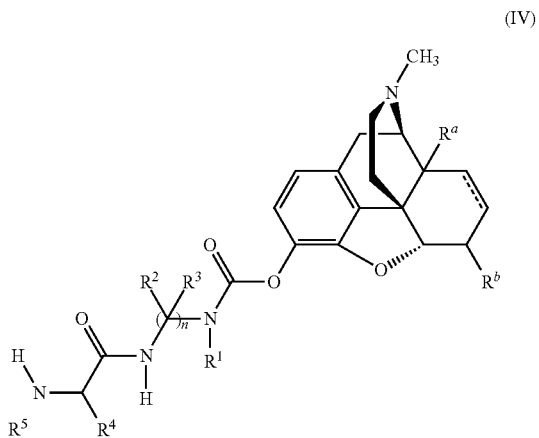

(IV)

or a pharmaceutically acceptable salt thereof, in which:

$R^a$ is hydrogen or hydroxyl;

$R^b$ is oxo (=O) or hydroxyl;

the dashed line is a double bond or single bond;

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

In formula IV, a certain example of $R^a$ is hydrogen. In formula IV, a certain example of $R^a$ is hydroxyl.

In formula IV, a certain example of $R^b$ is oxo (=O). In formula IV, a certain example of $R^b$ is hydroxyl;

In formula IV, a certain example of the dashed line is a double bond. In formula IV, a certain example of the dashed line is a single bond.

In formula IV, examples of values for $R^1$ are methyl and ethyl groups.

In formula IV, examples of values for each of $R^2$ and $R^3$ are hydrogen atoms.

In formula IV, an example of a value for n is 2.

In formula IV, in one embodiment, R⁴ represents —CH₂CH₂CH₂NH(C═NH)NH₂.

An amino acid can be a naturally occurring amino acid. It will be appreciated that naturally occurring amino acids usually have the L-configuration.

In formula IV, referring to R⁵, examples of particular values are:

a hydrogen atom;
for an N-acyl group: an N-(1-4C)alkanoyl group, such as acetyl, an N-aroyl group, such as N-benzoyl, or an N-piperonyl group;
for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and
for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In formula IV, examples of particular values for R⁵ are:
a hydrogen atom;
for an N-acyl group: an N-(1-4C)alkanoyl group, such as acetyl, an N-aroyl group, such as N-benzoyl, or an N-piperonyl group; and
for a residue of an amino acid, a dipeptide, or an N-acyl derivative of an amino acid or dipeptide: glycinyl or N-acetylglycinyl.

In formula IV, in one embodiment, R⁵ represents N-acetyl, glycinyl or N-acetylglycinyl, such as N-acetyl.

In formula IV, an example of the group represented by —C(O)—CH(R⁴)—NH(R⁵) is N-acetylarginyl.

Formula V

The embodiments provide a compound of general formula (V):

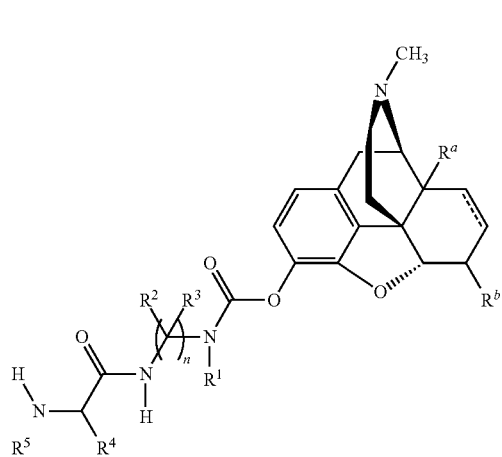

or a pharmaceutically acceptable salt thereof, in which:
R$^a$ is hydrogen or hydroxyl;
R$^b$ is oxo (═O) or hydroxyl;
the dashed line is a double bond or single bond;
R¹ is selected from alkyl, substituted alkyl, arylalkyl, substituted arylalkyl, aryl and to substituted aryl;
each R² is independently selected from hydrogen, alkyl, substituted alkyl, aryl, substituted aryl, acyl, and aminoacyl;
each R³ is independently selected from hydrogen, alkyl, substituted alkyl, aryl, substituted aryl, acyl, and aminoacyl;

or R² and R³ together with the carbon to which they are attached form a cycloalkyl and substituted cycloalkyl group, or two R² or R³ groups on adjacent carbon atoms, together with the carbon atoms to which they are attached, form a cycloalkyl or substituted cycloalkyl group;

n represents an integer from 2 to 4;
R⁴ represents —CH₂CH₂CH₂NH(C═NH)NH₂ or —CH₂CH₂CH₂CH₂NH₂, the configuration of the carbon atom to which R⁴ is attached corresponding with that in an L-amino acid; and
R⁵ represents a hydrogen atom, an N-acyl group (including N-substituted acyl), a residue of an amino acid, a dipeptide, an N-acyl derivative (including N-substituted acyl derivative) of an amino acid or dipeptide.

In formula V, a certain example of R$^a$ is hydrogen. In formula IV, a certain example of R$^a$ is hydroxyl.

In formula V, a certain example of R$^b$ is oxo (═O). In formula V, a certain example of R$^b$ is hydroxyl;

In formula V, a certain example of the dashed line is a double bond. In formula V, a certain example of the dashed line is a single bond.

In formula V, R¹ can be selected from alkyl, substituted alkyl, arylalkyl, substituted arylalkyl, aryl and substituted aryl. In certain instances, R¹ is (1-6C)alkyl. In other instances, R¹ is (1-4C)alkyl. In other instances, R¹ is methyl or ethyl. In other instances, R¹ is methyl. In some instances, R¹ is ethyl.

In certain instances, R¹ is substituted alkyl. In certain instances, R¹ is an alkyl group substituted with carboxyl or carboxyl ester. In certain instances, R¹ is —(CH₂)₅—COOH, —(CH₂)₅—COOCH₃, or —(CH₂)₅—COOCH₂CH₃.

In certain instances, in formula V, R¹ is arylalkyl or substituted arylalkyl. In certain instances, in formula V, R¹ is arylalkyl. In certain instances, R¹ is substituted arylalkyl. In certain instances, R¹ is an arylalkyl group substituted with carboxyl or carboxyl ester. In certain instances, R¹ is —(CH₂)$_q$(C₆H₄)—COOH, —(CH₂)$_q$(C₆H₄)—COOCH₃, or —(CH₂)$_q$(C₆H₄)—COOCH₂CH₃, where q is an integer from one to 10. In certain instances, R¹ is —CH₂(C₆H₄)—COOH, —CH₂(C₆H₄)—COOCH₃, or —CH₂(C₆H₄)—COOCH₂CH₃.

In certain instances, in formula V, R¹ is aryl. In certain instances, R¹ is substituted aryl. In certain instances, R¹ is an aryl group substituted with carboxyl or carboxyl ester. In certain instances, R¹ is —(C₆H₄)—COOH, —(C₆H₄)—COOCH₃, or —(C₆H₄)—COOCH₂CH₃.

In formula V, each R² can be independently selected from hydrogen, alkyl, substituted alkyl, aryl, substituted aryl, acyl, and aminoacyl. In certain instances, R² is hydrogen or alkyl. In certain instances, R² is hydrogen. In certain instances, R¹ is alkyl. In certain instances, R² is acyl. In certain instances, R² is aminoacyl.

In formula V, each R³ can be independently selected from hydrogen, alkyl, substituted alkyl, aryl, substituted aryl, acyl, and aminoacyl. In certain instances, R³ is hydrogen or alkyl. In certain instances, R³ is hydrogen. In certain instances, R³ is alkyl. In certain instances, R³ is acyl. In certain instances, R³ is aminoacyl.

In certain instances, R² and R³ are hydrogen. In certain instances, R² and R³ on the same carbon are both alkyl. In certain instances, R² and R³ on the same carbon are methyl. In certain instances, R² and R³ on the same carbon are ethyl.

In formula V, R² and R³ together with the carbon to which they are attached can form a cycloalkyl and substituted cycloalkyl group, or two R² or R³ groups on adjacent carbon atoms, together with the carbon atoms to which they are attached, can form a cycloalkyl or substituted cycloalkyl group. In certain instances, $R^2$ and $R^3$ together with the carbon to which they are attached can form a cycloalkyl group. Thus, in certain instances, $R^2$ and $R^3$ on the same carbon form a spirocycle. In certain instances, $R^2$ and $R^3$ together with the carbon to which they are attached can form a substituted cycloalkyl group. In certain instances, two $R^2$ or $R^3$ groups on adjacent carbon atoms, together with the carbon atoms to which they are attached, can form a cycloalkyl group. In certain instances, two $R^2$ or $R^3$ groups on adjacent to carbon atoms, together with the carbon atoms to which they are attached, can form a substituted cycloalkyl group.

In certain instances, one of $R^2$ and $R^3$ is aminoacyl.

In certain instances, one of $R^2$ and $R^3$ is aminoacyl comprising phenylenediamine. In certain instances, one of $R^2$ and $R^3$ is

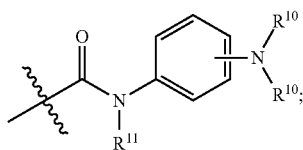

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^2$ and $R^3$ is

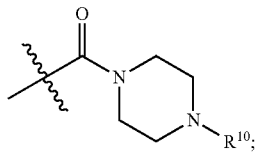

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, $R^2$ or $R^3$ can modulate a rate of intramolecular cyclization. $R^2$ or $R^3$ can speed up a rate of intramolecular cyclization, when compared to the corresponding molecule where $R^2$ and $R^3$ are both hydrogen. In certain instances, $R^2$ or $R^3$ comprise an electron-withdrawing group or an electron-donating group. In certain instances, $R^2$ or $R^3$ comprise an electron-withdrawing group. In certain instances, $R^2$ or $R^3$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $-[C(R^2)(R^3)]_n-$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(F)CH_2-$; $-CH_2C(F_2)CH_2-$; $-CH_2CH(C(O)NR^{20}R^{21})-$; $-CH_2CH(C(O)OR^{22})-$; $-CH_2CH(C(O)OH)-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; $-CH_2CH_2CH(CH_2F)-$; $-CH_2CH_2CH(C(O)NR^{23}R^{24})-$; $-CH_2CH_2CH(C(O)OR^{25})-$; and $-CH_2CH_2CH(C(O)OH)-$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula V, n represents an integer from 2 to 4. An example of a value for n is 2. An example of a value for n is 3. An example of a value for n is 4.

In formula V, in one embodiment, $R^4$ represents $-CH_2CH_2CH_2NH(C=NH)NH_2$. In another embodiment, $R^4$ represents $-CH_2CH_2CH_2CH_2NH_2$.

An amino acid can be a naturally occurring amino acid. It will be appreciated that naturally occurring amino acids usually have the L-configuration.

In formula V, referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In formula V, examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula V, in one embodiment, $R^5$ represents N-acetyl, glycinyl or N-acetylglycinyl, such as N-acetyl.

In formula V, an example of the group represented by $-C(O)-CH(R^4)-NH(R^5)$ is N-acetylarginyl or N-acetyllysinyl.

In formula V, in certain instances, $R^5$ represents substituted acyl. In certain instances, $R^5$ can be malonyl or succinyl.

In formula V, in certain instances, the group represented by $-C(O)-CH(R^4)-NH(R^5)$ is N-malonylarginyl, N-malonyllysinyl, N-succinylarginyl and N-succinyllysinyl.

Formula VI

The embodiments provide a compound of general formula (VI):

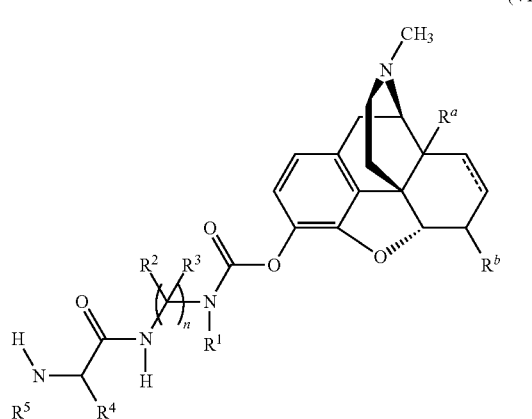

(VI)

or a pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group (including N-substituted acyl), a residue of an amino acid, a dipeptide, an N-acyl derivative (including N-substituted acyl derivative) of an amino acid or dipeptide.

In formula VI, a certain example of $R^a$ is hydrogen. In formula VI, a certain example of $R^a$ is hydroxyl.

In formula VI, a certain example of $R^b$ is oxo (=O). In formula VI, a certain example of $R^b$ is hydroxyl;

In formula VI, a certain example of the dashed line is a double bond. In formula VI, a certain example of the dashed line is a single bond.

In formula VI, examples of values for $R^1$ are methyl and ethyl groups.

In formula VI, examples of values for each of $R^2$ and $R^3$ are hydrogen atoms.

In formula VI, an example of a value for n is 2.

In formula VI, in one embodiment, $R^4$ represents —$CH_2CH_2CH_2NH(C=NH)NH_2$. In another embodiment, $R^4$ represents —$CH_2CH_2CH_2CH_2NH_2$.

An amino acid can be a naturally occurring amino acid. It will be appreciated that naturally occurring amino acids usually have the L-configuration.

In formula VI, referring to $R^5$, examples of particular values are:
for an N-acyl group: an N-(1-4C)alkanoyl group, such as acetyl, an N-aroyl group, such as N-benzoyl, or an N-piperonyl group;
for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and
for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In formula VI, examples of particular values for $R^5$ are:
a hydrogen atom;
for an N-acyl group: an N-(1-4C)alkanoyl group, such as acetyl, an N-aroyl group, such as N-benzoyl, or an N-piperonyl group; and
for a residue of an amino acid, a dipeptide, or an N-acyl derivative of an amino acid or dipeptide: glycinyl or N-acetylglycinyl.

In formula VI, in one embodiment, $R^5$ represents N-acetyl, glycinyl or N-acetylglycinyl, such as N-acetyl.

In formula VI, an example of the group represented by —C(O)—CH($R^4$)—NH($R^5$) is N-acetylarginyl or N-acetyllysinyl.

In formula VI, in certain instances, $R^5$ represents substituted acyl. In certain instances, $R^5$ can be malonyl or succinyl.

In formula VI, in certain instances, the group represented by —C(O)—CH($R^4$)—NH($R^5$) is N-malonylarginyl, N-malonyllysinyl, N-succinylarginyl and N-succinyllysinyl.

General Synthetic Procedures

Compounds of formula I are particular prodrugs described in WO 2007/140272 and the synthesis of compounds of formula I are described therein.

The synthetic schemes and procedure in WO 2007/140272 can also be used to synthesize compounds of formulae I-VI. The compounds described herein may be obtained via the routes generically illustrated in Scheme 1.

The promoieties described herein, may be prepared and attached to drugs containing phenols by procedures known to those of skill in the art (See e.g., Green et al., "Protective Groups in Organic Chemistry," (Wiley, $2^{nd}$ ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, (Wiley Interscience); Trost et al., "Comprehensive Organic Synthesis," (Pergamon Press, 1991); "Theilheimer's Synthetic Methods of Organic Chemistry," Volumes 1-45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well established synthetic procedures, supra.

Scheme 1

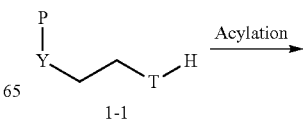

1-1

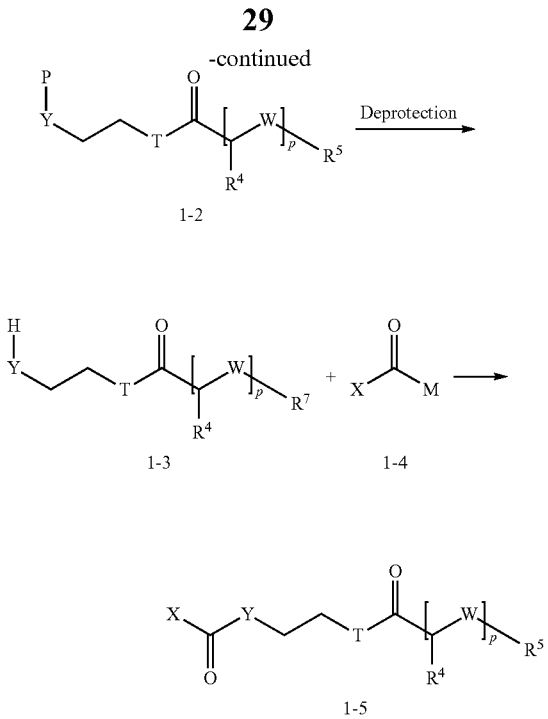

Referring now to Scheme 1 and formula I, supra, where for illustrative purposes T is NH, Y is $NR^1$, W is NH, p is one, $R^1$, $R^4$, and $R^5$ are as previously defined, X is a phenolic opioid, P is a protecting group, and M is a leaving group, compound 1-1 may be acylated with an appropriate carboxylic acid or carboxylic acid equivalent to provide compound 1-2 which then may be deprotected to yield compound 1-3. Compound 1-3 is then reacted with an activated carbonic acid equivalent 1-4 to provide compound 1-5.

For compounds of formula II-VI, $—(C(R_2)(R_3))_n—$ correspond to $—(CH_2—CH_2)—$ portion to between Y and T. Thus, for the synthesis of compounds of formulae II-VI, compound 1-1 would have the appropriate entities for $—(C(R_2)(R_3))_n—$ to result in the synthesis of compounds of formulae II-VI.

Trypsin Inhibitors

As used herein, the term "trypsin inhibitor" refers to any agent capable of inhibiting the action of trypsin on a substrate. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700.

There are many trypsin inhibitors known in the art, both those specific to trypsin and those that inhibit trypsin and other proteases such as chymotrypsin. Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, or phenylmethanesulfonyl fluoride. As used herein, an arginine or lysine mimic is a compound that is capable of binding to the $P^1$ pocket of trypsin and/or interfering with trypsin active site function.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are to available, for example from Sigma-Aldrich, St. Louis, Mo., USA.

It will be appreciated that the pharmaceutical composition according to the embodiments may further comprise one or more other trypsin inhibitors.

Small Molecule Trypsin Inhibitors

As stated above, a trypsin inhibitor can be an arginine or lysine mimic or other synthetic compound. In certain embodiments, the trypsin inhibitor is an arginine mimic or a lysine mimic, wherein the arginine mimic or lysine mimic is a synthetic compound.

Certain trypsin inhibitors include compounds of formula:

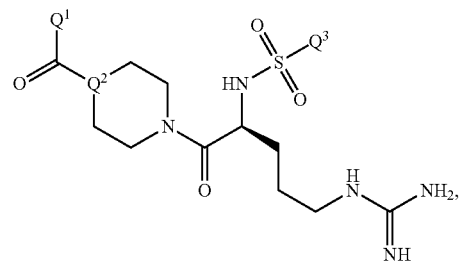

wherein:

$Q^1$ is selected from $—O-Q^4$ or $-Q^4$-COOH, where $Q^4$ is $C_1$-$C_4$ alkyl;

$Q^2$ is N or CH; and $Q^3$ is aryl or substituted aryl.

Certain trypsin inhibitors include compounds of formula:

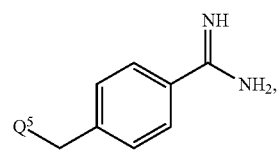

wherein:

$Q^5$ is $—C(O)—COOH$ or $—NH-Q^6-Q^7-SO_2—C_6H_5$, where $Q^6$ is $—(CH_2)_p—COOH$;

$Q^7$ is $—(CH_2)_r—C_6H_5$; and p is an integer from one to three; and r is an integer from one to three.

Certain trypsin inhibitors include the following:

| | | |
|---|---|---|
| Compound 101 | 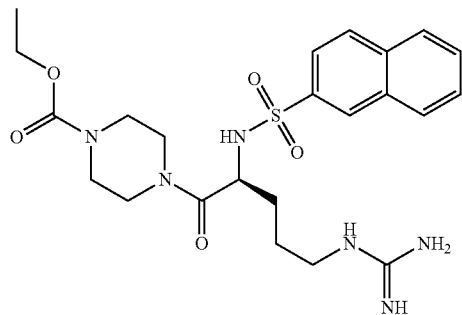 [SMILES: CCOC(=O)N1CCN(C(=O)[C@H](CCCNC(=N)N)NS(=O)(=O)c2ccc3ccccc3c2)CC1] | (S)-ethyl 4-(5-guanidino-2-(naphthalene-2-sulfonamido)pentanoyl)piperazine-1-carboxylate |
| Compound 102 | 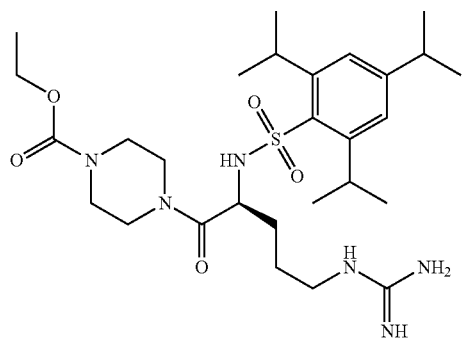 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 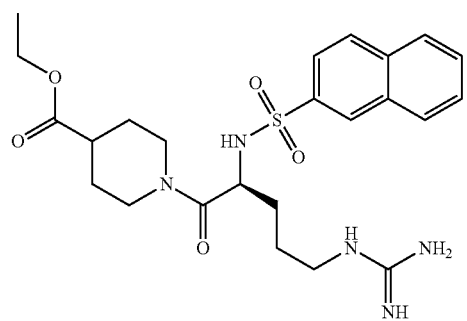 | (S)-ethyl 1-(5-guanidino-2-(naphthalene-2-sulfonamido)pentanoyl)piperidine-4-carboxylate |
| Compound 104 | 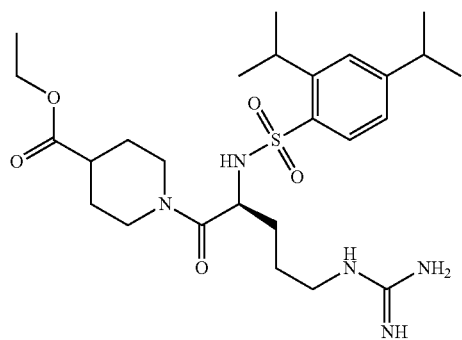 [SMILES: CCOC(=O)C1CCN(C(=O)[C@H](CCCNC(=N)N)NS(=O)(=O)c2ccc(C(C)C)cc2C(C)C)CC1] | (S)-ethyl 1-(5-guanidino-2-(2,4,6-triisopropylphenylsulfonamido)pentanoyl)piperidine-4-carboxylate |

-continued

| | | |
|---|---|---|
| Compound 105 | 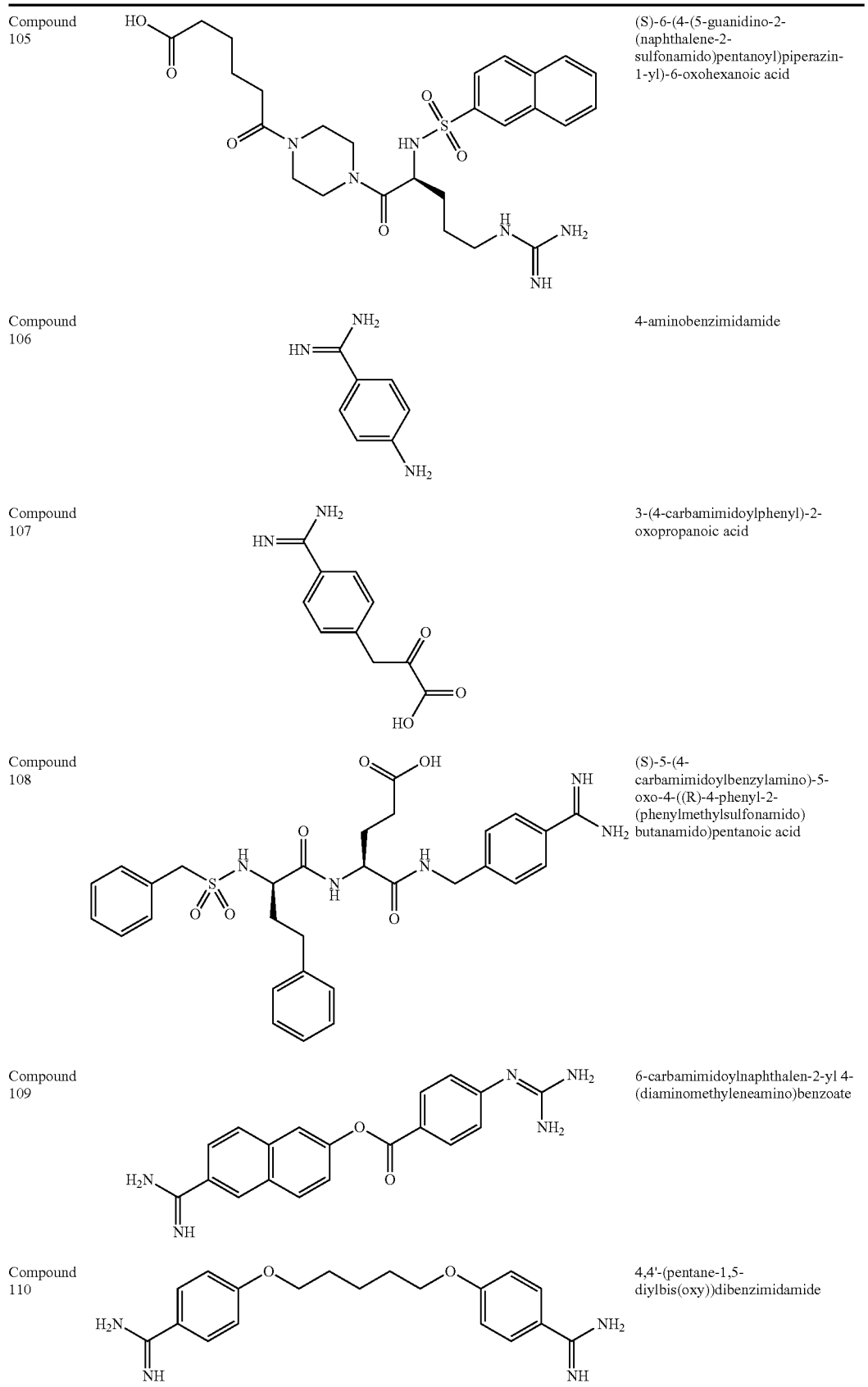 | (S)-6-(4-(5-guanidino-2-(naphthalene-2-sulfonamido)pentanoyl)piperazin-1-yl)-6-oxohexanoic acid |
| Compound 106 | | 4-aminobenzimidamide |
| Compound 107 | | 3-(4-carbamimidoylphenyl)-2-oxopropanoic acid |
| Compound 108 | | (S)-5-(4-carbamimidoylbenzylamino)-5-oxo-4-((R)-4-phenyl-2-(phenylmethylsulfonamido)butanamido)pentanoic acid |
| Compound 109 | | 6-carbamimidoylnaphthalen-2-yl 4-(diaminomethyleneamino)benzoate |
| Compound 110 | | 4,4'-(pentane-1,5-diylbis(oxy))dibenzimidamide |

In certain embodiments, the trypsin inhibitor is SBTI, BBSI, Compound 101, Compound 106, Compound 108, Compound 109, or Compound 110.

Pharmaceutical Compositions

As discussed above, the present disclosure provides pharmaceutical compositions which comprise a trypsin inhibitor and a phenolic opioid prodrug that contains a trypsin-labile moiety that, when cleaved, facilitates release of phenolic opioid. Examples of compositions containing a phenolic opioid prodrug and a trypsin inhibitors are described below.

Combinations of Formulae I-VI and Trypsin Inhibitor

The embodiments provide a pharmaceutical composition, which comprises a trypsin inhibitor and a compound of general Formula (I), or a pharmaceutically acceptable salt thereof.

The embodiments provide a pharmaceutical composition, which comprises a trypsin inhibitor and a compound of general Formulae (II)-(VI), or a pharmaceutically acceptable salt thereof.

Certain embodiments provide for a combination of a compound of Formula I and a trypsin inhibitor, in which the phenolic opioid of Formula I and the trypsin inhibitor are shown in the following table.

| Phenolic opioid | Trypsin inhibitor |
|---|---|
| Oxymorphone | SBTI |
| Oxymorphone | BBSI |
| Oxymorphone | Compound 101 |
| Oxymorphone | Compound 106 |
| Oxymorphone | Compound 108 |
| Oxymorphone | Compound 109 |
| Oxymorphone | Compound 110 |

Certain embodiments provide for a combination of a compound of formula I and trypsin inhibitor, in which the phenolic opioid of formula I and the trypsin inhibitor are shown in the following table.

| Phenolic opioid | Trypsin inhibitor |
|---|---|
| Hydromorphone | SBTI |
| Hydromorphone | BBSI |
| Hydromorphone | Compound 101 |
| Hydromorphone | Compound 106 |
| Hydromorphone | Compound 108 |
| Hydromorphone | Compound 109 |
| Hydromorphone | Compound 110 |

Certain embodiments provide for a combination of a compound of formula I and trypsin inhibitor, in which the phenolic opioid of formula I and the trypsin inhibitor are shown in the following table.

| Phenolic opioid | Trypsin inhibitor |
|---|---|
| Morphine | SBTI |
| Morphine | BBSI |
| Morphine | Compound 101 |
| Morphine | Compound 106 |
| Morphine | Compound 108 |
| Morphine | Compound 109 |
| Morphine | Compound 110 |

Certain embodiments provide for a combination of a compound of formula I and trypsin inhibitor, in which the phenolic opioid of formula I and the trypsin inhibitor are shown in the following table.

| Phenolic opioid | Trypsin inhibitor |
|---|---|
| Tapentadol | SBTI |
| Tapentadol | BBSI |
| Tapentadol | Compound 101 |
| Tapentadol | Compound 106 |
| Tapentadol | Compound 108 |
| Tapentadol | Compound 109 |
| Tapentadol | Compound 110 |

Certain embodiments provide for a combination of a compound of formula II and trypsin inhibitor, in which the phenolic opioid of formula II and the trypsin inhibitor are shown in the following table.

| Phenolic opioid | Trypsin inhibitor |
|---|---|
| Oxymorphone | SBTI |
| Oxymorphone | BBSI |
| Oxymorphone | Compound 101 |
| Oxymorphone | Compound 106 |
| Oxymorphone | Compound 108 |
| Oxymorphone | Compound 109 |
| Oxymorphone | Compound 110 |

Certain embodiments provide for a combination of a compound of formula II and trypsin inhibitor, in which the phenolic opioid of formula II and the trypsin inhibitor are shown in the following table.

| Phenolic opioid | Trypsin inhibitor |
|---|---|
| Hydromorphone | SBTI |
| Hydromorphone | BBSI |
| Hydromorphone | Compound 101 |
| Hydromorphone | Compound 106 |
| Hydromorphone | Compound 108 |
| Hydromorphone | Compound 109 |
| Hydromorphone | Compound 110 |

Certain embodiments provide for a combination of a compound of formula II and trypsin inhibitor, in which the phenolic opioid of formula II and the trypsin inhibitor are shown in the following table.

| Phenolic opioid | Trypsin inhibitor |
|---|---|
| Morphine | SBTI |
| Morphine | BBSI |
| Morphine | Compound 101 |
| Morphine | Compound 106 |
| Morphine | Compound 108 |
| Morphine | Compound 109 |
| Morphine | Compound 110 |

Certain embodiments provide for a combination of a compound of formula II and trypsin inhibitor, in which the phenolic opioid of formula II and the trypsin inhibitor are shown in the following table.

| Phenolic opioid | Trypsin inhibitor |
|---|---|
| Tapentadol | SBTI |
| Tapentadol | BBSI |
| Tapentadol | Compound 101 |
| Tapentadol | Compound 106 |

| Phenolic opioid | Trypsin inhibitor |
| --- | --- |
| Tapentadol | Compound 108 |
| Tapentadol | Compound 109 |
| Tapentadol | Compound 110 |

Certain embodiments provide for a combination of a compound of formula III and trypsin inhibitor, in which the phenolic opioid of formula III and the trypsin inhibitor are shown in the following table.

| Phenolic opioid | Trypsin inhibitor |
| --- | --- |
| Oxymorphone | SBTI |
| Oxymorphone | BBSI |
| Oxymorphone | Compound 101 |
| Oxymorphone | Compound 106 |
| Oxymorphone | Compound 108 |
| Oxymorphone | Compound 109 |
| Oxymorphone | Compound 110 |

Certain embodiments provide for a combination of a compound of formula III and trypsin inhibitor, in which the phenolic opioid of formula III and the trypsin inhibitor are shown in the following table.

| Phenolic opioid | Trypsin inhibitor |
| --- | --- |
| Hydromorphone | SBTI |
| Hydromorphone | BBSI |
| Hydromorphone | Compound 101 |
| Hydromorphone | Compound 106 |
| Hydromorphone | Compound 108 |
| Hydromorphone | Compound 109 |
| Hydromorphone | Compound 110 |

Certain embodiments provide for a combination of a compound of formula III and trypsin inhibitor, in which the phenolic opioid of formula III and the trypsin inhibitor are shown in the following table.

| Phenolic opioid | Trypsin inhibitor |
| --- | --- |
| Morphine | SBTI |
| Morphine | BBSI |
| Morphine | Compound 101 |
| Morphine | Compound 106 |
| Morphine | Compound 108 |
| Morphine | Compound 109 |
| Morphine | Compound 110 |

Certain embodiments provide for a combination of a compound of formula III and trypsin inhibitor, in which the phenolic opioid of formula III and the trypsin inhibitor are shown in the following table.

| Phenolic opioid | Trypsin inhibitor |
| --- | --- |
| Tapentadol | SBTI |
| Tapentadol | BBSI |
| Tapentadol | Compound 101 |
| Tapentadol | Compound 106 |
| Tapentadol | Compound 108 |
| Tapentadol | Compound 109 |
| Tapentadol | Compound 110 |

Certain embodiments provide for a combination of Compound 1 and trypsin inhibitor, in which the trypsin inhibitor is shown in the following table.

| Compound | Trypsin inhibitor |
| --- | --- |
| Compound 1 | SBTI |
| Compound 1 | BBSI |
| Compound 1 | Compound 101 |
| Compound 1 | Compound 106 |
| Compound 1 | Compound 108 |
| Compound 1 | Compound 109 |
| Compound 1 | Compound 110 |

Certain embodiments provide for a combination of Compound 2 and trypsin inhibitor, in which the trypsin inhibitor is shown in the following table.

| Compound | Trypsin inhibitor |
| --- | --- |
| Compound 2 | SBTI |
| Compound 2 | BBSI |
| Compound 2 | Compound 101 |
| Compound 2 | Compound 106 |
| Compound 2 | Compound 108 |
| Compound 2 | Compound 109 |
| Compound 2 | Compound 110 |

Certain embodiments provide for a combination of Compound 3 and trypsin inhibitor, in which the trypsin inhibitor is shown in the following table.

| Compound | Trypsin inhibitor |
| --- | --- |
| Compound 3 | SBTI |
| Compound 3 | BBSI |
| Compound 3 | Compound 101 |
| Compound 3 | Compound 106 |
| Compound 3 | Compound 108 |
| Compound 3 | Compound 109 |
| Compound 3 | Compound 110 |

Certain embodiments provide for a combination of Compound 4 and trypsin inhibitor, in which the trypsin inhibitor is shown in the following table.

| Compound | Trypsin inhibitor |
| --- | --- |
| Compound 4 | SBTI |
| Compound 4 | BBSI |
| Compound 4 | Compound 101 |
| Compound 4 | Compound 106 |
| Compound 4 | Compound 108 |
| Compound 4 | Compound 109 |
| Compound 4 | Compound 110 |

It is to be appreciated that the invention also includes inhibitors of other enzymes involved in protein assimilation that can be used in combination with a prodrug having a formula or any of I-VI comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

The pharmaceutical composition according to the embodiments is useful, for example, in the treatment of a patient suffering from, or at risk of suffering from pain.

The patient can be a human or a non-human animal, for example a companion animal such as a cat, dog or horse.

Methods of Administration

The amount of compound of formulae (I)-(VI) to be administered to a patient to be effective (i.e. to provide blood levels of phenolic opioid sufficient to be effective in the treatment or prophylaxis of pain) will depend upon the bioavailability of the particular compound, the susceptibility of the particular compound to enzyme activation in the gut, the amount and potency of trypsin inhibitor present in the composition, as well as other factors, such as the species, age, weight, sex, and condition of the patient, manner of administration and judgment of the prescribing physician. In general, the dose can be in the range of from 0.01 to 20 milligrams per kilogram (mg/kg) body weight. For example, a compound comprising a residue of hydromorphone can be administered at a dose equivalent to administering free hydromorphone in the range of from 0.02 to 0.5 mg/kg body weight or 0.01 to 10 mg/kg body weight or 0.01 to 2 mg/kg body weight. In one embodiment, the compound can be administered at a dose such that the level of phenolic opioid achieved in the blood is in the range of from 0.5 ng/ml to 10 ng/ml.

The amount of a trypsin inhibitor to be administered to the patient to be effective (i.e. to attenuate release of phenolic opioid when administration of a compound of formulae (I)-(VI) alone would lead to overexposure of the phenolic opioid) will depend upon the effective dose of the particular compound and the potency of the particular inhibitor, as well as other factors, such as the species, age, weight, sex and condition of the patient, manner of administration and judgment of the prescribing physician. In general, the dose of inhibitor can be in the range of from 0.05 to 50 mg per mg of compound of formulae (I)-(VI). In a certain embodiment, the dose of inhibitor can be in the range of from 0.001 to 50 mg per mg of compound of formulae (I)-(VI).

Therapeutic Applications

In another aspect, the embodiments provide a pharmaceutical composition as described hereinabove for use in the treatment of pain.

The present disclosure provides use of a phenolic opioid prodrug and a trypsin inhibitor in the treatment of pain.

The present disclosure provides use of a phenolic opioid prodrug and a trypsin inhibitor in the manufacture of a medicament for treatment of pain.

In another aspect, the embodiments provides method of treating pain in a patient requiring treatment, which comprises administering an effective amount of a pharmaceutical composition as described hereinabove.

Thwarting Tamerping by Trypsin Mediated Release of Phenolic Opioid from Prodrugs The disclosure provides for a composition comprising a compound of formulae I-VI and a trypsin inhibitor that reduces drug abuse potential. A trypsin inhibitor can thwart the ability of a user to apply trypsin to effect the release of a phenolic opioid from the phenolic opioid prodrug in vitro. For example, if an abuser attempts to incubate trypsin with a composition of the embodiments that includes a phenolic opioid prodrug and a trypsin inhibitor, the trypsin inhibitor can reduce the action of the added trypsin, thereby thwarting attempts to release phenolic opioid for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Example 1

Oral Administration of Compound 1 and SBTI Trypsin Inhibitor to Rats

Hydromorphone 3-(N-methyl-N-(2-N'-acetylarginylamino)) ethylcarbamate (which can be produced as described in PCT International Publication No. WO 2007/140272, published 6 Dec. 2007, Example 3, hereinafter referred to as Compound 1) and SBTI to (trypsin inhibitor from *Glycine max* (soybean) (Catalog No. 93620, ~10,000 units per mg, Sigma-Aldrich) were each dissolved in saline.

Saline solutions of Compound 1 and SBTI were dosed as indicated in Table 1 via oral gavage into jugular vein-cannulated male Sprague Dawley rats that had been fasted for 16-18 hours (hr) prior to oral dosing; 4 rats were dosed per group. When SBTI was dosed, it was administered 5 minutes (min) prior to Compound 1. At specified time points, blood samples were drawn, quenched into methanol, centrifuged at 14,000 rpm @ 4° C., and stored at −80° C. until analysis by high performance liquid chromatography/mass spectrometry (HPLC/MS).

Table 1 indicates the results for rats administered a constant amount of Compound 1 and variable amounts of SBTI. Results are reported as maximum blood concentration of hydromorphone (average±standard deviation) for each group of 4 rats.

TABLE 1

| Maximum concentration (Cmax) of hydromorphone in rat blood | | |
|---|---|---|
| Compound 1 (mg/kg) | SBTI (mg/kg) | Cmax (ng/ml HM) |
| 20 | 0 | 16.5 ± 5.3 |
| 20 | 10 | 8.9 ± 1.8 |
| 20 | 100 | 6.0 ± 4.0 |
| 20 | 500 | <5 |
| 20 | 1000 | <5 |

Lower limit of quantitation was 1 nanogram per milliliter (ng/ml) for the first group and 5 ng/ml for the other groups.

The results in Table 1 indicate that SBTI attenuates Compound 1's ability to release hydromorphone in a dose-dependent manner that can approach approximately 100% attenuation at higher SBTI concentrations.

Data obtained from the rats represented in Table 1 are also provided in FIG. 1 which compares mean blood concentrations (±standard deviations) over time of hydromorphone following PO administration to rats of 20 mg/kg Compound 1 (a) alone (solid line with closed circle symbols), (b) with 10 mg/kg SBTI (dashed line with open square symbols), (c) with 100 mg/kg SBTI (dotted line with open triangle symbols), (d) with 500 mg/kg SBTI (solid line with X symbols) or (e) with 1000 mg/kg SBTI (solid line with closed square symbols). The results in FIG. 1 indicate that SBTI attenuation of Compound 1's ability to release hydromorphone suppresses Cmax and delays Tmax of such hydromorphone release into the blood of rats administered Compound 1 and 10, 100, 500 or 1000 mg/kg SBTI.

Example 2

Oral Administration of Compound 1 and SBTI Trypsin Inhibitor, in the Presence of Ovalbumin, to Rats In an effort to understand the role of SBTI, ovalbumin was used as a non-trypsin inhibitor protein control. Albumin from chicken egg white (ovalbumin) (Catalog No. A7641, Grade VII, lyophilized powder, Sigma-Aldrich) was dissolved in saline.

Saline solutions of Compound 1 and SBTI (as described in Example 1) and of ovalbumin were combined and dosed as indicated in Table 2 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (µl) plasma transferred from each sample into a fresh tube containing 1 µl of formic acid. The tubes were vortexed for 5-10 seconds, immediately placed in dry ice and then stored until analysis by HPLC/MS.

Table 2 indicates the results for rats administered Compound 1 with or without various amounts of ovalbumin (OVA) and/or SBTI as indicated. Results are reported as maximum plasma concentration of hydromorphone (average±standard deviation) for each group of 4 rats.

TABLE 2

Maximum concentration (Cmax) of hydromorphone in rat plasma

| Compound 1 (mg/kg) | OVA (mg/kg) | SBTI (mg/kg) | Cmax (ng/ml HM) |
|---|---|---|---|
| 20 | 0 | 0 | 13.3 ± 3.7 |
| 20 | 20 | 0 | 11.0 ± 5.4 |
| 20 | 100 | 0 | 9.7 ± 3.1 |
| 20 | 500 | 0 | 11.6 ± 2.5 |
| 20 | 1000 | 0 | 10.3 ± 3.5 |
| 20 | 500 | 500 | 1.9 ± 0.9 |

Lower limit of quantitation was 12.5 picograms/ml (pg/ml) for the first group, 25 pg/ml for the last group, and 100 pg/ml for the other groups.

The results in Table 2 indicate that ovalbumin does not significantly affect Compound 1's ability to release hydromorphone or SBTI's ability to attenuate such release.

Figure 2:
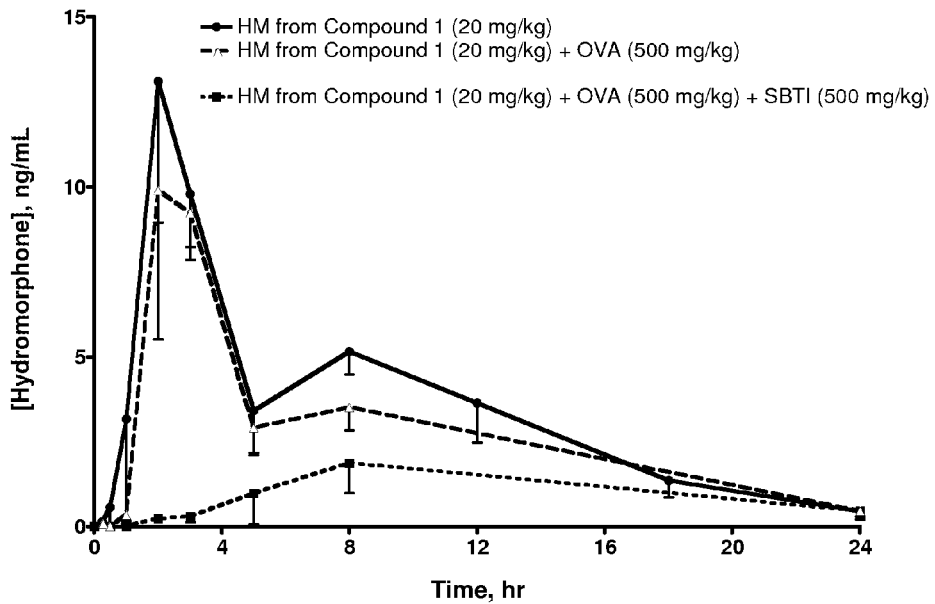
FIG. 2 is a graph that compares mean plasma concentrations over time of hydromorphone (HM) following PO administration to rats of Compound 1 alone, Compound 1 with ovalbumin (OVA), and Compound 1 with ovalbumin and SBTI.

Data obtained from the rats represented in rows 1, 4 and 6 of Table 2 are also provided in FIG. 2 which compares mean plasma concentrations (±standard deviations) over time of hydromorphone following PO administration to rats of 20 mg/kg Compound 1 (a) alone (solid line with circle symbols), (b) with 500 mg/kg OVA (dashed line with triangle symbols) or (c) with 500 mg/kg OVA and 500 mg/kg SBTI (dotted line with square symbols). The results in FIG. 2 indicate that SBTI attenuation of Compound 1's ability to release hydromorphone suppresses Cmax and delays Tmax of such hydromorphone in to plasma, even in the presence of ovalbumin Rats administered 20 mg/kg Compound 1 with 500 mg/kg OVA and 500 mg/kg SBTI displayed a plasma Tmax of 8.0 hr, whereas rats administered 20 mg/kg Compound 1 alone displayed a plasma Tmax of 2.3 hr. The results in Table 2 and FIG. 2 also indicate that SBTI is acting specifically by inhibiting trypsin rather than in a non-specific manner.

Example 3

Oral Administration of Compound 1 and BBSI Inhibitor to Rats

Compound 1 and BBSI (Bowman-Birk trypsin-chymotrypsin inhibitor from *Glycine max* (soybean), Catalog No. T9777, Sigma-Aldrich) were each dissolved in saline.

Saline solutions of Compound 1 and BBSI were dosed as indicated in Table 3. Dosing, sampling and analysis procedures were as described in Example 1.

Table 3 indicates the results for rats administered Compound 1 with or without BBSI. Results are reported as maximum blood concentration of hydromorphone (average±standard deviation) for each group of 4 rats (n=4) as well as for 3 of the 4 rats administered Compound 1 and BBSI (n=3).

TABLE 3

Maximum concentration (Cmax) of hydromorphone in rat blood

| Compound 1 (mg/kg) | BBSI (mg/kg) | Cmax (ng/ml HM) | Number of Rats (n) |
|---|---|---|---|
| 20 | 0 | 16.5 ± 5.3 | n = 4 |
| 20 | 100 | 10.6 ± 5.9 | n = 3 |
| 20 | 100 | 18.7 ± 17.0 | n = 4 |

Lower limit of quantitation was 1 ng/ml for both groups. Cmax of rat not included in n = 3 analysis was 43 ng/ml; range of other rats was 6.8-17 ng/ml.

The results in Table 3 indicate that BBSI can attenuate Compound 1's ability to release hydromorphone.

Figure 3:
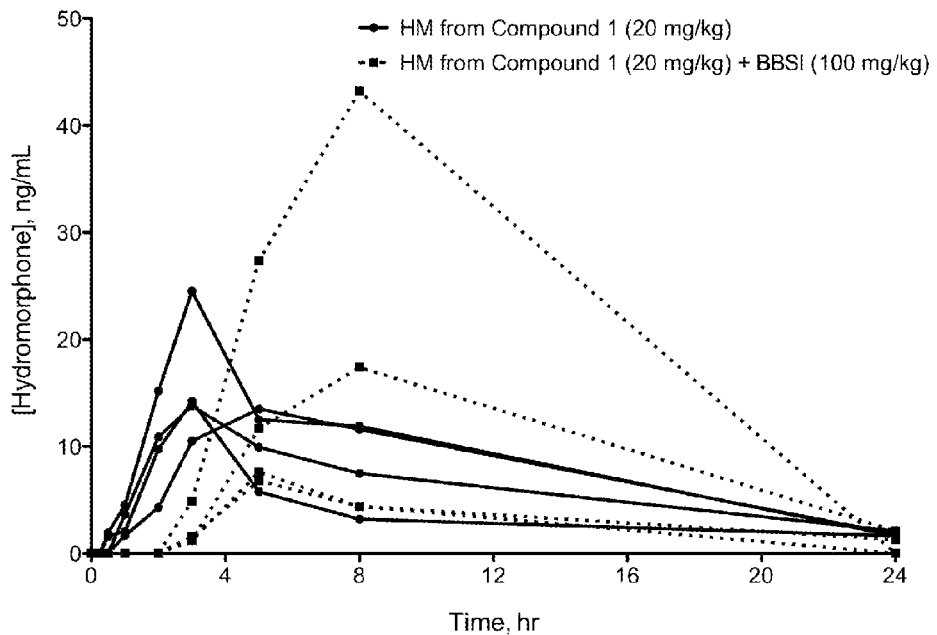
FIG. 3 is a graph that compares individual blood concentrations over time of hydromorphone (HM) following PO administration to rats of Compound 1 alone and Compound 1 with Bowman-Birk trypsin-chymotrypsin inhibitor (BBSI).

Data obtained from the individual rats represented in Table 3, rows 1 and 3 are provided in FIG. 3 which compares individual blood concentrations over time of hydromorphone following PO administration to rats of 20 mg/kg Compound 1 (a) alone (solid lines) or (b) with 100 mg/kg BBSI (dotted lines). The results in FIG. 3 indicate that BBSI attenuation of Compound 1's ability to release hydromorphone suppresses Cmax and delays Tmax of such hydromorphone in blood, at least for 3 of the 4 rats administered Compound 1 and BBSI.

Example 4

Oral Administration of Compound 2 and SBTI Trypsin Inhibitor to Rats

Saline solutions of Compound 2 (which can be prepared as described in Example 11) and SBTI (which can be prepared as described in Example 1) were dosed as indicated in Table 4 via oral gavage into jugular vein-cannulated male Sprague Dawley rats (4 per group) that had been fasted for 16-18 hr prior to oral dosing. When SBTI was dosed, it was administered 5 min prior to Compound 4. At specified time points, blood samples were drawn, processed and analyzed as described in Example 2.

Figure 4:
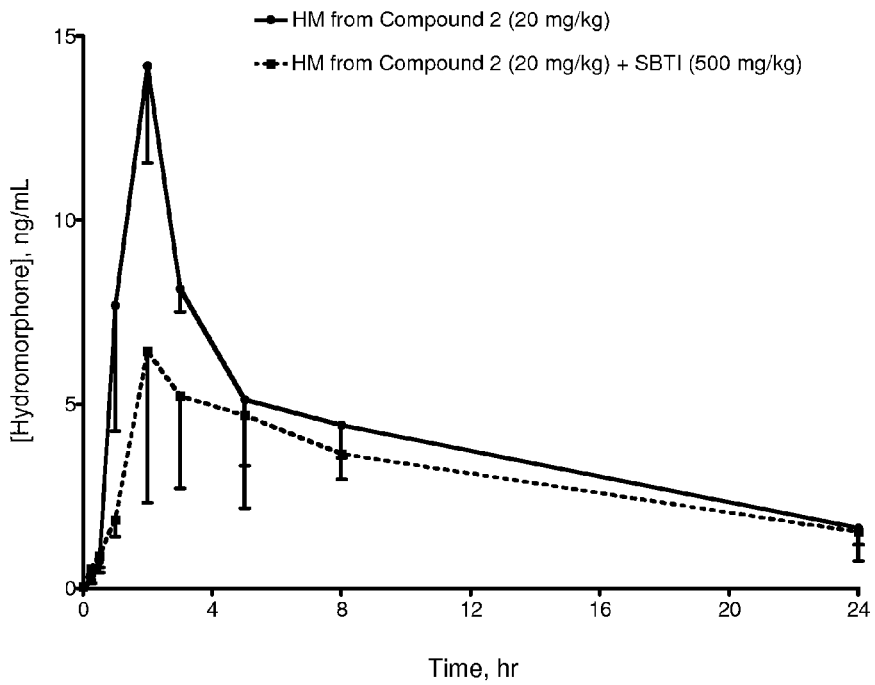
FIG. 4 is a graph that compares mean plasma concentrations over time of hydromorphone (HM) release following PO administration of Compound 2 alone and Compound 2 with SBTI to rats.

Table 4 and FIG. 4 provide results for rats administered 20 mg/kg of Compound 2 with or without 500 mg/kg of SBTI as indicated. Results in Table 4 are reported, for each group of 4 rats, as (a) maximum plasma concentration (Cmax) of hydromorphone (HM) (average±standard deviation) and (b) time after administration of Compound 2, with or without SBTI, to reach maximum hydromorphone concentration (Tmax).

TABLE 4

Cmax and Tmax of hydromorphone in rat plasma

| Compound 2 (mg/kg) | SBTI (mg/kg) | Cmax (ng/ml HM) | Tmax (hr) |
|---|---|---|---|
| 20 | 0 | 14.2 ± 2.6 | 2.0 |
| 20 | 500 | 7.3 ± 3.5 | 3.5 |

Lower limit of quantitation was 0.0125 ng/ml for both groups.

FIG. 4 compares mean plasma concentrations (±standard deviations) over time of hydromorphone release following PO administration of 20 mg/kg Compound 2 alone (solid line) or with 500 mg/kg SBTI (dotted line) to rats.

The results in Table 4 and FIG. 4 indicate that SBTI attenuates Compound 2's ability to release hydromorphone, both with respect to suppressing Cmax and delaying Tmax.

Example 5

Oral Administration of Compound 3 and SBTI Trypsin Inhibitor to Rats

Saline solutions of Compound 3 (which can be prepared as described in Example 12) and SBTI were dosed as indicated in Table 5. Dosing, sampling and analysis procedures were as described in Example 4.

Figure 5:
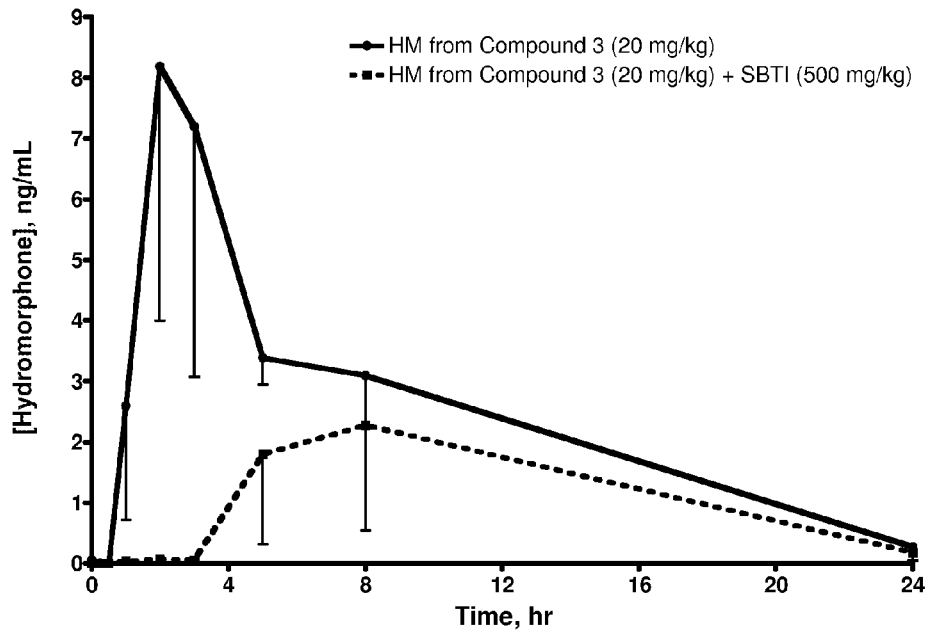
FIG. 5 is a graph that compares mean plasma concentrations over time of hydromorphone (HM) release following PO administration of Compound 3 alone and Compound 3 with SBTI to rats.

Table 5 and FIG. 5 provide results for rats administered 20 mg/kg of Compound 3 with or without 500 mg/kg of SBTI as indicated. Results in Table 5 are reported as Cmax and Tmax of hydromorphone in plasma for each group of 4 rats.

TABLE 5

Cmax and Tmax of hydromorphone in rat plasma

| Compound 3 (mg/kg) | SBTI (mg/kg) | Cmax (ng/ml HM) | Tmax (hr) |
|---|---|---|---|
| 20 | 0 | 9.0 ± 3.1 | 2.3 |
| 20 | 500 | 2.3 ± 1.7 | 7.3 |

Lower limit of quantitation was 0.100 ng/ml for both groups.

FIG. 5 compares mean plasma concentrations (±standard deviations) over time of hydromorphone release following PO administration of 20 mg/kg Compound 3 alone (solid line) or with 500 mg/kg SBTI (dotted line) to rats.

The results in Table 5 and FIG. 5 indicate that SBTI attenuates Compound 3's ability to release hydromorphone, both with respect to suppressing Cmax and delaying Tmax.

Example 6

Oral Administration of Compound 4 and SBTI Trypsin Inhibitor to Rats

Saline solutions of Compound 4 (which can be prepared as described in Example 13) and SBTI were dosed as indicated in Table 6. Dosing, sampling and analysis procedures were as described in Example 4, except that Compound 4 without inhibitor was administered to 7 rats.

Figure 6:
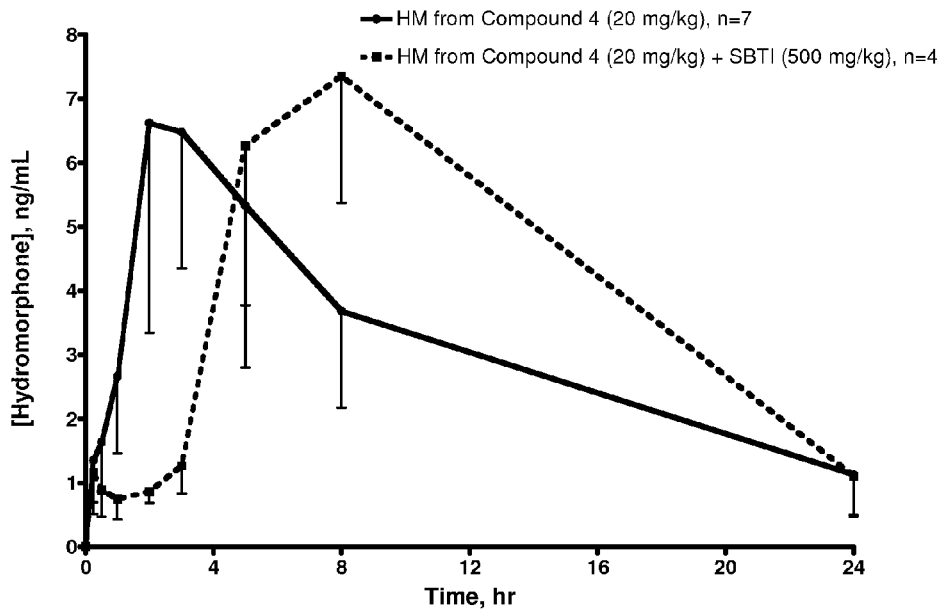
FIG. 6 is a graph that compares mean plasma concentrations over time of hydromorphone (HM) release following PO administration of Compound 4 alone and Compound 4 with SBTI to rats.

Table 6 and FIG. 6 provide results for rats administered 20 mg/kg of Compound 4 with or without 500 mg/kg of SBTI as indicated. Results in Table 6 are reported as Cmax and Tmax of hydromorphone in plasma for each group of 4 rats.

TABLE 6

Cmax and Tmax of HM in rat plasma

| Compound 4 (mg/kg) | SBTI (mg/kg) | Cmax (ng/ml HM) | Tmax (hr) | Number of rats (n) |
|---|---|---|---|---|
| 20 | 0 | 7.7 ± 2.3 | 2.3 | 7 |
| 20 | 500 | 7.5 ± 2.1 | 6.5 | 4 |

Lower limit of quantitation was 0.500 ng/ml for both groups.

FIG. 6 compares mean plasma concentrations (±standard deviations) over time of hydromorphone release following PO administration of 20 mg/kg Compound 4 alone (solid line) or with 500 mg/kg SBTI (dotted line) to rats.

The results in Table 6 and FIG. 6 indicate that SBTI attenuates Compound 4's ability to release hydromorphone, at least with respect to delaying Tmax.

Example 7

In vitro IC50 Data

Several candidate trypsin inhibitors, namely Compounds 101-105, 107 and 108 were to produced as described in Examples 14-18, 19 and 20, respectively. Compound 106 (also known as 4-aminobenzamidine), Compound 109 (also known as nafamostat mesylate) and Compound 110 (also known as pentamidine isethionate salt) are available from Sigma-Aldrich (St. Louis, Mo.).

The half maximal inhibitory concentration (IC50 or $IC_{50}$) values of each of Compounds 101-110 as well as of SBTI and BBSI were determined using a modified trypsin assay as described by Bergmeyer, H U et al, 1974, Methods of Enzymatic Analysis Volume 1, $2^{nd}$ edition, 515-516, Bergmeyer, H U, ed., Academic Press, Inc. New York, N.Y.

Table 7 indicates the IC50 values for each of the designated trypsin inhibitors.

TABLE 7

IC50 values of certain trypsin inhibitors

| Compound | IC50 value |
|---|---|
| 101 | 2.0E−5 |
| 102 | 7.5E−5 |
| 103 | 2.3E−5 |
| 104 | 2.7E−5 |
| 105 | 4.1E−5 |
| 106 | 2.4E−5 |
| 107 | 1.9E−6 |
| 108 | 8.8E−7 |
| 109 | 9.1E−7 |
| 110 | 1.8E−5 |
| SBTI | 2.7E−7 |
| BBSI | 3.8E−7 |

The results of Table 7 indicate that each of Compounds 101-110 exhibits trypsin inhibition activity.

Example 8

Effect of Trypsin Inhibitors on In Vitro Trypsin-Mediated Trypsin Release of Hydromorphone from Compound 4

Compound 4 (which can be produced as described in Example 13) was incubated with trypsin from bovine pancreas (Catalog No. T8003, Type I, ~10,000 BAEE units/mg protein, Sigma-Aldrich) in the absence or presence of one of the following trypsin inhibitors: SBTI, Compound 107, Compound 108 or Compound 109. When a trypsin inhibitor was part of the incubation mixture, Compound 4 was added 5 min after the other incubation components. The reactions were conducted at 37° C. for 24 hr. Samples were collected at specified time points, transferred into 0.5% formic acid in acetonitrile to stop trypsin activity and stored at to less than −70° C. until analysis by LC-MS/MS.

The final incubation mixtures consisted of the following components:

| Compound | Incubation Components | | | | |
|---|---|---|---|---|---|
| | Inhibitor | Tris pH 8 | $CaCl_2$ | Trypsin | Compound 4 |
| Control | 0 | 40 mM | 22.5 mM | 0.0228 mg/mL | 0.51 mg/ml |
| 107 | 1.67 mg/mL | 20 mM | 22.5 mM | 0.0228 mg/mL | 0.51 mg/ml |
| 108 | 1.67 mg/mL | 20 mM | 22.5 mM | 0.0228 mg/mL | 0.51 mg/ml |
| 109 | 1.67 mg/mL | 20 mM | 22.5 mM | 0.0228 mg/mL | 0.51 mg/ml |
| SBTI | 10 mg/mL | 20 mM | 22.5 mM | 0.0228 mg/mL | 0.51 mg/ml |

Figure 7A:
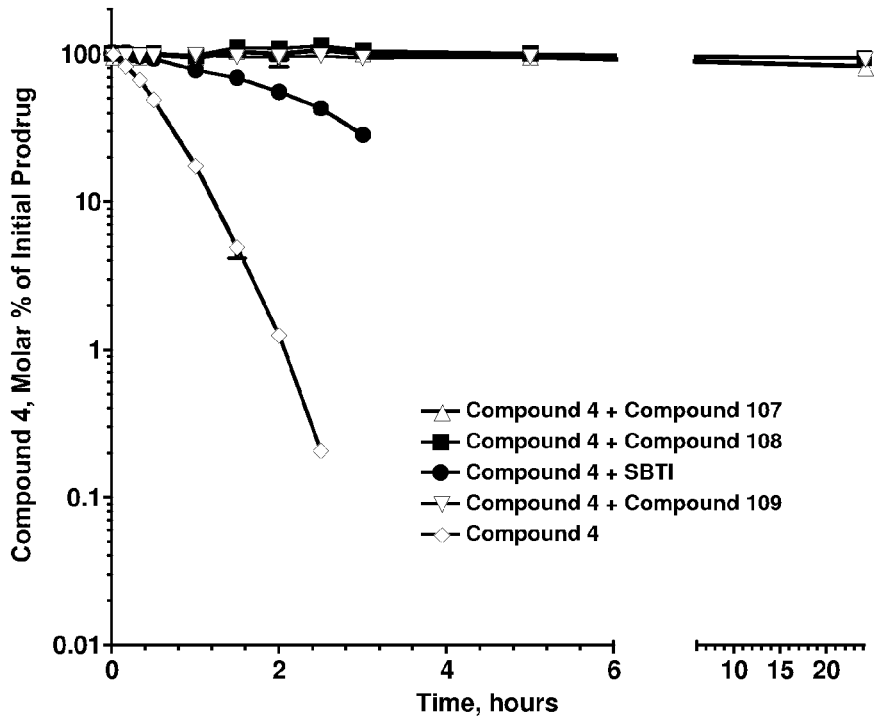
FIGS. 7A and 7B are graphs that indicate the results of exposure of a certain combination of Compound 4 and trypsin, in the absence of any trypsin inhibitor or in the presence of SBTI, Compound 107, Compound 108, or Compound 109.
Figure 7B:
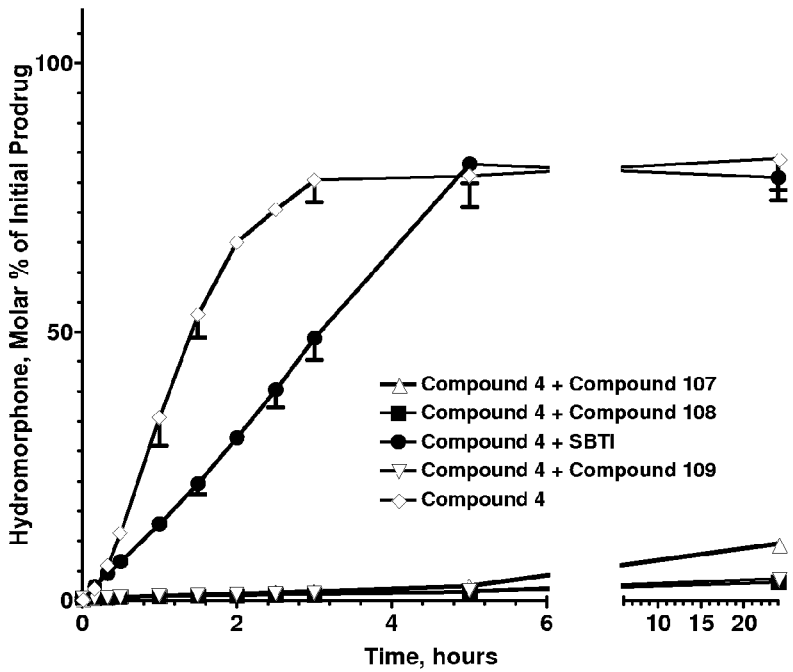

FIGS. 7A and 7B indicate the results of exposure of 0.51 mg/ml Compound 4 to 22.8 ng/ml trypsin in the absence of any trypsin inhibitor (diamond symbols) or in the presence of 10 mg/ml SBTI (circle symbols), 1.67 mg/ml Compound 107 (upward-pointing triangle symbols), 1.67 mg/ml Compound 108 (square symbols) or 1.67 mg/ml Compound 109 (downward-pointing triangles symbols). Specifically, FIG. 7A depicts the disappearance of Compound 4, and FIG. 7B depicts the appearance of hydromorphone, over time under these conditions.

The results in FIGS. 7A and 7B indicate that a trypsin inhibitor of the embodiments can thwart the ability of a user to apply trypsin to effect the release of hydromorphone from Compound 4.

Example 9

Oral Administration of Compound 3 and Compound 101 Trypsin Inhibitor to Rats Saline solutions of Compound 3 (which can be prepared as described in Example 12) and Compound 101 (prepared as described in Example 14) were dosed as indicated in Table 8. Dosing, sampling and analysis procedures were as described in Example 4, except that Compound 3 and Compound 101 were combined for dosing.

Figure 8:
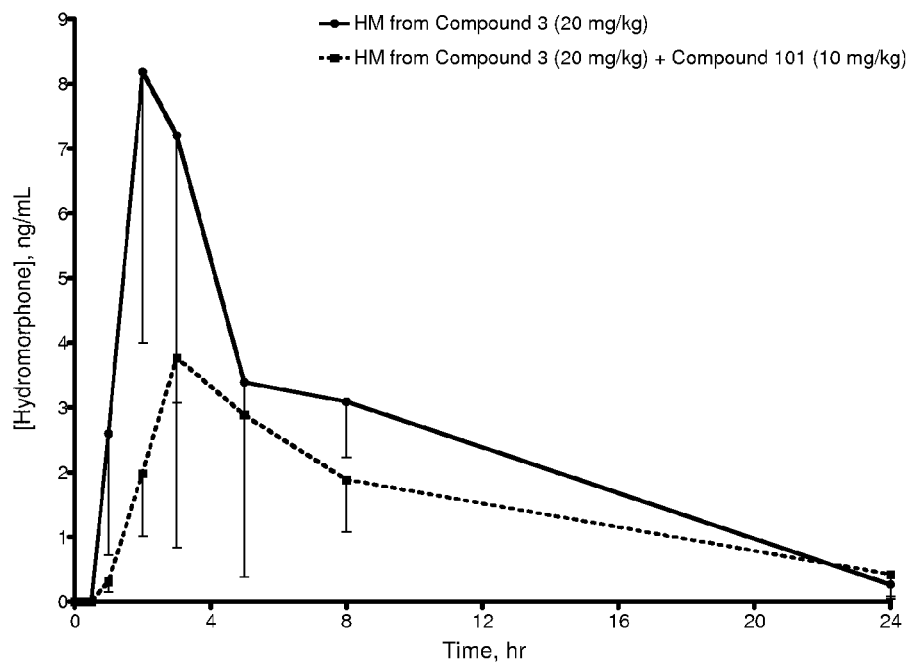
FIG. 8 is a graph that compares mean plasma concentrations over time of hydromorphone (HM) release following PO administration of Compound 3 alone and Compound 3 with Compound 101 to rats.

Table 8 and FIG. 8 provide results for rats administered 20 mg/kg of Compound 3 with or without 10 mg/kg of Compound 101 as indicated. Results in Table 8 are reported as Cmax and Tmax of hydromorphone in plasma for each group of 4 rats.

TABLE 8

| Cmax and Tmax of HM in rat plasma | | | |
|---|---|---|---|
| Compound 3 (mg/kg) | Compound 101 (mg/kg) | Cmax (ng/ml HM) | Tmax (hr) |
| 20 | 0 | 9.0 ± 3.1 | 2.3 |
| 20 | 10 | 3.8 ± 2.9 | 3.5 |

Lower limit of quantitation was 0.100 ng/ml for the first group and 0.500 ng/ml for the second group.

FIG. 8 compares mean plasma concentrations (±standard deviations) over time of hydromorphone release following PO administration of 20 mg/kg Compound 3 alone (solid line) or with 10 mg/kg Compound 101 (dotted line) to rats.

The results in Table 8 and FIG. 8 indicate that Compound 101 attenuates Compound 3's ability to release hydromorphone, both with respect to suppressing Cmax and delaying Tmax.

Example 10

Oral Administration of Compound 4 and Compound 101 Trypsin Inhibitor to Rats Saline solutions of Compound 4 (which can be prepared as described in Example 13) and Compound 101 (prepared as described in Example 14) were dosed as indicated in Table 9. Dosing, sampling and analysis procedures were as described in Example 4, except that Compound 4 and Compound 101 were combined for dosing, and Compound 4 without inhibitor was administered to 7 rats.

Figure 9:
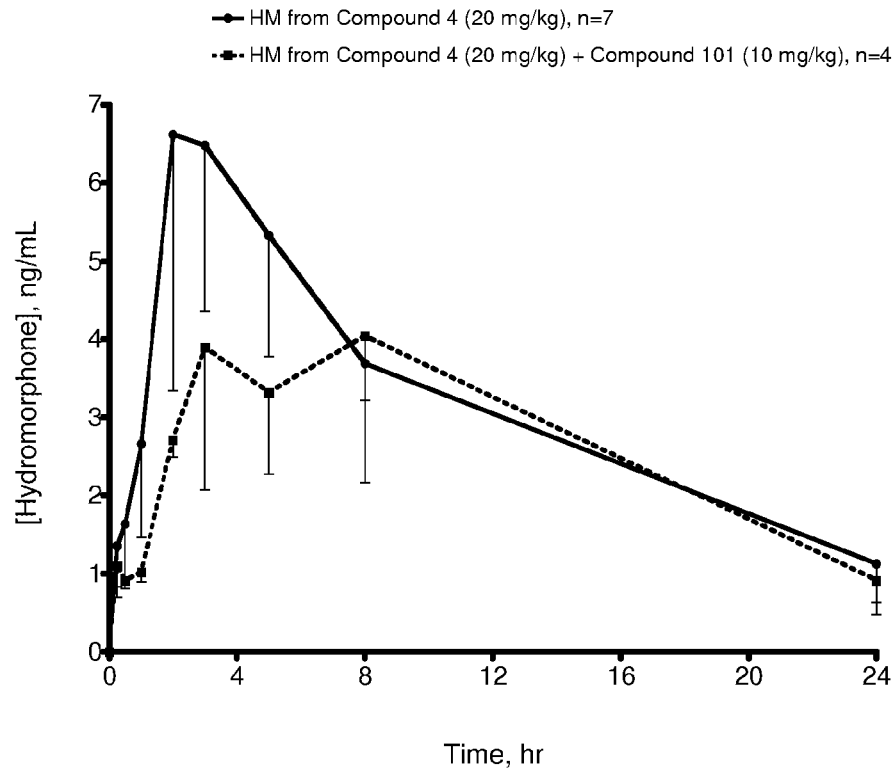
FIG. 9 is a graph that compares mean plasma concentrations over time of hydromorphone (HM) release following PO administration of Compound 4 alone and Compound 4 with Compound 101 to rats.

Table 9 and FIG. 9 provide results for rats administered 20 mg/kg of Compound 4 with or without 10 mg/kg of Compound 101 as indicated. Results in Table 9 are reported as Cmax and Tmax of hydromorphone in plasma for each group of 4 rats.

TABLE 9

| Cmax and Tmax of HM in rat plasma | | | | |
|---|---|---|---|---|
| Compound 4 (mg/kg) | Compound 101 (mg/kg) | Cmax (ng/ml HM) | Tmax (hr) | Number of rats (n) |
| 20 | 0 | 7.7 ± 2.3 | 2.3 | 7 |
| 20 | 10 | 4.8 ± 1.4 | 6.0 | 4 |

Lower limit of quantitation was 0.500 ng/ml for both groups.

FIG. 9 compares mean plasma concentrations (±standard deviations) over time of hydromorphone release following PO administration of 20 mg/kg Compound 4 alone (solid line) or with 10 mg/kg Compound 101 (dotted line) to rats.

The results in Table 9 and FIG. 9 indicate that Compound 101 attenuates Compound 4's ability to release hydromorphone, both with respect to suppressing Cmax and delaying Tmax.

Example 11
Synthesis of [2-((S)-2-amino-5-guanidino-pentanoylamino)-ethyl]-methyl-carbamic acid hydromorphyl ester (Compound 2)
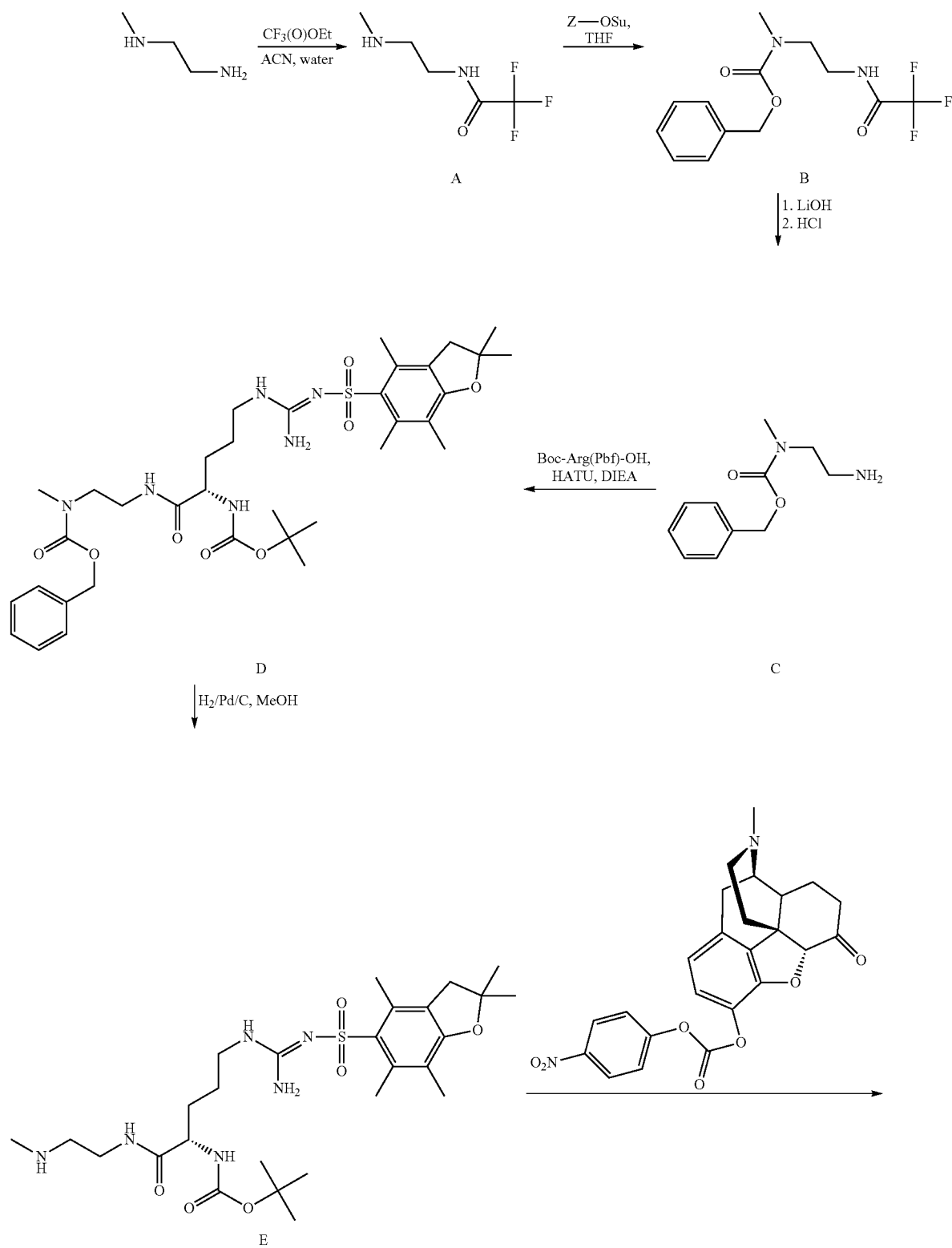

-continued

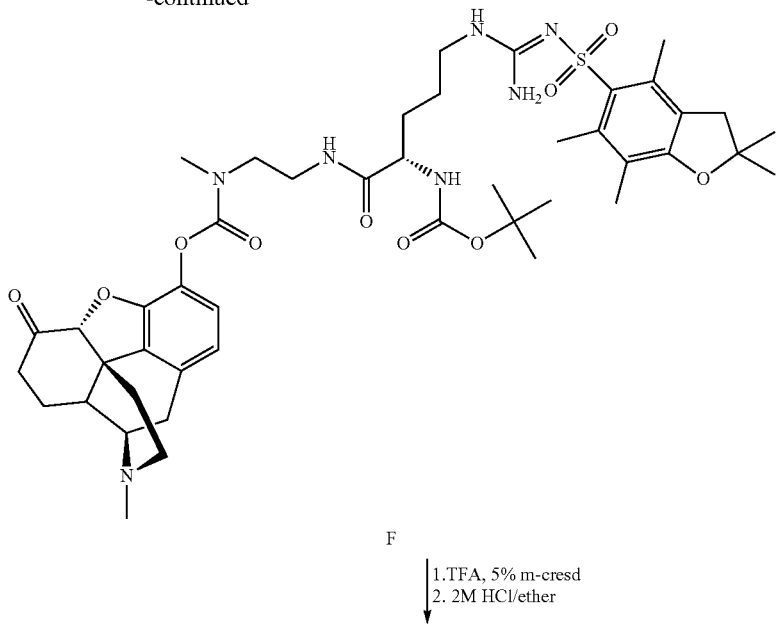

F

1. TFA, 5% m-cresd
2. 2M HCl/ether

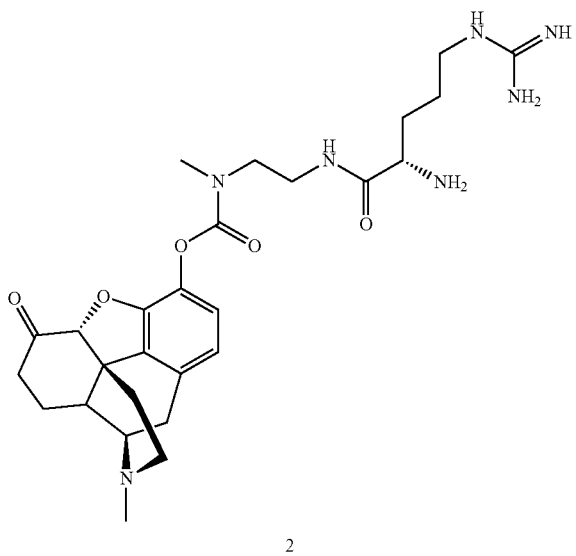

2

Preparation 1

Synthesis of 2,2,2-trifluoro-N-(2-methylamino-ethyl)-acetamide (A)

A solution of N-methylethylenediamine (27.0 g, 364.0 mmol) and ethyl trifluoroacetate (96.6 ml, 838.0 mmol) in a mixture of acetonitrile (350 ml) and water (7.8 ml, 436 mmol) was refluxed overnight with stirring. Next the solvents were evaporated in vacuo. Residue was re-evaporated with isopropanol (3×100 ml). Residue was dissolved in dichloromethane (500 ml) and left overnight at room temperature. The formed crystals were filtered, washed with dichloromethane and dried in vacuo to provide compound A (96.8 g, 94%) as white solid powder.

Preparation 2

Synthesis of {methyl-[2-(2,2,2-trifluoro-acetylamino)-ethyl]-carbamic acid benzyl ester (B)

A solution of compound A (96.8 g, 340.7 mmol) and DIEA (59.3 ml, 340.7 mmol) in THF (350 ml) was cooled to ~5° C., followed by addition of a solution of N-(benzyloxycarbonyl) succinimide (84.0 g, 337.3 mmol) in THF (150 ml) dropwise over the period of 20 min The temperature of reaction mixture was raised to room temperature and stirring was continued for an additional 30 min, followed by the solvents being evaporated. The resultant residue was dissolved in EtOAc (600 ml). EtOAc was extracted with 5% aq. $NaHCO_3$ (2×150 ml) and brine (150 ml). The organic layer was separated and evaporated to provide compound B as yellowish oil (103.0 g, 340.7 mmol). LC-MS [M+H] 305.3 ($C_{13}H_{15}F_3N_2O_3$+H, calc: 305.3). Compound B was used without further purification.

Preparation 3

Synthesis of (2-amino-ethyl)-methyl-carbamic acid benzyl ester (C)

To a solution of compound B (103.0 g, 340.7 mmol) in MeOH (1200 ml) was added a solution of LiOH (16.4 g, 681.4 mmol) in water (120 ml). The reaction mixture was stirred at room temperature for 3 h. Solvents were evaporated to ¾ of initial volume followed by dilution with water (400 ml). Solution was extracted with EtOAc (2×300 ml). The organic layer was washed with brine (200 ml), dried over $MgSO_4$ and evaporated in vacuo. The resultant residue was dissolved in ether (300 ml) and treated with 2 N HCl/ether (200 ml). The formed precipitate was filtered, washed with ether and dried in vacuo to provide hydrochloric salt of compound C (54.5 g, 261.2 mmol) as white solid. LC-MS [M+H] 209.5 ($C_{11}H_{16}N_2O_2$+H, calc: 209.3).

Preparation 4

Synthesis of {(S)-4-({amino-[(E)-2,2,4,6,7-pentamethyl-2,3-dihydro-benzofuran-5-sulfonylimino]-methyl}-amino)-1-[2-(benzyloxycarbonyl-methyl-amino)-ethyl carbamoyl]-butyl}-carbamic acid tert-butyl ester (D)

A solution of Boc-Arg(Pbf)-OH (3.33 g, 6.32 mmol), HATU (2.88 g, 7.58 mmol) and DIEA (7.4 ml, 31.6 mmol) in DMF (40 ml) was maintained at room temperature for 20 min, followed by the addition of compound C hydrochloride (1.45 g, 6.95 mmol). Stirring was continued for additional 1 h. The reaction mixture was diluted with EtOAc (500 ml) and extracted with water (3×75 ml) and brine (75 ml). The organic layer was dried over $MgSO_4$ and then evaporated to provide compound D (4.14 g, 5.77 mmol) as yellowish amorphous solid. LC-MS [M+H] 717.6 ($C_{35}H_{52}N_6O_8S$+H, calc: 717.9).

Preparation 5

Synthesis of (S)-2-amino-5-({amino-[(E)-2,2,4,6,7-pentamethyl-2,3-dihydro-benzofuran-5-sulfonylimino]-methyl}-amino)-pentanoic acid (2-methylamino-ethyl)-amide (E)

Compound D (4.14 g, 5.77 mmol) and AcOH (330 µl, 5.77 mmol) was dissolved in methanol (40 ml) followed by the addition of Pd/C (5% wt, 880 mg) suspension in water (5 ml). The reaction mixture was subjected to hydrogenation (Parr apparatus, 75 psi) at room temperature for 2.5 h. The catalyst was filtered over a pad of Celite on sintered glass funnel and washed with methanol. Filtrate was evaporated in vacuo to provide compound E (1.96 g, 3.2 mmol) as yellowish amorphous solid. LC-MS [M+H] 483.2 ($C_{22}H_{38}N_6O_4S$+H, calc: 483.2).

Preparation 6

Synthesis of {(S)-4-({amino-[(E)-2,2,4,6,7-pentamethyl-2,3-dihydro-benzofuran-5-sulfonylimino]-methyl}-amino)-1-[2-(hydromorphylcarbonyl-methyl-amino)-ethyl carbamoyl]-butyl}-carbamic acid tert-butyl ester (F)

A suspension of hydromorphone hydrochloride (332 mg, 1.03 mmol) and DIEA (179 µl, 1.03 mmol) in chloroform (4 ml) was sonicated in an ultrasonic bath at room temperature for 1 h. This was followed by the addition of 4-nitrophenyl chloroformate (162 mg, 0.80 mmol). The reaction mixture was sonicated in an ultrasonic bath at room temperature for additional 1 h, followed by the addition of solution of compound E (400 mg, 0.67 mmol) and 1-hydroxybenzo-triazole (154 mg, 1.14 mmol) in DMF (4 ml). The reaction mixture was stirred overnight (~18 h) at room temperature, followed by the solvents being evaporated in vacuo. The residue was dissolved in MeOH (5 ml) and precipitated with addition of ether (500 ml). The formed precipitate was filtered and dried in vacuo to provide compound F (520 mg, yield exceeded quantitative) as off-white solid. LC-MS [M+H] 894.6 ($C_{45}H_{63}N_7O_{10}S$+H, calc: 894.9).

Synthesis of [2-((S)-2-amino-5-guanidino-pentanoylamino)-ethyl]methyl-carbamic acid hydromorphyl ester (Compound 2)

Compound F (679 mg, 0.76 mmol) was dissolved in the mixture of 5% m-cresol/TFA (10 ml). The reaction mixture was maintained at room temperature for 1 h, followed by the dilution with ether (500 ml). Formed precipitate was filtered, washed with ether (100 ml) and dried in vacuo to provide crude compound 2 (441 mg, yield exceeded quantitative) as off-white solid. LC-MS [M+H] 542.4 ($C_{27}H_{39}N_7O_5$+H, calc: 542).

Crude compound 2 was dissolved in water (10 ml) and subjected to preparative reverse phase HPLC purification. [Nanosyn-Pack Microsorb (100-10) C-18 column (50×300 mm); flow rate=100 ml/min; injection volume 10 ml; mobile phase A: 100% water, 0.1% TFA; mobile phase B: 100% acetonitrile, 0.1% TFA; isocratic elution at 0% B in 5 min, gradient elution to 6% B in 6 min, isocratic elution at 6% B in 23 min, gradient elution from 6% B to 55% B in 66 min; detection at 254 nm]. Fractions containing the desired compound were combined and concentrated in vacuo. Residue was dissolved in i-PrOH (20 ml) and evaporated in vacuo (procedure was repeated twice). Residue was dissolved in i-PrOH (2 ml) and treated with 2 N HCl/ether (100 ml, 200 mmol) to provide the hydrochloride salt of Compound 2 (80 mg, 17% yield, 98% purity) as white solid. LC-MS [M+H] 542.0 ($C_{27}H_{39}N_7O_5$+H, calc: 542.9). Retention time*: 2.04 min

*—[Chromolith SpeedRod RP-18e C18 column (4.6×50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 12
Synthesis of (S)-2-Acetylamino-6-amino-hexanoic acid (2-methylamino-ethyl)-amide hydromorphone ester (Compound 3)
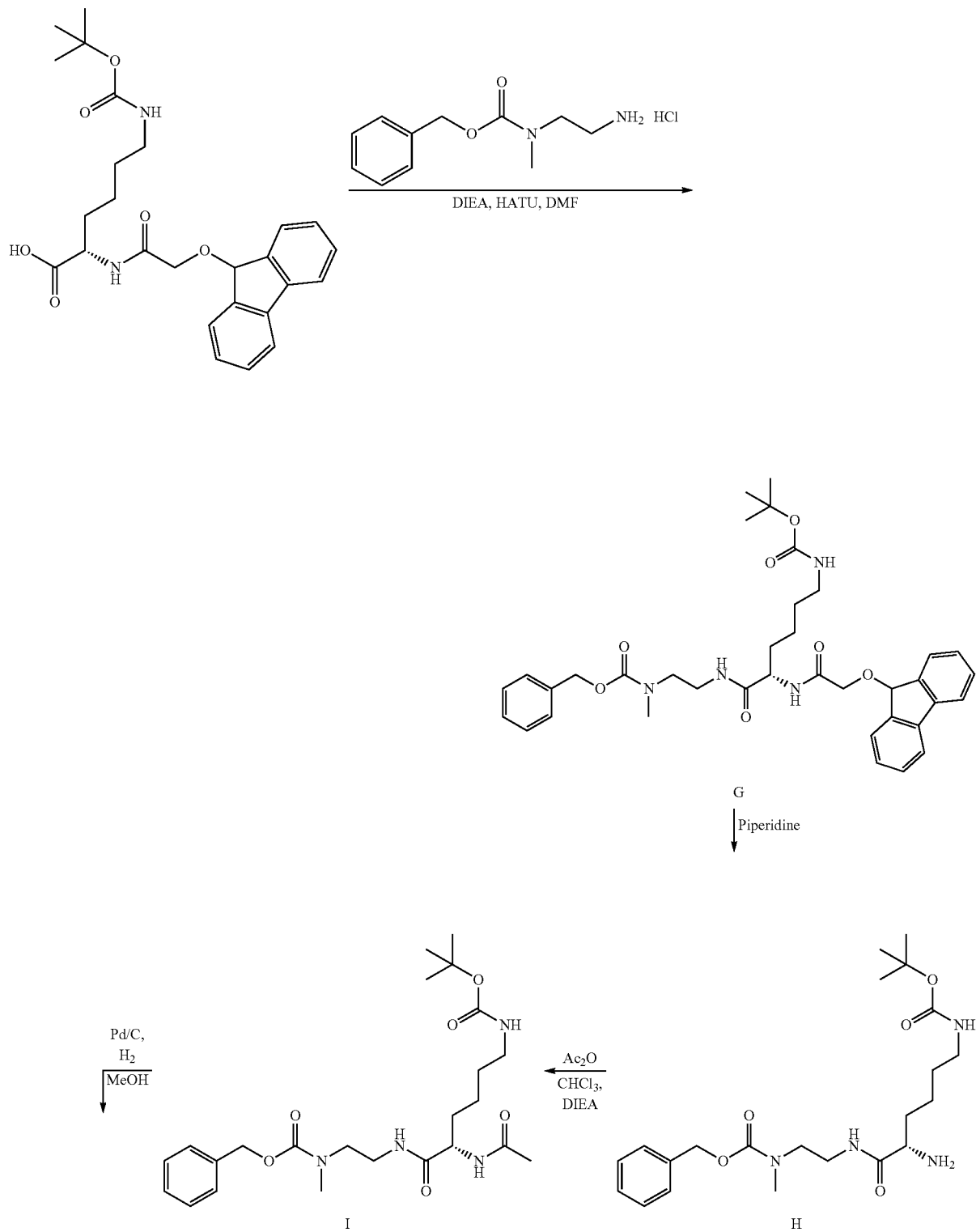

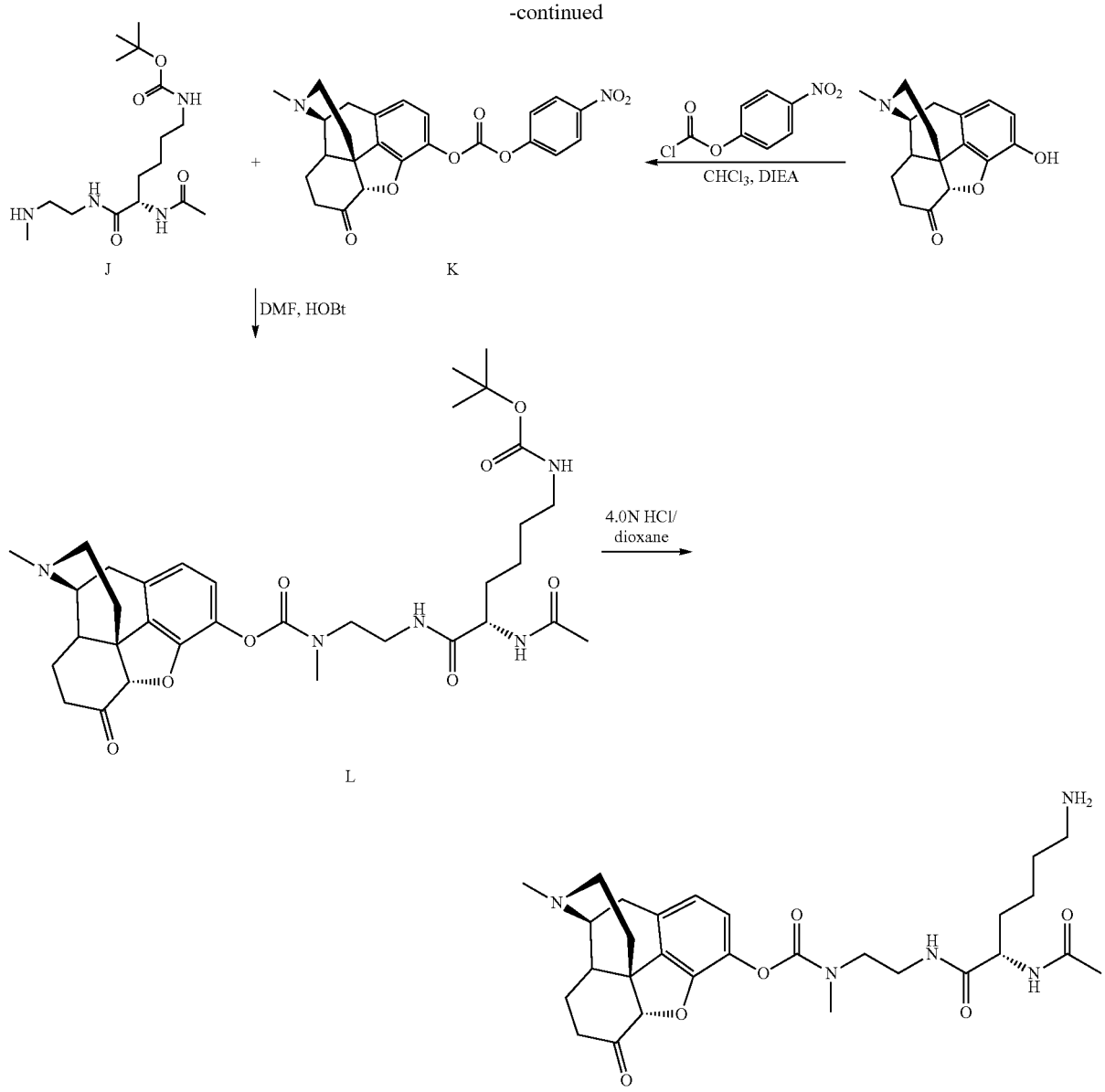

Preparation 7

Synthesis of {(S)-1-[2-(Benzyloxycarbonyl-methyl-amino)-ethylcarbamoyl]-5-tert-butoxycarbonylamino-pentyl}-carbamic acid 9H-fluoren-9-ylmethyl ester (G)

To a solution of Fmoc-Lys(Boc)-OH (2.0 g, 4.26 mmol) in DMF (50 mL) was added DIEA (2.38 mL, 13.65 mmol) and stirred for 15 min at room temperature. The reaction mixture was then cooled to ~5° C., followed by addition of HATU (1.95 g, 5.12 mmol) added in portions and stirred for 30 min The CBZ-diamine (1.05 g, 4.26 mmol) was added to the reaction mixture and stirred at room temperature for 2 h. The reaction mixture was diluted with EtOAc (250 mL), washed with water (250 mL) and brine (250 mL). The organic layer was separated, dried over $Na_2SO_4$, and removal of the solvent in vacuo afforded compound G (2.3 g, 82%). LC-MS [M+H] 659.6 ($C_{37}H_{46}N_4O_7$+H, calc: 659.7).

Preparation 8

Synthesis of {(S)-5-Amino-5-[2-(benzyloxycarbonyl-methyl-amino)-ethylcarbamoyl]-pentyl}-carbamic acid tert-butyl ester (H)

To a solution of compound G (2.3 g, 3.49 mmol) in EtOAC (50 ml) was added piperidine (0.34 mL, 3.49 mmol). The reaction mixture was stirred for 18 h at room temperature and then the solvents were removed in vacuo. The residue was dissolved in a minimum amount of EtOAc, and then was precipitated with $Et_2O$. Precipitate was filtered off and washed with $Et_2O$ and dried to afford compound H (1.4 g, 94%). LC-MS [M+H] 437.6 ($C_{22}H_{36}N_4O_5$+H, calc: 437.5).

Preparation 9

Synthesis of {(S)-5-Acetylamino-5-[2-(benzyloxy-carbonyl-methyl-amino)-ethyl carbamoyl]-pentyl}-carbamic acid isopropyl ester (I)

To a solution of compound H (1.4 g, 3.21 mmol) in CHCl$_3$ (10 mL) at room temperature was added DIEA (2.6 mL, 15 mmol) followed by Ac$_2$O (0.85 mL, 9.0 mmol). The reaction mixture was stirred at room temperature for 2 h. Solvents were removed in vacuo and then the residue was dissolved in dichloromethane (100 mL). The organic layer was washed with 10% citric acid (75 mL), saturated NaHCO$_3$ (75 mL) and brine (75 mL). The organic layer was separated, dried over Na$_2$SO$_4$ and solvent removed in vacuo to afford compound I (1.45 g, 99%). LC-MS [M+H] 479.5 ($C_{24}H_{38}N_4O_6$+H, calc: 479.5).

Preparation 10

Synthesis of [(S)-5-Acetylamino-5-(2-methylamino-ethylcarbamoyl)-pentyl]-carbamic acid tert-butyl ester (J)

To a solution of compound I (1.4 g, 3.00 mmol) in MeOH (40 mL) was added 5% Pd/C (300 mg). This reaction mixture was subjected to hydrogenation at 70 psi for 2 h. Next, the reaction mixture was filtered through a celite pad, MeOH was removed in a rotary evaporator to afford compound J (1.02 g, 98%). LC-MS [M+H] 344.9 ($C_{16}H_{32}N_4O_4$+H, calc: 345.4).

Preparation 11

[(S)-5-Acetylamino-5-(2-methylamino-ethylcarbamoyl)-pentyl]-carbamic acid tert-butyl-hydromorphone-di-ester (L)

Hydromorphone HCl salt (1.24 g, 3.86 mmol) and DIEA (0.67 mL, 3.86 mmol) were suspended in CHCl$_3$ (12 mL) and sonicated for 1 h at room temperature. 4-Nitro phenylchloroformate (600 mg, 2.97 mmol) was added to the reaction mixture and was then to sonicated for 100 min To the activated hydromorphone reaction mixture was added a solution of compound J (1.02 g, 2.97 mmol) and HOBt (0.52 g, 3.86 mmol) in DMF (12 mL) dropwise and stirred at room temperature overnight (~18 h). Solvents were then removed in vacuo and the residue was dissolved in a minimum amount of MeOH and precipitated with an excess of Et$_2$O. The precipitate was filtered off, washed with Et$_2$O and dried under vacuo to afford compound L. LC-MS [M+H]656.9 ($C_{34}H_{49}N_5O_8$+H, calc: 656.7). This crude product was purified by preparative reverse phase HPLC. [Column: VARIAN, LOAD & LOCK, L&L 4002-2 packing: Microsob 100-10 C18, Injection Volume: ~15 mL, Injection flow rate: 20 mL/min, 100% A, (water/0.1% TFA), Flow rate: 100 mL/min, Fraction: 30 Sec (50 mL) Method: 0% B (MeCN/0.1% TFA)/2 min/75% B/96 min/100 ml/min/254 nm]. Pure fractions were combined, solvents were removed in vacuo. Residue was dried via co-evaporation with i-PrOH (4×100 mL) to afford compound L as yellow oil (0.90 g, 46%).

Synthesis of (S)-2-Acetylamino-6-amino-hexanoic acid (2-methylamino-ethyl)-amide hydromorphone ester (Compound 3)

Compound L (0.90 g, 1.37 mmol) was suspended in dioxane (~2 mL), sonicated and treated with 4.0 N HO/dioxane (~20 mL) at room temperature. White precipitate was formed immediately. Next the mixture was diluted with Et$_2$O (200 mL), hexane (20 mL) and the precipitate was filtered off and washed with Et$_2$O (100 mL), hexane (100 mL) and dried under vacuum to afford Compound 3 (0.67 g, 78% yield, 97.5% purity). LC-MS [M+H] 556.3 ($C_{29}H_{41}N_5O_6$+H, calc: 556.6).

Example 13

Synthesis of [2-((S)-2-Acetylamino-5-guanidino-pentanoylamino)-ethyl]-ethyl-carbamic acid hydromorphone ester (Compound 4)

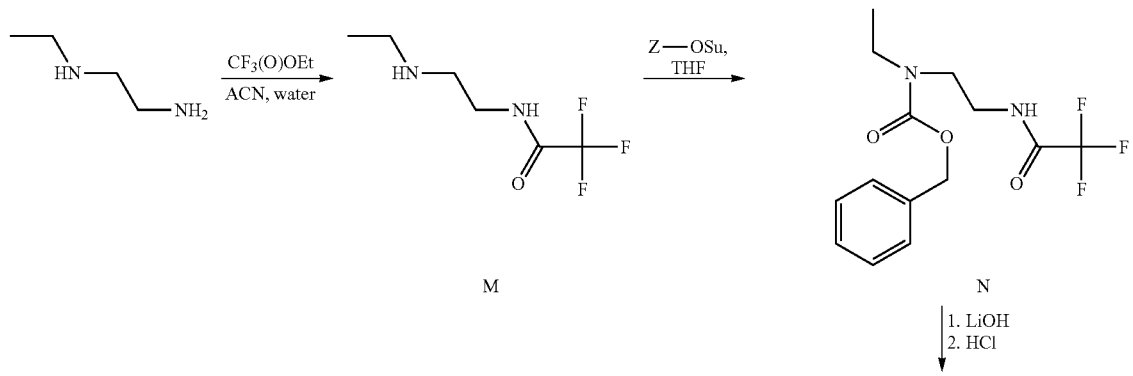

-continued
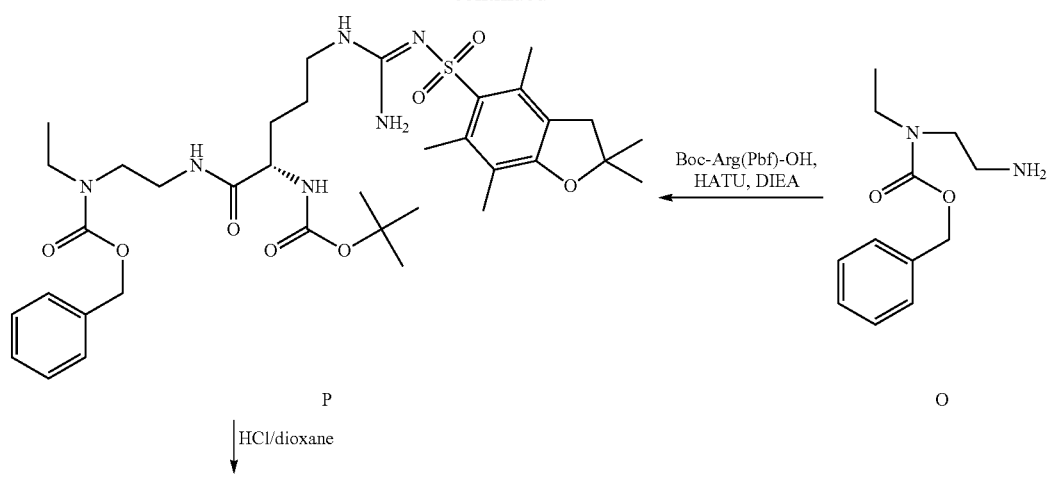
P
HCl/dioxane ↓
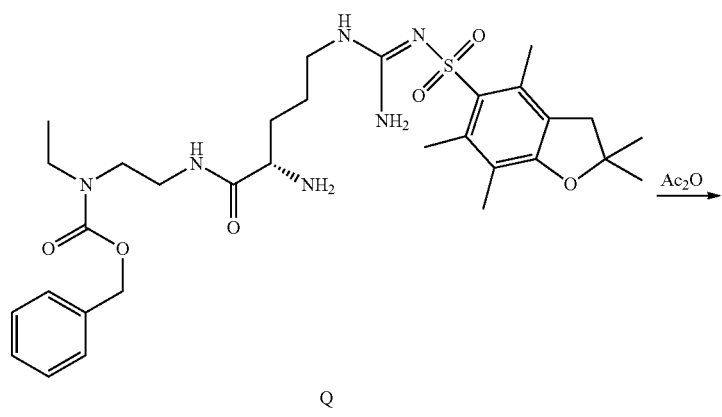
Q
Ac₂O →
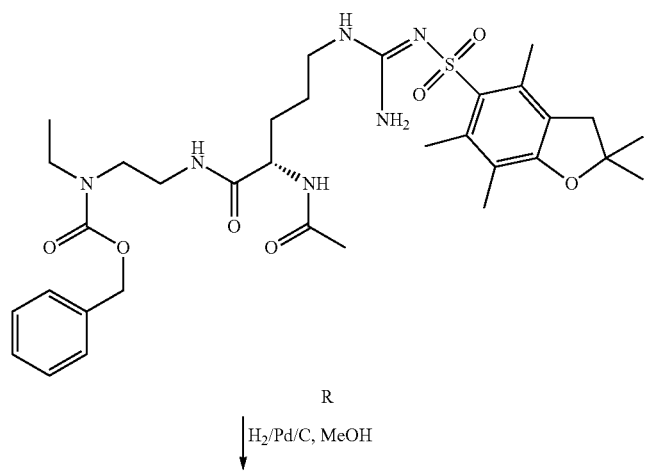
R
H₂/Pd/C, MeOH ↓

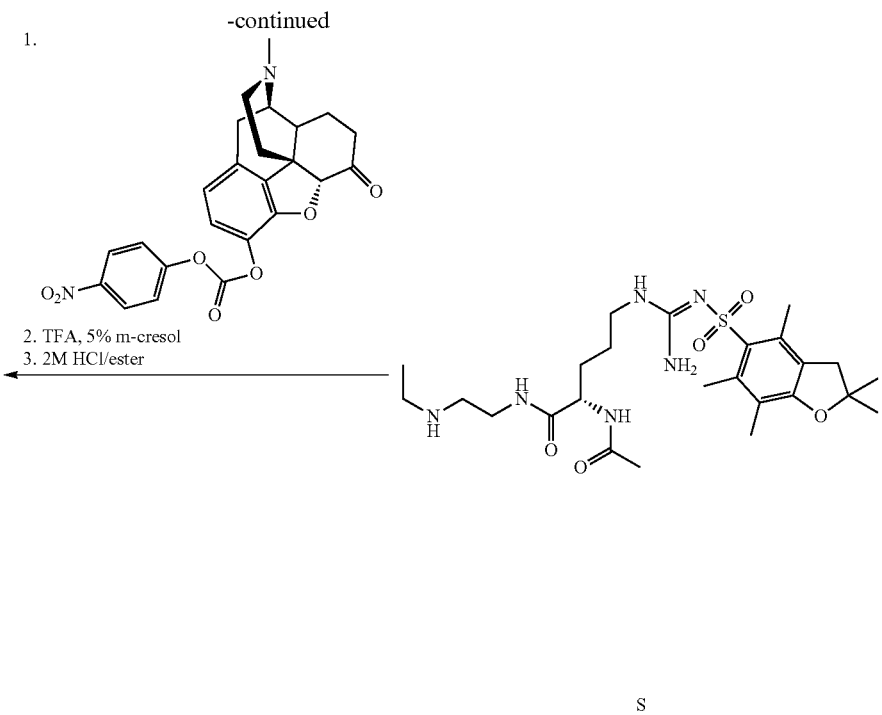

Preparation 12

Synthesis of 2,2,2-trifluoro-N-(2-ethylamino-ethyl)-acetamide (M)

A solution of N-ethylethylenediamine (10.0 g, 113.4 mmol) and ethyl trifluoroacetate (32.0 ml, 261 mmol) in the mixture of acetonitrile (110 ml) and water (2.5 ml, 139 mmol) was refluxed with stirring overnight (~18 h). Solvents were evaporated in vacuo. Residue was re-evaporated with i-PrOH (3×100 ml). Residue was dissolved in dichloromethane (500 ml) and left overnight at room temperature. The formed crystals were filtered, washed with dichloromethane (100 ml) and dried in vacuo to provide compound M (24.6 g, 82.4 mmol) as white solid powder.

Preparation 13

Synthesis of {ethyl-[2-(2,2,2-trifluoro-acetylamino)-ethyl]carbamic acid benzyl ester (N)

A solution of compound M (24.6 g, 82.4 mmol) and DIEA (14.3 ml, 82.4 mmol) in THF (100 ml) was cooled to ~5° C., followed by the addition of a solution of N-(benzyloxycarbonyl)succinimide (20.3 g, 81.6 mmol) in THF (75 ml) dropwise over 20 min The temperature of the reaction mixture was raised to room temperature and stirring was continued for an additional 30 min. Solvents were evaporated and the residue was dissolved in EtOAc (500 ml). The organic layer was extracted with 5% aqueous $NaHCO_3$ (2×100 ml) and brine (100 ml). The organic layer was evaporated to provide compound N (24.9 g, 78.2 mmol) as yellowish oil. LC-MS [M+H] 319.0 ($C_{14}H_{17}F_3N_2O_3$+H, calc: 319.2). Compound N was used without further purification.

Preparation 14

Synthesis of (2-Amino-ethyl)-ethyl-carbamic acid benzyl ester (O)

To a solution of compound N (24.9 g, 78.2 mmol) in MeOH (300 ml) was added a solution of LiOH (3.8 g, 156 mmol) in water (30 ml). The reaction mixture was stirred at room temperature for 5 h. Next the solvents were evaporated to ¾ of initial volume followed by the dilution with water (200 ml). The solution was extracted with EtOAc (200 ml×2) and the organic layer was washed with brine (100 ml), dried over $MgSO_4$ and evaporated in vacuo. Residue was dissolved in ether (200 ml) and treated with 2 N HCl/ether (200 ml). The formed precipitate was filtered, washed with ether and dried in vacuum to provide hydrochloride salt of compound O (12.1 g, 46.7 mmol) as white solid. LC-MS [M+H] 222.9 ($C_{12}H_{18}N_2O_2$+H, calc: 223.2).

Preparation 15

Synthesis of {2-[boc-Arg(Pbf)]-aminoethyl}-ethyl-carbamic acid benzyl ester (P)

A solution of Boc-Arg(Pbf)-OH (3.0 g, 5.69 mmol), compound O (1.62 g, 6.26 mmol), DIEA (3.17 ml, 18.21 mmol) and HATU (2.59 g, 6.83 mmol) in DMF (20 ml) was stirred at room temperature for 1 h. The reaction mixture was diluted with EtOAc (300 ml) and extracted with water (3×75 ml) and brine (75 ml). The organic layer was dried over $MgSO_4$, filtered and then evaporated to provide compound P (5.97 g, yield exceeded quantitative) as yellowish oil. LC-MS [M+H] 731.5 ($C_{36}H_{54}N_6O_8S$+H, calc: 731.7). Compound P was used without further purification.

Preparation 16

Synthesis of {2-[H-Arg(Pbf)]-aminoethyl}-ethyl-carbamic acid benzyl ester (Q)

Compound P (5.69 mmol) was dissolved in dioxane (20 ml) and treated with 4 N HCl/dioxane (100 ml, 70 mmol) at room temperature for 1 h. The solvent was then removed to in vacuo, followed by suspension in i-PrOH (50 ml) and finally, the solvent was evaporated to remove residual solvents (procedure was repeated twice). The crude reaction mixture was dried in vacuo to provide compound Q (5.97, yield exceeded quantitative) as yellowish solid. LC-MS [M+H] 631.5 ($C_{31}H_{46}N_6O_6S$+H, calc: 631.2). Compound Q was used without further purification.

Preparation 17

Synthesis of {2-[Ac-Arg(Pbf)]-aminoethyl}-ethyl-carbamic acid benzyl ester (R)

A solution of compound Q (5.69 mmol), Ac$_2$O (649 µl, 6.83 mmol) and DIEA (2.97 ml, 17.07 mmol) in chloroform (20 ml) was stirred at room temperature for 1 h. This was followed by addition of 2M EtNH$_2$/THF (1.71 ml, 3.41 mmol). The reaction mixture was stirred at room temperature for an additional 30 min, followed by the dilution with EtOAc (300 ml). The organic layer was extracted with water (75 ml), 2% aq. H$_2$SO$_4$ (75 ml), water (3×75 ml) and brine (75 ml). The organic layer was then dried over MgSO$_4$ and evaporated to provide compound R (3.99 g, yield exceeded quantitative) as yellowish solid. LC-MS [M+H] 673.6 (C$_{33}$H$_{48}$N$_6$O$_7$S+H, calc: 672.9). Compound R was used without further purification.

Preparation 18

Synthesis of N-[Ac-Arg(Pbf)]-N'-ethyl-ethane-1,2-diamine (S)

Compound R (5.69 mmol) was dissolved in methanol (50 ml) followed by addition of Pd/C (5% wt, 1 g) suspension in water (5 ml). Reaction mixture was subjected to hydrogenation (Parr apparatus, 80 psi) at room temperature for 1 h. Upon completion, the catalyst was filtered over pad of Celite on sintered glass funnel and washed with methanol. The filtrate was evaporated in vacuo to provide the compound S (3.06 g, quantitative yield) as colorless oil. LC-MS [M+H] 539.5 (C$_{25}$H$_{42}$N$_6$O$_5$S+H, calc: 539.9). Compound S was used without further purification.

Synthesis of [2-(2-Acetylamino-5-guanidino-pentanoylamino)-ethyl]-ethyl-carbamic acid hydromorphone ester (Compound 4)

A suspension of hydromorphone hydrochloride (2.75 g, 8.54 mmol) and DIEA (1.49 ml, 8.54 mmol) in chloroform (8 ml) was sonicated in an ultrasonic bath at room temperature for 1 h, followed by addition of 4-nitrophenyl chloroformate (1.38 g, 6.83 mmol). The reaction mixture was sonicated in an ultrasonic bath at room temperature for additional 1 h, followed by the addition of solution of compound S (3.06 g, 5.69 mmol) and 1-hydroxybenzotriazole (1.31 g, 9.67 mmol) in DMF (8 ml). The reaction mixture was stirred overnight (~18 h) at room temperature, followed by solvents being evaporated in vacuo. The crude reaction mixture was dissolved in MeOH (10 ml) and precipitated with ether (500 ml). The formed precipitate was filtered and dried in vacuo to provide Pbf protected compound 4 (6.96 g yield exceeded quantitative) as off-white solid. LC-MS [M+H] 850.6 (C$_{43}$H$_{59}$N$_7$O$_9$S+H, requires 850.2).

Pbf protected compound 4 was dissolved in a mixture of 5% m-cresol/TFA (100 ml). The reaction mixture was maintained at room temperature for 1 h, followed by dilution with ether (2 L). A precipitate was formed and subsequently filtered over sintered glass funnel, washed with ether (200 ml) and dried in vacuo to provide crude compound 4 (5.2 g, 97%) as off-white solid. Crude compound 4 (5.2 g, 5.54 mmol) was dissolved in water (50 ml) and subjected to HPLC purification. [Nanosyn-Pack Microsorb (100-10) C-18 column (50× 300 mm); flow rate=100 ml/min; injection volume 50 ml; mobile phase A: 100% water, 0.1% TFA; mobile phase B: 100% acetonitrile, 0.1% TFA; isocratic elution at 0% B in 5 min., gradient elution to 6% B in 6 min, isocratic elution at 6% B in 13 min, gradient elution from 6% B to 55% B in 76 min; detection at 254 nm]. Fractions containing the desired compound were combined and concentrated in vacuo. The residue was dissolved in i-PrOH (50 ml) and evaporated in vacuo (procedure was repeated twice). The residue was dissolved in i-PrOH (50 ml) and treated with 2 N HCl/ether (200 ml, 400 mmol) to provide hydrochloride salt of Compound 4 (1.26 g, 32% yield, 95.7% purity) as white solid. LC-MS [M+H] 598.4 (C$_{30}$H$_{43}$N$_7$O$_6$+H, calc: 598.7). Retention time*: 2.53 min

*—[Chromolith SpeedRod RP-18e C18 column (4.6×50 mm); flow rate 1.5 ml/min; mobile phase A: 0.1% TFA/water; mobile phase B 0.1% TFA/ACN; gradient elution from 5% B to 100% B over 9.6 min, detection 254 nm]

Example 14

Synthesis of (S)-ethyl 4-(5-guanidino-2-(naphthalene-2-sulfonamido)pentanoyl)piperazine-1-carboxylate (Compound 101)

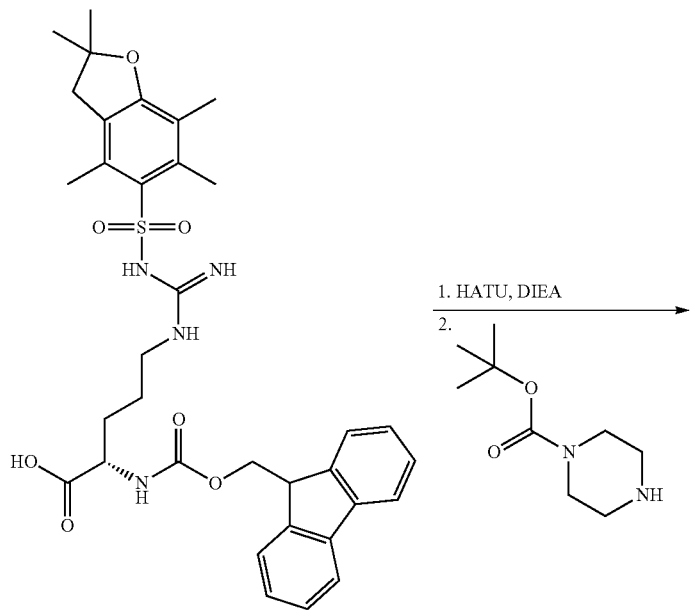

-continued
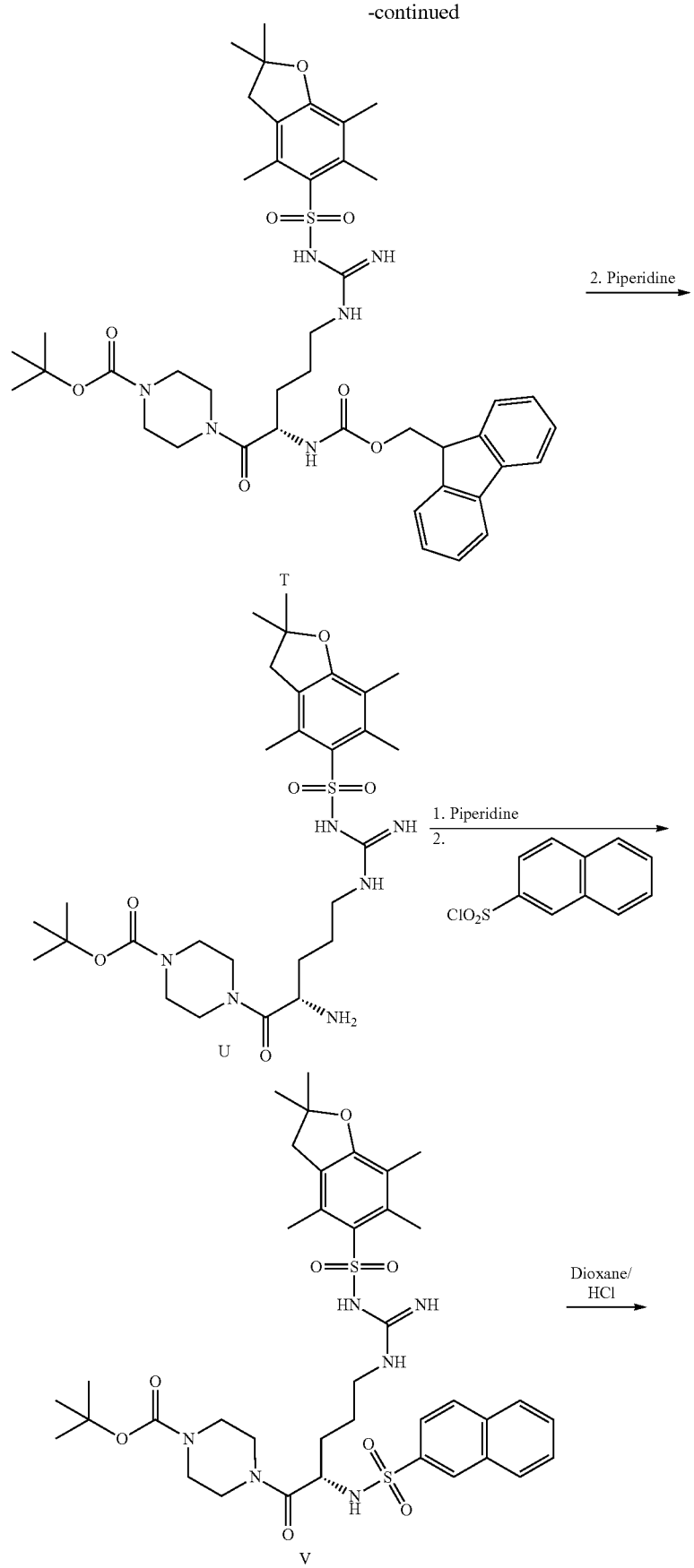

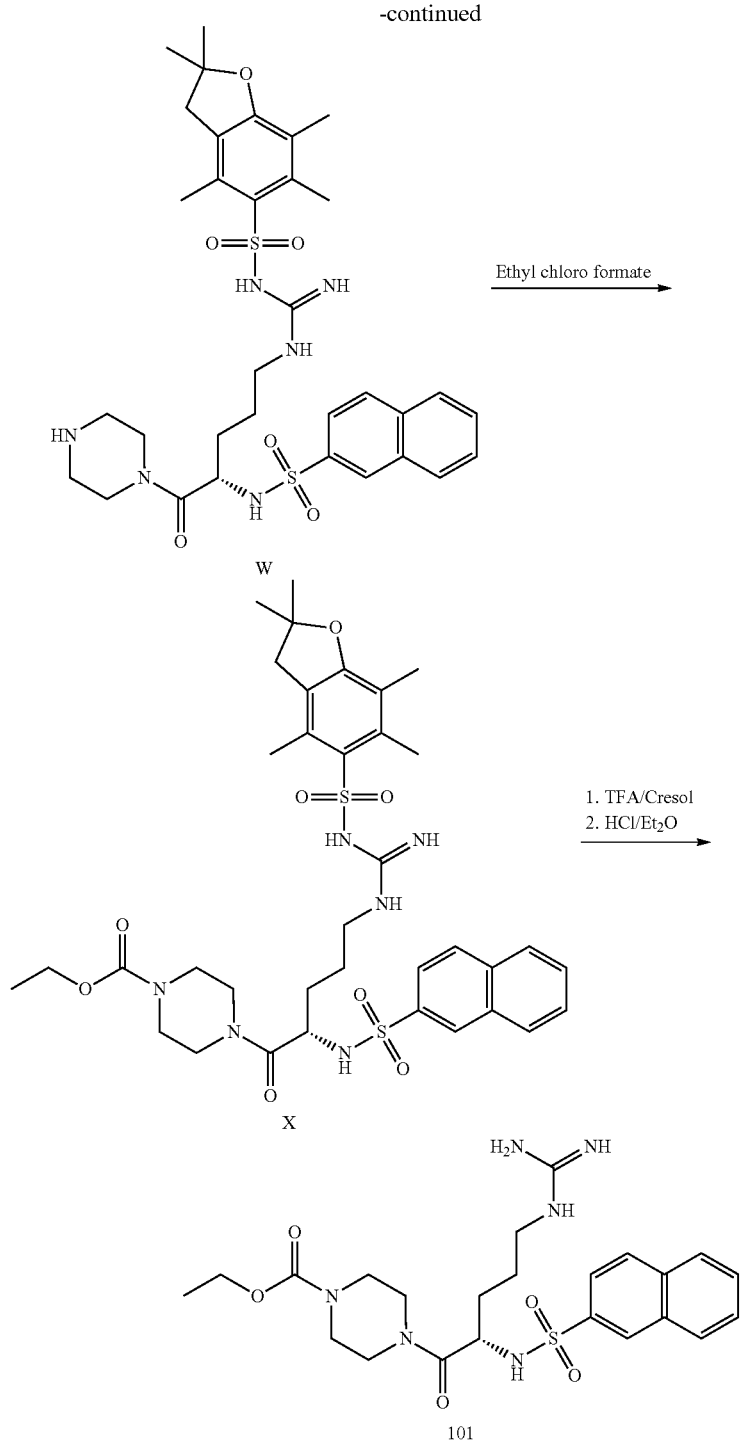

Preparation 19

Synthesis of 4-[(S)-5-({Amino-[(E)-2,2,4,6,7-pentamethyl-2,3-dihydro-benzofuran-5-sulfonylimino]-methyl}-amino)-2-(9H-fluoren-9-ylmethoxycarbonylamino)-pentanoyl]-piperazine-1-carboxylic acid tert-butyl ester (T)

To a solution of Fmoc-Arg(Pbf)-OH 1 (25.0 g, 38.5 mmol) in DMF (200 mL) at room temperature was added DIEA (13.41 mL, 77.1 mmol). After stirring at room temperature for 10 min, the reaction mixture was cooled to ~5° C. To the reaction mixture was added HATU (16.11 g, 42.4 mmol) in portions and stirred for 20 min and a solution of tert-butyl-1-piperazine carboxylate (7.18 g, 38.5 mmol) in DMF (50 mL) was added dropwise. The reaction mixture was stirred at ~5° C. for 5 min The mixture reaction was then allowed to warm to room temperature and stirred for 2 h. Solvent was removed in vacuo and the residue was dissolved in EtOAc (500 mL), washed with water (2×750 mL), 1% $H_2SO_4$ (300 mL) and brine (750 mL). The organic layer was separated, dried over Na$_2$SO$_4$ and solvent removed in vacuo to a total volume of 100 mL. Compound T was taken to the next step as EtOAc solution (100 mL). LC-MS [M+H] 817.5 (C$_{43}$H$_{56}$N$_6$O$_8$S+H, calc: 817.4).

Preparation 20

Synthesis of 4-[(S)-2-Amino-5-({amino-[(E)-2,2,4,6,7-pentamethyl-2,3-dihydro-benzofuran-5-sulfonylimino]-methyl}-amino)-pentanoyl]-piperazine-1-carboxylic acid tert-butyl ester (U)

To a solution of compound T (46.2 mmol) in EtOAc (175 mL) at room temperature was added piperidine (4.57 mL, 46.2 mmol) and the reaction mixture was stirred for 18 h at room temperature. Next the solvent was removed in vacuo and the resulting residue dissolved in minimum amount of EtOAc (~50 mL) and hexane (~1 L) was added. Precipitated crude product was filtered off and recrystallised again with EtOAc (~30 mL) and hexane (~750 mL). The precipitate was filtered off, washed with hexane and dried in vacuo to afford compound U (28.0 g, 46.2 mmol). LC-MS [M+H] 595.4 (C$_{28}$H$_{46}$N$_6$O$_6$S+H, calc: 595.3).

Preparation 21

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid tert-butyl ester (V)

To a solution of compound U (28.0 g, 46.2 mmol) in THF (250 mL) was added aqueous 1N NaOH (171 mL). The reaction mixture was cooled to ~5° C., a solution of 2-naphthalene sulfonylchloride (26.19 g, 115.6 mmol) in THF (125 mL) was added dropwise. The reaction mixture was stirred at ~5° C. for 10 min, with stirring continued at room temperature for 2 h. The reaction mixture was diluted with EtOAc (1 L), washed with aqueous 1N NaOH (1 L), water (1 L) and brine (1 L). The organic layer was separated, dried over Na$_2$SO$_4$ and removal of the solvent in vacuo to afford compound V (36.6 g, 46.2 mmol). LC-MS [M+H] 785.5 (C$_{38}$H$_{52}$N$_6$O$_8$S$_2$+H, calc: 785.9).

Preparation 22

Synthesis of 2,2,4,6,7-Pentamethyl-2,3-dihydro-benzofuran-5-sulfonic acid 1-amino-1-[(S)-4-(naphthalene-2-sulfonylamino)-5-oxo-5-piperazin-1-yl-pentylamino]-meth-(E)-ylideneamide (W)

To a solution of compound V (36.6 g, 46.2 mmol) in dioxane (60 mL) was added 4M HCl in dioxane (58 mL) dropwise. The reaction mixture was stirred at room temperature for 1.5 h. Et$_2$O (600 mL) was added to the reaction mixture, precipitated product was filtered off, washed with Et$_2$O and finally dried under vacuum to afford compound W (34.5 g, 46.2 mmol). LC-MS [M+H]685.4 (C$_{33}$H$_{44}$N$_6$O$_6$S$_2$+H, calc: 685.9). Compound W was used without further purification.

Preparation 23

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid ethyl ester (X)

To a solution of compound W (8.0 g, 11.1 mmol) in CHCl$_3$ (50 ml) was added DIEA (4.1 mL, 23.3 mmol) at room temperature and stirred for 15 min. The mixture was cooled to ~5° C., ethyl chloroformate (1.06 mL, 11.1 mmol) was added drop wise. After stirring at room temperature overnight (~18 h), solvent removed in vacuo. The residue was dissolved in MeOH (~25 ml) and Et2O (~500 mL) was added. The precipitated crude product was filtered off, washed with Et2O and dried under vacuo to afford compound X (8.5 g, 11.1 mmol). LC-MS [M+H]757.6 (C$_{36}$H$_{48}$N$_6$O$_8$S$_2$+H, calc: 757.9). Compound X was used without further purification.

Synthesis of (S)-ethyl 4-(5-guanidino-2-(naphthalene-2-sulfonamido)pentanoyl)piperazine-1-carboxylate (Compound 101)

A solution of 5% m-cresol/TFA (50 ml) was added to compound X (8.5 g, 11.1 mmol) at room temperature. After stirring for 1 h, the reaction mixture was precipitated with Et$_2$O (~500 mL). The precipitate was filtered and washed with Et$_2$O and dried under vacuo to afford the crude product. The crude product was purified by preparative reverse phase HPLC. [Column: VARIAN, LOAD & LOCK, L&L 4002-2, Packing: Microsob 100-10 C18, Injection, Volume: ~15 mL×2, Injection flow rate: 20 mL/min, 100% A, (water/0.1% TFA), Flow rate: 100 mL/min, Fraction: 30 Sec (50 mL), Method: 0% B (MeCN/0.1% TFA)-60% B/60 min/100 ml/min/254 nm]. Solvents were removed from pure fractions in vacuo. Trace of water was removed by co-evaporation with 2×i-PrOH (50 ml). The residue was dissolved in a minimum amount of i-PrOH and product was precipitated with 2 M HCl in Et$_2$O. Product was filtered off and washed with Et$_2$O and dried under vacuo to afford Compound 101 as HCl salt 7 (3.78 g, 63% yield, 99.4% purity). LC-MS [M+H] 505.4 (C$_{38}$H$_{52}$N$_6$O$_8$S$_2$+H, calc: 505.6).

Example 15

Synthesis of (S)-ethyl 4-(5-guanidino-2-(2,4,6-triisopropylphenylsulfonamido)pentanoyl)piperazine-1-carboxylate (Compound 102)

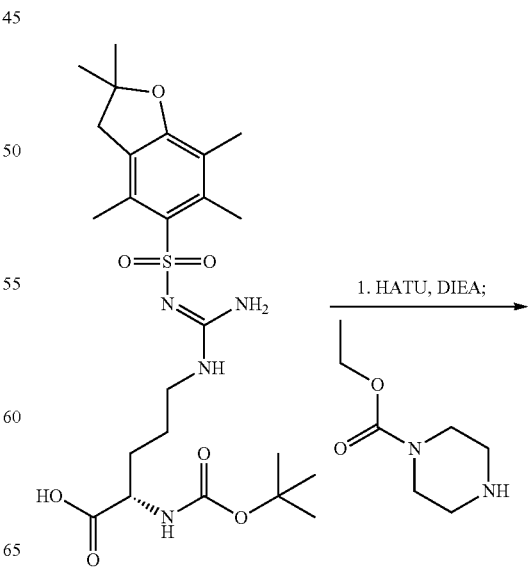

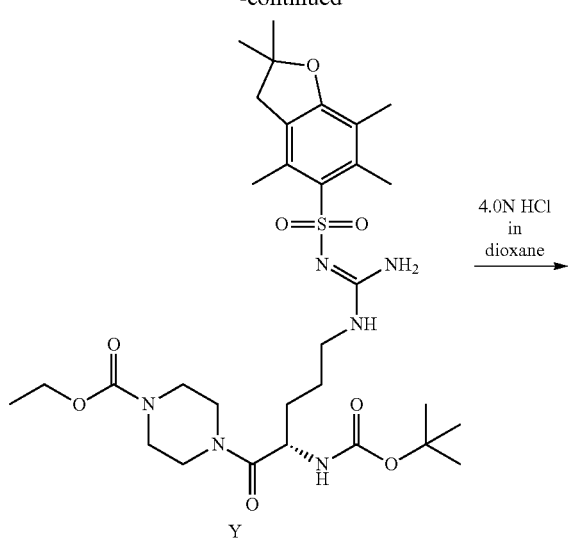

Y

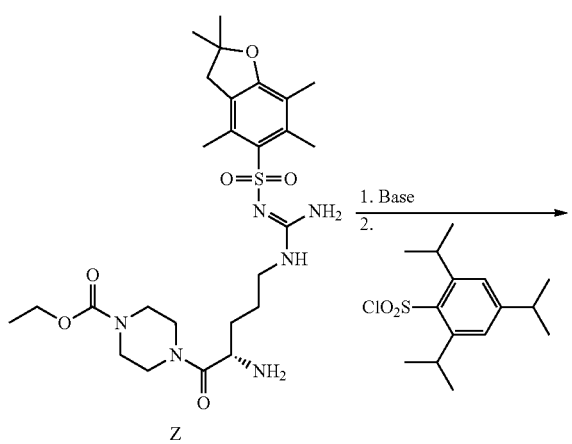

Z

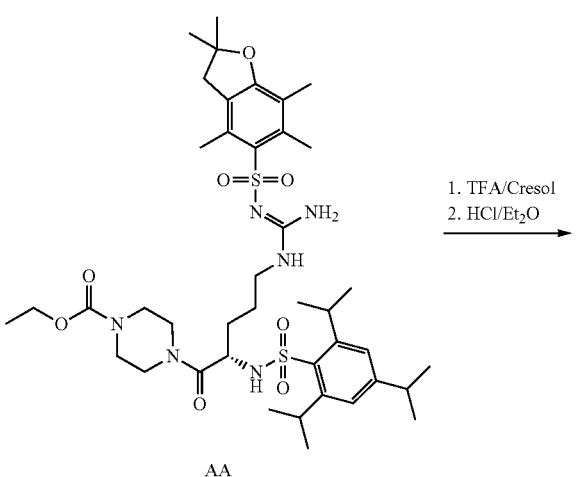

AA

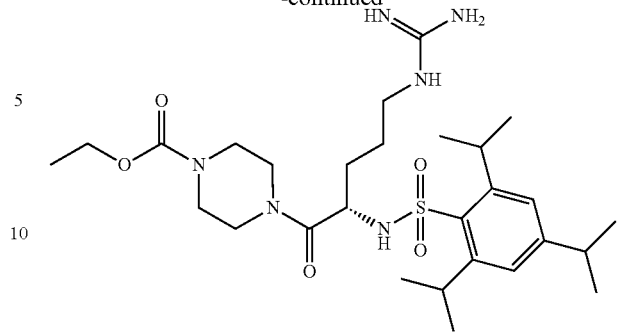

102

Preparation 24

Synthesis of 4-[(S)-5-({Amino-[(E)-2,2,4,6,7-pentamethyl-2,3-dihydro-benzofuran-5-sulfonylimino]-methyl}-amino)-2-tert-butoxycarbonylamino-pentanoyl]-piperazine-1-carboxylic acid ethyl ester (Y)

To a solution of Boc-Arg(Pbf)-OH (13.3 g, 25.3 mmol) in DMF (10 mL) was added DIEA (22.0 mL, 126.5 mmol) at room temperature and stirred for 15 min The reaction mixture was then cooled to ~5° C. and HATU (11.5 g, 30.3 mmol) was added in portions and stirred for 30 min, followed by the dropwise addition of ethyl-1-piperazine carboxylate (4.0 g, 25.3 mmol) in DMF (30 mL). After 40 min, the reaction mixture was diluted with EtOAc (400 mL) and poured in to $H_2O$ (1 L). Extracted with EtOAc (2×400 mL) and washed with $H_2O$ (800 mL), 2% $H_2SO_4$ (500 mL), $H_2O$ (2×800 mL) and brine (800 mL). Organic layer was separated, dried over $MgSO_4$ and solvent removed in vacuo. The resultant oily residue was dried in vacuo to afford compound Y (16.4 g, 24.5 mmol) as foamy solid. LC-MS [M+H] 667.2 ($C_{31}H_{50}N_6O_8S$+H, calc: 667.8). Compound Y was used without further purification.

Preparation 25

Synthesis of 4-[(S)-2-Amino-5-([({amino-[(E)-2,2,4,6,7-pentamethyl-2,3-dihydro-benzofuran-5-sulfonylimino]-methyl}-amino)-pentanoyl]-piperazine-1-carboxylic acid ethyl ester (Z)

A solution of compound Y (20.2 g, 30.2 mmol) in dichloromethane (90 mL) was treated with 4.0 N HCl in 1,4-dioxane (90 mL, 363.3 mmol) and stirred at room temperature for 2 h. Next most of the dichloromethane was removed in vacuo and $Et_2O$ (~1 L) was added. The resultant precipitate was filtered off and washed with $Et_2O$ and dried in vacuo to afford compound Z (17.8 g, 30.2 mmol). LC-MS [M+H] 567.8 ($C_{26}H_{42}N_6O_6S$+H, calc: 567.8).

Preparation 26

Synthesis of 4-[(S)-5-({Amino-[(E)-2,2,4,6,7-pentamethyl-2,3-dihydro-benzofuran-5-sulfonylimino]-methyl}-amino)-2-(2,4,6-triisopropyl-benzenesulfonylamino)-pentanoyl]-piperazine-1-carboxylic acid ethyl ester (AA)

To a solution of compound Z (1.0 g, 1.8 mmol) in THF (7 mL) was added 3.1N aqueous NaOH (4.0 mL) and stirred for 5 min. The reaction mixture was cooled to ~5° C., and then a solution of tripsyl chloride added drop wise (2.2 g, 7.3 mmol) in THF (5 mL) and stirred at room temperature overnight (~18 h). The reaction mixture was diluted with $H_2O$ (130 mL), acidified with 2% $H_2SO_4$ (15 mL) and extracted with EtOAc (3×80 mL). Organic layer were combined and washed with H₂O (2×400 mL), saturated NaHCO₃ (100 mL), H₂O (200 mL) and brine (200 mL). The organic layer was separated dried over MgSO₄ and solvent removed in vacuo to afford (2.9 g) of crude product. This was purified by normal phase flash chromatography (5-10% MeOH/DCM) to afford compound AA (0.52 g, 1.0 mmol). LC-MS [M+H] 833.8 ($C_{41}H_{64}N_6O_8S_2$+H, calc: 834.1).

Synthesis of (S)-ethyl 4-(5-guanidino-2-(2,4,6-triiso-propylphenylsulfonamido)pentanoyl)piperazine-1-carboxylate (Compound 102)

A solution of 5% m-cresol/TFA (40 ml) was added to compound AA (3.73 g, 3.32 mmol) at room temperature. After stirring for 45 min, solvents were removed in vacuo. Residue was dissolved in dichloromethane (100 ml), washed with H₂O (3×200 mL) and brine (200 mL). The organic layer was separated, dried over MgSO₄ and then the solvent removed in vacuo. The residue was dissolved in dichloromethane (~5 mL) and then hexane (~250 mL) was added and a precipitate was formed. This was washed with hexane and dried under vacuo to afford the crude product (1.95 g). The crude product was purified by reverse phase HPLC [Column: VARIAN, LOAD & LOCK, L&L 4002-2, Packing: Microsob 100-10 C18, Injection Volume: ~15 mL, Injection flow rate: 20 mL/min, 100% A, (water/0.1% TFA), Flow rate: 100 mL/min, Fraction: 30 Sec (50 mL), Method: 25% B (MeCN/0.1% TFA)/70% B/98 min/100 ml/min/254 nm]. Solvents were removed from pure fractions in to vacuo. Trace of water was removed by co-evaporation with 2×i-PrOH (50 ml). The residue was dissolved in a minimum amount of i-PrOH and product was precipitated with 2 M HCl in Et₂O. Product was filtered off and washed with Et₂O and dried under vacuo to afford the product as HCl salt of Compound 102 (0.72 g, 35% yield, 99.8% purity). LC-MS [M+H] 581.6 ($C_{28}H_{48}N_6O_5S$+H, calc: 581.7).

Example 16

Synthesis of (S)-ethyl 1-(5-guanidino-2-(naphthalene-2-sulfonamido)pentanoyl)piperidine-4-carboxylate HCl salt (Compound 103)

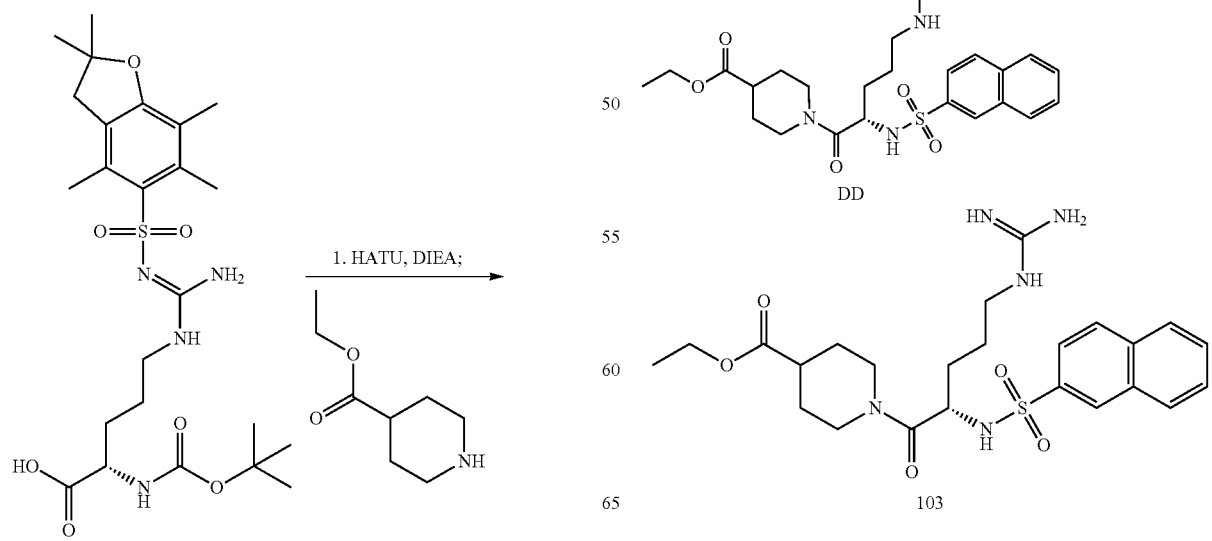

Preparation 27

Synthesis of 1-[boc-Arg(Pbf)]-piperidine-4-carboxylic acid ethyl ester (BB)

To a solution of Boc-Arg(Pbf)-OH (3.4 g, 6.36 mmol) and HATU (2.9 g, 7.63 mmol) in DMF (15 mL) was added DIEA (7.4 mL, 42.4 mmol) and the reaction mixture was stirred for 10 min at room temperature. A solution of ethyl isonipecotate (1.0 g, 6.36 mmol) in DMF (6 mL) was added to the reaction mixture dropwise. The reaction mixture was stirred at room temperature for 1 h, then diluted with ethyl acetate (150 mL) and poured into water (500 mL). The product was extracted with ethyl acetate (2×100 mL). Organic layer was washed with aqueous 0.1 N HCl (200 mL), 2% aqueous sodium bicarbonate (200 mL), water (200 mL) and brine (200 mL). The organic layer was dried over sodium sulfate, filtered, and then evaporated in vacuo. The resultant oily product was dried in vacuo overnight to give compound BB (3.7 g, 5.57 mmol) as a viscous solid. LC-MS [M+H] 666.5 ($C_{32}H_{51}N_5O_8S$+H, calc: 666.7). Compound BB was used without further purification.

Preparation 28

Synthesis of 1-[Arg(Pbf)]-piperidine-4-carboxylic acid ethyl ester HCl salt (CC)

To a solution of compound BB (4.7 g, 7.07 mmol) in dichloromethane (25 mL) was added 4N HCl in dioxane (25.0 mL, 84.84 mmol), and the reaction mixture was stirred at room temperature for 2 h. The reaction mixture was concentrated in vacuo to ~20 mL of solvent, and then diluted with diethyl ether (250 mL) to produce a white fine precipitate. The reaction mixture was stirred for 1 h and the solid was washed with ether (50 mL) and dried in a high vacuum overnight to give compound CC (4.3 g, 7.07 mmol) as a fine powder. LC-MS [M+H] 566.5 ($C_{27}H_{43}N_5O_6S$+H, calc: 566.7).

Preparation 29

Synthesis of 1-[5(S)—(N'-Pbf-guanidino)-2-(naphthalene-2-sulfonylamino)-pentanoyl]-piperidine-4-carboxylic acid ethyl ester (DD)

To a solution of compound CC (1.1 g, 1.6 mmol) and NaOH (260 mg, 5.9 mmol) in a mixture of THF (5 mL) and water (3 mL) was added a solution of 2-naphthalosulfonyl chloride (0.91 g, 2.5 mmol) in THF (10 mL) dropwise with stirring at ~5° C. The reaction mixture was stirred at room temperature for 1 h, then diluted with water (5 mL). Aqueous 1N HCl (5 mL) was added to obtain pH ~3. Additional water was added (20 mL), and the product was extracted with ethyl acetate (3×50 mL). The organic layer was removed and then washed with 2% aqueous sodium bicarbonate (50 mL), water (50 mL) and brine (50 mL). The extract was dried over anhydrous sodium sulfate, filtered, and was evaporated in vacuo. The formed oily product was dried in vacuo overnight to give compound DD (1.3 g, 1.6 mmol) as an oily foaming solid. LC-MS [M+H] 756.5 ($C_{37}H_{49}N_5O_8S_2$+H, calc: 756.7).

Synthesis of (S)-ethyl 1-(5-guanidino-2-(naphthalene-2-sulfonamido)pentanoyl)piperidine-4-carboxylate HCl salt (Compound 103)

To a flask, was added compound DD (1.3 g, 1.6 mmol) and then treated with 5% m-cresol/TFA (10 mL). The reaction mixture was stirred at room temperature for 1 h. Next, the reaction mixture was concentrated in vacuo to a volume 5 mL. Diethyl ether (200 mL) was then added to the residue, and formed fine white precipitate. The precipitate was filtered off and washed with ether (2×25 mL). The resultant solid was dried in vacuo overnight to give a crude material, which was purified by preparative reverse phase HPLC. [Nanosyn-Pack Microsorb (100-10) C-18 column (50×300 mm); flow rate=100 ml/min; injection volume 12 ml (DMSO-water, 1:1, v/v); mobile phase A: 100% water, 0.1% TFA; mobile phase B: 100% ACN, 0.1% TFA; gradient elution from 25% B to 55% B in 90 min, detection at 254 nm]. Fractions containing desired compound were combined and concentrated in vacuo. The residue was dissolved in i-PrOH (50 ml) and evaporated in vacuum (repeated twice). The residue was next dissolved in i-PrOH (5 ml) and treated with 2 N HCl/ether (100 ml, 200 mmol) to give a white precipitate. It was dried in vacuo overnight to give Compound 103 (306 mg, 31% yield, 95.7% purity) as a white solid. LC-MS [M+H] 504.5 ($C_{24}H_{33}N_5O_5S$+H, calc: 504.6).

Example 17

Synthesis of (S)-ethyl 1-(5-guanidino-2-(2,4,6-triisopropylphenylsulfonamido)pentanoyl)piperidine-4-carboxylate HCl salt (Compound 104)

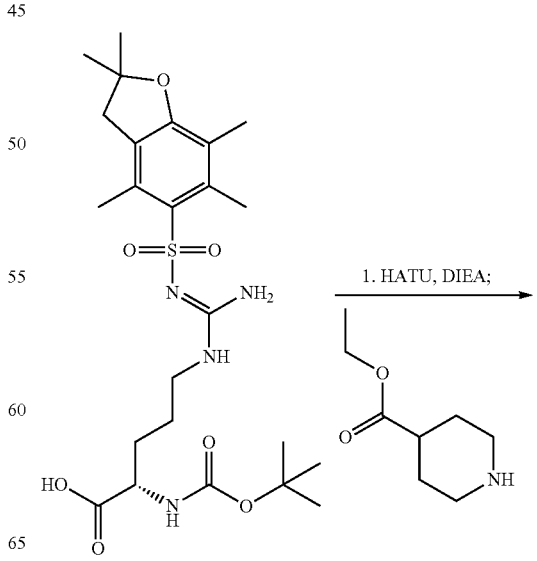

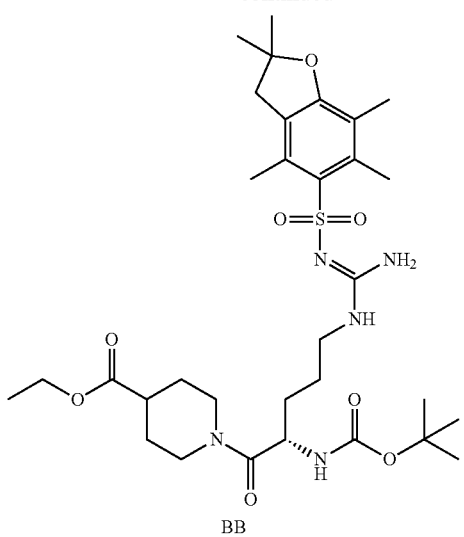

BB

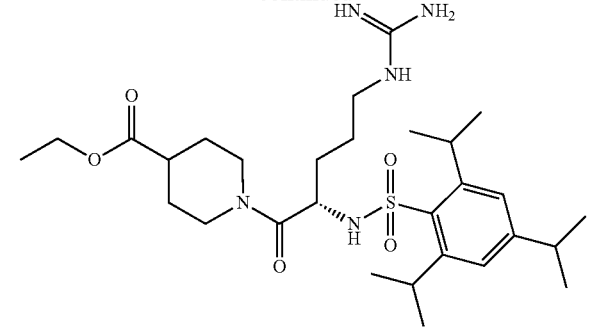

104

Preparation 30

Synthesis of 1-[5(S)—(N'-Pbf-guanidino)-2-(2,4,6-triisopropyl-benzenesulfonylamino)-pentanoyl]-piperidine-4-carboxylic acid ethyl ester (EE)

To a solution of compound CC (1.0 g, 1.6 mmol) and NaOH (420.0 mg, 10.4 mmol) in a mixture of THF (5 mL) and water (4 mL) was added a solution of 2,4,6-triisopropyl-benzenesulfonyl chloride (2.4 g, 8.0 mmol) drop wise with stirring and maintained at ~5° C. The reaction mixture was then stirred at room temperature for 1 h, monitoring the reaction progress, then diluted with water (20 mL), and acidified with aqueous 1 N HCl (5 mL) to pH ~3. Additional water was added (30 mL), and the product was extracted with ethyl acetate (3×50 mL). The organic layer was washed with 2% aqueous sodium bicarbonate (50 mL), water (50 mL) and brine (50 mL). The organic layer was dried over anhydrous sodium sulfate, filtered, and was evaporated in vacuo. Formed oily residue was dried in a vacuo overnight to give compound EE (1.0 g, 1.2 mmol) as an oily material. LC-MS [M+H] 832.8 ($C_{42}H_{65}N_5O_8S_2$+H, calc: 832.7).

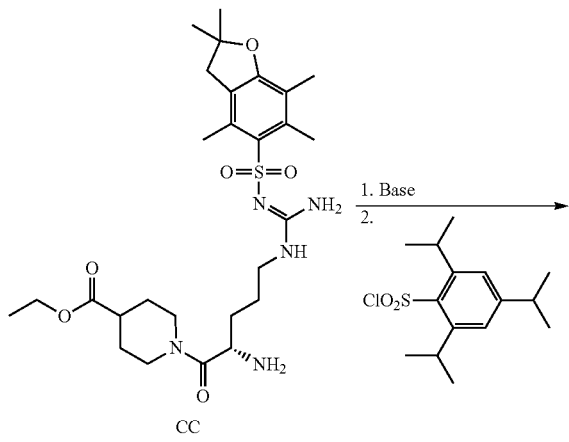
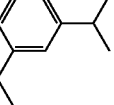

CC

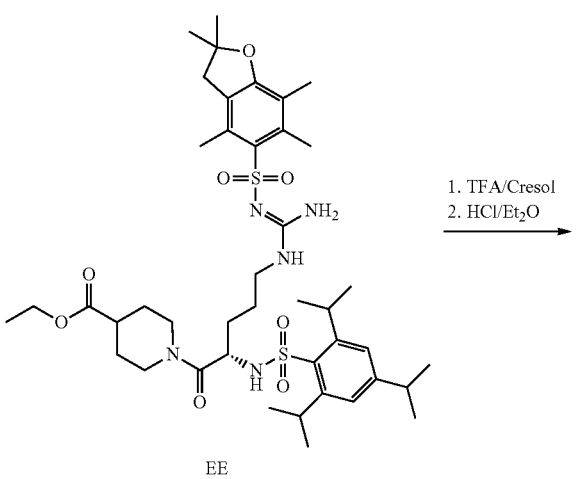

EE

Synthesis of (S)-ethyl 1-(5-guanidino-2-(2,4,6-triisopropylphenylsulfonamido)pentanoyl)piperidine-4-carboxylate HCl salt (Compound 104)

To a flask was added compound EE (2.3 g, 2.8 mmol) and then treated with 5% m-cresol/TFA (16 mL). The reaction mixture was stirred at room temperature for 1 h. The reaction mixture was then concentrated in vacuo to a volume of 5 mL. Hexane (200 mL) was added to the residue and decanted off to give an oily precipitate. The product was purified by preparative reverse phase HPLC. [Nanosyn-Pack Microsorb (100-10) C-18 column (50×300 mm); flow rate=100 ml/min; injection volume 15 ml (DMSO-water, 1:1, v/v); mobile phase A: 100% water, 0.1% TFA; mobile phase B: 100% ACN, 0.1% TFA; gradient elution from 35% B to 70% B in 90 min, detection at 254 nm]. Fractions containing desired compound were combined and concentrated in vacuo. The residue was dissolved in i-PrOH (100 ml) and evaporated in vacuo (repeated twice). The residue was dissolved in i-PrOH (5 ml) and treated with 2 N HCl/ether (100 ml, 200 mmol) to give an oily residue. It was dried in vacuo overnight to give Compound 104 (1.08 g, 62.8%) as a viscous solid. LC-MS [M+H] 580.6 ($C_{29}H_{49}N_5O_5S$+H, calc: 580.8).

Example 18
Synthesis of (S)-6-(4-(5-guanidino-2-(naphthalene-2-sulfonamido)pentanoyl)piperazin-1-yl)-6-oxohexanoic acid (Compound 105)
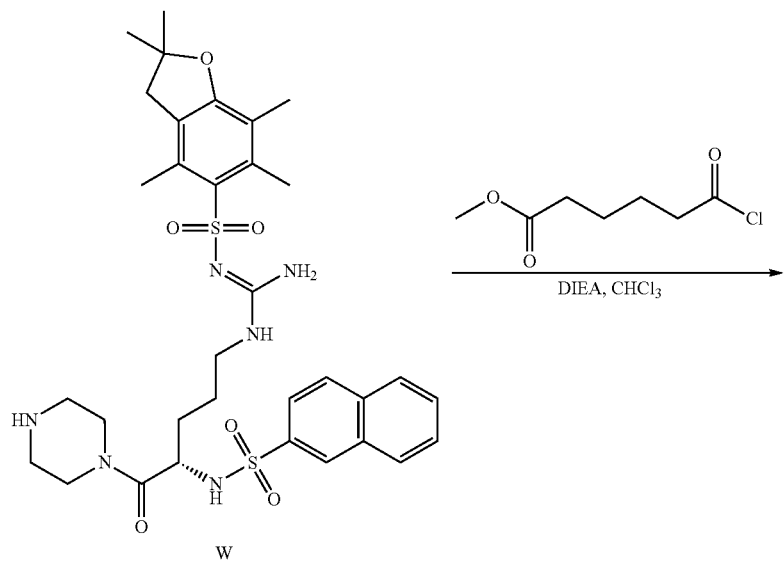
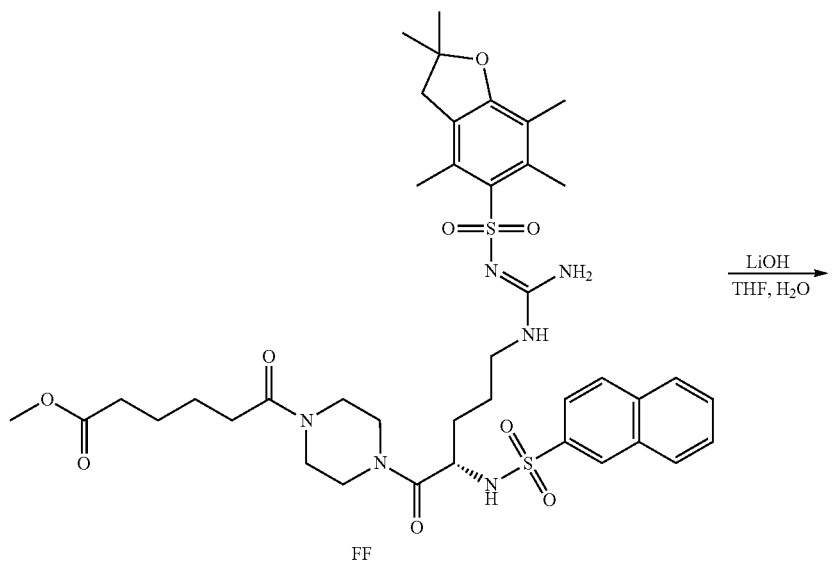

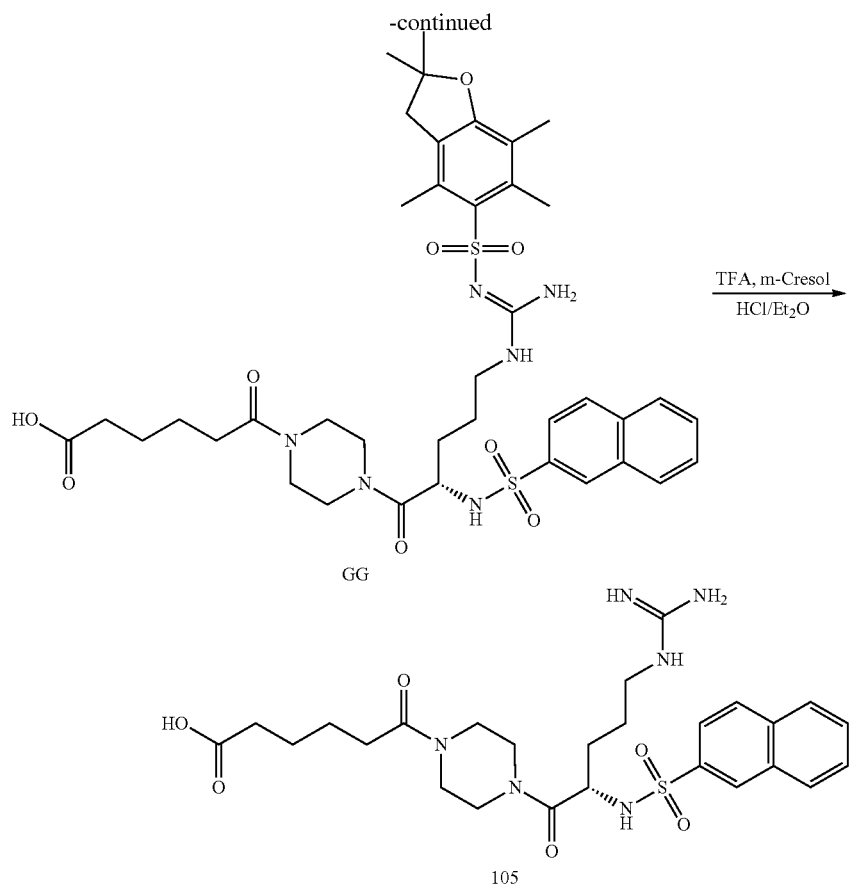

Preparation 31

Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxohexanoic acid methyl ester (FF)

To a solution of compound W (1.5 g, 2.08 mmol) in CHCl$_3$ (50 mL) was added DIEA (1.21 mL, 4.16 mmol) followed by adipoyl chloride (0.83 mL, 6.93 mmol) dropwise. The reaction mixture was stirred at room temperature overnight (~18 h). Solvents were removed in to vacuo and the residue was dried under vacuo to afford the compound FF (2.1 g, amount exceeds quantitative). LC-MS [M+H] 827.5 (C$_{40}$H$_{54}$N$_6$O$_9$S$_2$+H, calc: 827.3). Compound FF was used without further purification.

Preparation 32

Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxohexanoic acid (GG)

To a solution of compound FF (2.1 g, 2.08 mmol) in THF (5 mL), H$_2$O (5 mL) was added 2 M aq LiOH (6 mL). The reaction mixture was stirred at room temperature for 2 h. Solvents were removed in vacuo, then the residue was dissolved in water (~50 mL), acidified with saturated aqueous NaHSO$_4$ (~100 ml) and extracted with EtOAc (2×100 ml). The organic layer was dried over Na$_2$SO$_4$ and removal of the solvent gave compound GG (1.72 g, 2.08 mmol). LC-MS [M+H] 813.5 (C$_{39}$H$_{52}$N$_6$O$_9$S$_2$+H, calc: 813.3). Compound GG was used without further purification.

Synthesis of (S)-6-(4-(5-guanidino-2-(naphthalene-2-sulfonamido)pentanoyl)piperazin-1-yl)-6-oxohexanoic acid (Compound 105)

A solution of 5% m-cresol/TFA (25 ml) was added to compound GG (1.72 g, 2.08 mmol) at room temperature. After stirring for 30 min, the reaction mixture was precipitated with addition of Et$_2$O (~200 mL). The precipitate was filtered and washed with Et$_2$O and to dried under vacuo to afford the crude product. The crude product was purified by preparative reverse phase HPLC [Column: VARIAN, LOAD & LOCK, L&L 4002-2, Packing: Microsob 100-10 C18, Injection Volume: ~25 mL, Injection flow rate: 20 mL/min, 95% A, (water/0.1% TFA), Flow rate: 100 mL/min, Fraction: 30 Sec (50 mL), Method: 5% B (MeCN/0.1% TFA)/5 min/25% B/20 min/25% B/15 min/50% B/25 min/100 ml/min/254 nm]. Solvents were removed from pure fractions in vacuo. Trace of water was removed by co-evaporation with i-PrOH (25 ml) (repeated twice). The residue was dissolved in a minimum amount of i-PrOH, then 2 M HCl in Et$_2$O (~50 mL) was added and diluted with Et$_2$O (~250 mL). Precipitate formed was filtered off and washed with Et$_2$O and dried under vacuo to afford the product as HCl salt Compound 105 (0.74 g, 59% yield, 98.9% purity). LC-MS [M+H] 561.4 (C$_{26}$H$_{36}$N$_6$O$_6$S+H, calc: 561.2).

Example 19

Synthesis of 3-(4-carbamimidoylphenyl)-2-oxopropanoic acid (Compound 107)

Compound 107, i.e., 3-(4-carbamimidoylphenyl)-2-oxo-propanoic acid can be produced using methods known to those skilled in the art, such as that described by Richter P et al, Pharmazie, 1977, 32, 216-220 and references contained within. The purity of Compound 107 used in Example 7 was estimated to be 76%, an estimate due low UV absorbance of this compound via HPLC. Mass spec data: LC-MS [M+H] 207.0 (C10H10N2O3+H, calc: 207.1).

Example 20

Synthesis of (S)-5-(4-carbamimidoylbenzylamino)-5-oxo-4-((R)-4-phenyl-2-(phenylmethylsulfonamido)butanamido)pentanoic acid (Compound 108)

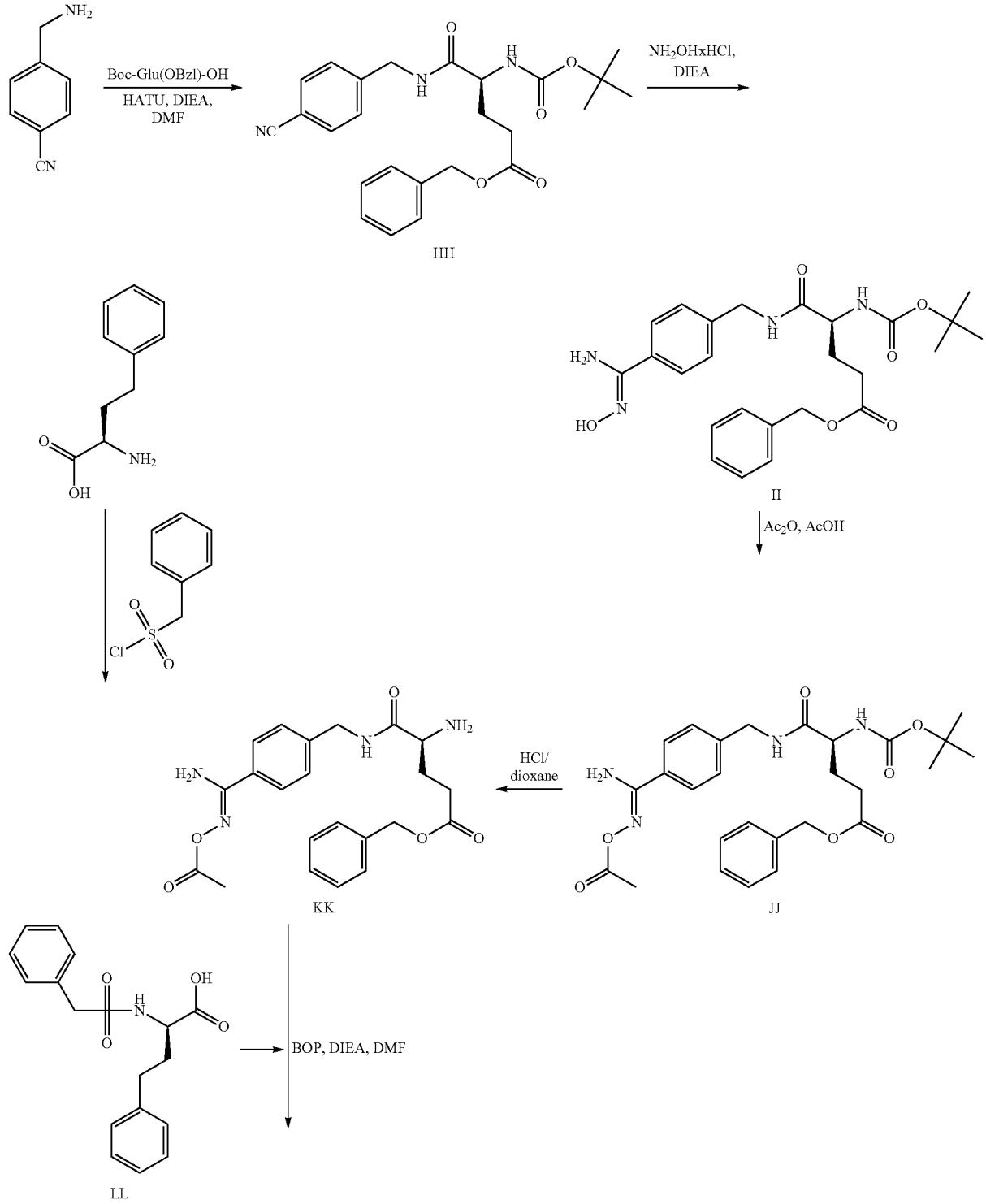

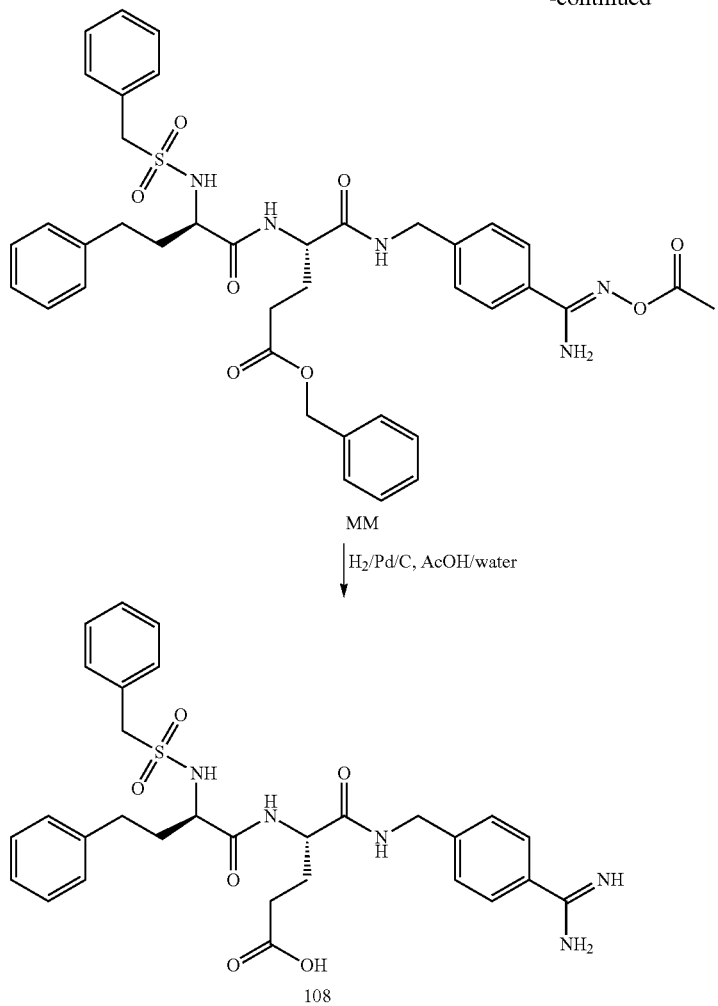

MM

H₂/Pd/C, AcOH/water

108

Preparation 33

Synthesis of (S)-4-tert-butoxycarbonylamino-4-(4-cyano-benzylcarbamoyl)-butyric acid benzyl ester (HH)

A solution of Boc-Glu(OBzl)-OH (7.08 g, 21.0 mmol), BOP (9.72 g, 22.0 mmol) and DIEA (12.18 ml, 70.0 mmol) in DMF (50 ml) was maintained at room temperature for 20 min, followed by the addition of 4-(aminomethyl)benzonitrile hydrochloride (3.38 g, 20.0 mmol). The reaction mixture was stirred at room temperature for an additional 1 h and diluted with EtOAc (500 ml). The obtained solution was extracted with water (100 ml), 5% aq. NaHCO₃ (100 ml) and water (2×100 ml). The organic layer was dried over MgSO₄, evaporated and dried in vacuo to provide compound HH (9.65 g, yield exceeded quantitative) as yellowish oil. LC-MS [M+H] 452.0 ($C_{25}H_{29}N_3O_5$+H, calc: 452.4). Compound HH was used without further purification.

Preparation 34

Synthesis of (S)-4-tert-butoxycarbonylamino-4-[4-(N-hydroxycarbamimidoyl)-benzyl carbamoyl]-butyric acid benzyl ester (II)

A solution of compound HH (9.65 g, 20.0 mmol), hydroxylamine hydrochloride (2.10 g, 30.0 mmol) and DIEA (5.22 ml, 30.0 mmol) in ethanol (abs., 150 ml) was refluxed for 6 h. The reaction mixture was allowed to cool to room temperature and stirred for additional 16 h, then the solvents were evaporated in vacuo. The resultant residue was dried in vacuo to provide compound II (14.8 g, yield exceeded quantitative) as yellowish oil. LC-MS [M+H] 485.5 ($C_{25}H_{32}N_4O_6$+H, calc: 485.8). Compound II was used without further purification.

Preparation 35

Synthesis of (S)-4-tert-butoxycarbonylamino-4-[4-(N-acetylhydroxycarbamimidoyl)-benzyl carbamoyl]-butyric acid benzyl ester (JJ)

A solution of compound II (14.8 g, 20.0 mmol) and acetic anhydride (5.7 ml, 60.0 mmol) in acetic acid (100 ml) was stirred at room temperature for 45 min, and then solvent was evaporated in vacuo. The resultant residue was dissolved in EtOAc (300 ml) and extracted with water (2×75 ml) and brine (75 ml). The organic layer was then dried over MgSO₄, evaporated and dried in vacuo to provide compound JJ (9.58 g, 18.2 mmol) as yellowish solid. LC-MS [M+H] 527.6 ($C_{27}H_{34}N_4O_7$+H, calc: 527.9). Compound JJ was used without further purification.

Preparation 36

Synthesis of (S)-4-[4-(N-acetylhydroxycarbamimidoyl)-benzyl carbamoyl]-butyric acid benzyl ester (KK)

Compound JJ (9.58 g, 18.2 mmol) was dissolved in 1,4-dioxane (50 ml) and treated with 4 N HCl/dioxane (50 ml, 200 mmol) at room temperature for 1 h. Next, the solvent was evaporated in vacuo. The resultant residue was triturated with ether (200 ml). The obtained precipitate was filtrated, washed with ether (100 ml) and hexane (50 ml) and dried in vacuo to provide compound KK (9.64 g, yield exceeded quantitative) as off-white solid. LC-MS [M+H] 426.9 ($C_{22}H_{26}N_4O_5$+H, calc: 427.3). Compound KK was used without further purification.

Preparation 37

Synthesis of (R)-4-phenyl-2-phenylmethanesulfonylamino-butyric acid (LL)

A solution of D-homo-phenylalanine (10.0 g, 55.9 mmol) and NaOH (3.35 g, 83.8 mmol) in a mixture of 1,4-dioxane (80 ml) and water (50 ml) was cooled to ~5° C., followed by alternate addition of α-toluenesulfonyl chloride (16.0 g, 83.8 mmol; 5 portions by 3.2 g) and 1.12 M NaOH (50 ml, 55.9 mmol; 5 portions by 10 ml) maintaining pH>10. The reaction mixture was acidified with 2% aq. $H_2SO_4$ to pH=~2. The obtained solution was extracted with EtOAc (2×200 ml). The organic layer was washed with water (3×75 ml), dried over $MgSO_4$ and then the solvent was evaporated in vacuo. The resultant residue was dried in vacuo to provide compound LL (12.6 g, 37.5 mmol) as white solid. LC-MS [M+H] 334.2 ($C_{17}H_{19}NO_4S$+H, calc: 333.4). Compound LL was used without further purification.

Preparation 38

Synthesis of (S)-4-[4-(N-acetylhydroxycarbamimidoyl)-benzylcarbamoyl]-4-((R)-4-phenyl-2-phenylmethanesulfonylamino-butyrylamino)-butyric acid benzyl ester (MM)

A solution of compound LL (5.9 g, 17.8 mmol), compound KK di-hydrochloride (18.0 mmol), BOP (8.65 g, 19.6 mmol) and DIEA (10.96 ml, 19.6 mmol) in DMF (250 ml) was stirred at room temperature for 2 h. The reaction mixture was diluted with EtOAc (750 ml) and extracted with water (200 ml). The formed precipitate was filtrated, washed with EtOAc (200 ml) and water (200 ml) and dried at room temperature overnight (~18 h) to provide compound MM (8.2 g, 11.0 mmol) as off-white solid. LC-MS [M+H] 743.6 ($C_{39}H_{43}N_5O_8S$+H, calc: 743.9). Compound MM was used without further purification.

Synthesis of (S)-5-(4-carbamimidoylbenzylamino)-5-oxo-4-((R)-4-phenyl-2-(phenylmethylsulfonamido)butanamido)pentanoic acid (Compound 108)

Compound MM (8.0 g, 10.77 mmol) was dissolved in acetic acid (700 ml) followed by the addition of Pd/C (5% wt, 3.0 g) as a suspension in water (50 ml). Reaction mixture was subjected to hydrogenation (Parr apparatus, 5 psi) at room temperature for 3 h. The catalyst was filtered over a pad of Celite on sintered glass filter and washed with methanol. Filtrate was evaporated in vacuo to provide compound 108 as colorless oil. LC-MS [M+H] 594.2 ($C_{30}H_{35}N_5O_6S$+H, calc: 594). Obtained oil was dissolved in water (150 ml) and subjected to HPLC purification. [Nanosyn-Pack YMC-ODS-A (100-10) C-18 column to (75×300 mm); flow rate=250 ml/min; injection volume 150 ml; mobile phase A: 100% water, 0.1% TFA; mobile phase B: 100% acetonitrile, 0.1% TFA; isocratic elution at 10% B in 4 min, gradient elution to 24% B in 18 min, isocratic elution at 24% B in 20 min, gradient elution from 24% B to 58% B in 68 min; detection at 254 nm]. Fractions containing desired compound were combined and concentrated in vacuo. Residue was dissolved in i-PrOH (75 ml) and evaporated in vacuo (procedure was repeated twice) to provide Compound 108 (4.5 g, 70% yield, 98.0% purity) as white solid. LC-MS [M+H] 594.2 ($C_{30}H_{35}N_5O_6S$+H, calc: 594). Retention time*: 3.55 min *—[Chromolith SpeedRod RP-18e C18 column (4.6×50 mm); flow rate 1.5 ml/min; mobile phase A: 0.1% TFA/water; mobile phase B 0.1% TFA/acetonitrile; gradient elution from 5% B to 100% B over 9.6 min, detection 254 nm]

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A pharmaceutical composition, which comprises a trypsin inhibitor and a compound of general formula (I)

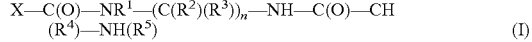

or a pharmaceutically acceptable salt thereof, in which:
X represents a residue of a phenolic opioid, wherein the hydrogen atom of the phenolic hydroxyl group is replaced by a covalent bond to —C(O)—NR¹—(C(R²)(R³))ₙ—NH—C(O)—CH(R⁴)—NH(R⁵);
R¹ represents a (1-4C)alkyl group;
R² and R³ each independently represents a hydrogen atom or a (1-4C)alkyl group;
n represents 2 or 3;
R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and
R⁵ represents a hydrogen atom, an N-acyl group, or a residue of an amino acid, a dipeptide, or an N-acyl derivative of an amino acid or dipeptide.

2. The pharmaceutical composition of claim 1, wherein the phenolic opioid is selected from oxymorphone, hydromorphone and morphine.

3. The pharmaceutical composition of claim 1, wherein the compound of general formula (I) has a general formula (IV):

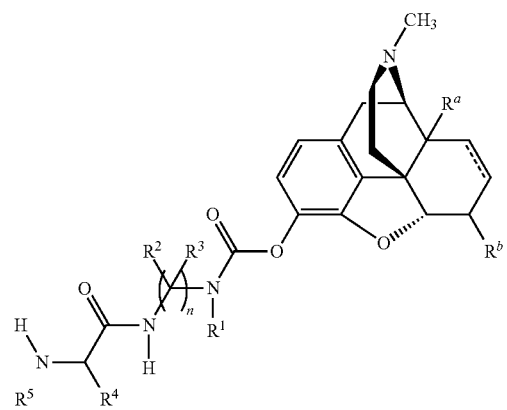

or a pharmaceutically acceptable salt thereof, in which:

$R^a$ is hydrogen or hydroxyl;

$R^b$ is oxo (=O) or hydroxyl;

the dashed line is a double bond or single bond;

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

4. The pharmaceutical composition of claim 1, wherein $R^1$ represents a methyl or ethyl group.

5. The pharmaceutical composition of claim 1, wherein each of $R^2$ and $R^3$ represents a hydrogen atom.

6. The pharmaceutical composition of claim 1, wherein n represents 2.

7. The pharmaceutical composition of claim 1, wherein $R^4$ represents —$CH_2CH_2CH_2NHC(=NH)(NH_2)$.

8. The pharmaceutical composition of claim 1, wherein $R^5$ represents an N-acyl group.

9. The pharmaceutical composition of claim 8, wherein the N-acyl group is an N-(1-4C)alkanoyl, N-benzoyl or N-piperonyl group.

10. The pharmaceutical composition of claim 1, wherein $R^5$ is an acetyl, glycinyl or N-acetylglycinyl group.

11. The pharmaceutical composition of claim 10, wherein $R^5$ is an acetyl group.

12. The pharmaceutical composition of claim 1, wherein the group —C(O)—CH($R^4$)—NH($R^5$) is N-acetylarginine.

13. The pharmaceutical composition of claim 1, wherein X is hydromorphone; $R^1$ is methyl; each of $R^2$ and $R^3$ is a hydrogen atom; n is 2; $R^4$ is —$CH_2CH_2CH_2NHC(=NH)(NH_2)$; and $R^5$ represents an N-acetyl group.

14. The pharmaceutical composition of claim 1, wherein the trypsin inhibitor is derived from soybean.

15. The pharmaceutical composition of claim 1, wherein the trypsin inhibitor is an arginine mimic or a lysine mimic.

16. The pharmaceutical composition of claim 15, wherein the arginine mimic or lysine mimic is a synthetic compound.

17. The pharmaceutical composition of claim 1, wherein the trypsin inhibitor is a compound of formula:

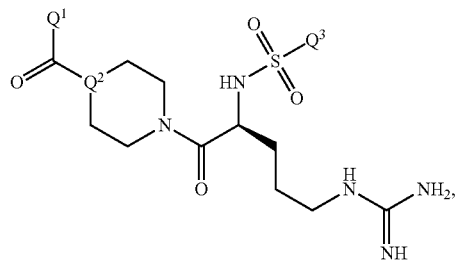

wherein:

$Q^1$ is selected from —O-$Q^4$ or -$Q^4$-COOH, where $Q^4$ is $C_1$-$C_4$ alkyl;

$Q^2$ is N or CH; and $Q^3$ is aryl or substituted aryl.

18. The pharmaceutical composition of claim 1, wherein the trypsin inhibitor is a compound of formula:

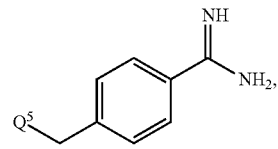

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$; and p is an integer from one to three; and r is an integer from one to three.

19. The pharmaceutical composition of claim 1, wherein the trypsin inhibitor is selected from (S)-ethyl 4-(5-guanidino-2-(naphthalene-2-sulfonamido)pentanoyl)piperazine-1-carboxylate;

(S)-ethyl 4-(5-guanidino-2-(2,4,6-triisopropylphenylsulfonamido)pentanoyl)piperazine-1-carboxylate;

(S)-ethyl 1-(5-guanidino-2-(naphthalene-2-sulfonamido)pentanoyl)piperidine-4-carboxylate;

(S)-ethyl 1-(5-guanidino-2-(2,4,6-triisopropylphenylsulfonamido)pentanoyl)piperidine-4-carboxylate;

(S)-6-(4-(5-guanidino-2-(naphthalene-2-sulfonamido)pentanoyl)piperazin-1-yl)-6-oxohexanoic acid;

4-aminobenzimidamide;

3-(4-carbamimidoylphenyl)-2-oxopropanoic acid;

(S)-5-(4-carbamimidoylbenzylamino)-5-oxo-4(R)-4-phenyl-2-(phenylmethylsulfonamido)butanamido)pentanoic acid;

6-carbamimidoylnaphthalen-2-yl 4-(diaminomethyleneamino)benzoate; and 4,4'-(pentane-1,5-diylbis(oxy))dibenzimidamide.

20. The pharmaceutical composition of claim 1, wherein the compound of general formula (I) comprises hydromorphone 3-(N-methyl-N-(2-N'-acetylarginylamino)) ethylcarbamate or a pharmaceutically acceptable salt thereof.

21. The pharmaceutical composition of claim 1, wherein:

X is oxymorphone;

$R^1$ represents methyl, $R^2$ and $R^3$ each represents a hydrogen atom;

n represents 2;

$R^4$ represents —$CH_2CH_2CH_2NH(C=NH)NH_2$, the configuration of the carbon atom to which $R^4$ is attached corresponding with that in an L-amino acid; and $R^5$ represents N-acetyl.

22. The pharmaceutical composition of claim 1, wherein:

X is morphine;

$R^1$ represents methyl, $R^2$ and $R^3$ each represents a hydrogen atom;

n represents 2;

$R^4$ represents —$CH_2CH_2CH_2NH(C=NH)NH_2$, the configuration of the carbon atom to which $R^4$ is attached corresponding with that in an L-amino acid; and $R^5$ represents N-acetyl.

23. A pharmaceutical composition, which comprises a trypsin inhibitor and a compound of general formula (II):

$$X—C(O)—NR^1—(C(R^2)(R^3))_n—NH—C(O)—CH(R^4)—NH(R^5) \quad (II)$$

or a pharmaceutically acceptable salt thereof, in which:

X represents a residue of a phenolic opioid, wherein the hydrogen atom of the phenolic hydroxyl group is replaced by a covalent bond to —C(O)—$NR^1$—$(C(R^2)(R^3))_n$—NH—C(O)—CH($R^4$)—NH($R^5$);

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl or substituted cycloalkyl group, or two R² or R³ groups on adjacent carbon atoms, together with the carbon atoms to which they are attached, form a cycloalkyl or substituted cycloalkyl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group, a residue of an amino acid, a dipeptide, or an N-acyl derivative of an amino acid or dipeptide.

24. The pharmaceutical composition of claim 23, wherein the compound of general formula (II) has a general formula (V):

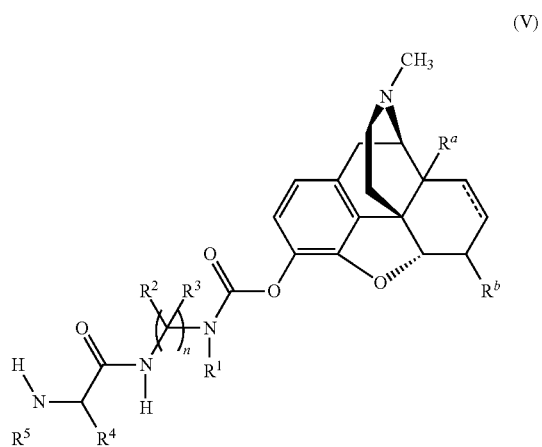

(V)

or a pharmaceutically acceptable salt thereof, in which:

Rᵃ is hydrogen or hydroxyl;

Rᵇ is oxo (=O) or hydroxyl;

the dashed line is a double bond or single bond;

R¹ is selected from alkyl, substituted alkyl, arylalkyl, substituted arylalkyl, aryl and substituted aryl;

each R² is independently selected from hydrogen, alkyl, substituted alkyl, aryl, substituted aryl, acyl, and aminoacyl;

each R³ is independently selected from hydrogen, alkyl, substituted alkyl, aryl, substituted aryl, acyl, and aminoacyl;

or R² and R³ together with the carbon to which they are attached form a cycloalkyl or substituted cycloalkyl group, or two R² or R³ groups on adjacent carbon atoms, together with the carbon atoms to which they are attached, form a cycloalkyl or substituted cycloalkyl group;

n represents an integer from 2 to 4;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group, a residue of an amino acid, a dipeptide, or an N-acyl derivative of an amino acid or dipeptide.

25. The pharmaceutical composition of claim 23, wherein the compound of general formula (II) has a general formula (III):

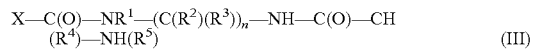

(III)

or a pharmaceutically acceptable salt thereof, in which:

X represents a residue of a phenolic opioid, wherein the hydrogen atom of the phenolic hydroxyl group is replaced by a covalent bond to —C(O)—NR¹—(C(R²)(R³))ₙ—NH—C(O)—CH(R⁴)—NH(R⁵);

R¹ represents a (1-4C)alkyl group;

R² and R³ each independently represents a hydrogen atom or a (1-4C)alkyl group;

n represents 2 or 3;

R⁴ represents —CH₂CH₂CH₂NH(C=NH)NH₂ or —CH₂CH₂CH₂CH₂NH₂, the configuration of the carbon atom to which R⁴ is attached corresponding with that in an L-amino acid; and R⁵ represents a hydrogen atom, an N-acyl group, a residue of an amino acid, a dipeptide, or an N-acyl derivative of an amino acid or dipeptide.

26. The pharmaceutical composition of claim 23, wherein acyl is substituted acyl.

27. The pharmaceutical composition of claim 23, wherein n is 2.

28. The pharmaceutical composition of claim 23, wherein R¹ is methyl or ethyl.

29. The pharmaceutical composition of claim 23, wherein R⁵ is acetyl, benzoyl, malonyl, piperonyl, succinyl, N-acetylarginine or N-acetyllysine.

30. The pharmaceutical composition of claim 23, wherein R² and R³ are hydrogen.

31. The pharmaceutical composition of claim 23, wherein R² and R³ which are on the same carbon are alkyl.

32. The pharmaceutical composition of claim 23, wherein R² and R³ which are on the same carbon form a spirocycle.

33. The pharmaceutical composition of claim 23, wherein R² and R³ which are on the same carbon are methyl.

34. The pharmaceutical composition of claim 23, wherein R² and R³ can modulate a rate of intramolecular cyclization.

35. The pharmaceutical composition of claim 23, wherein R² and R³ comprise an electron-withdrawing group or an electron-donating group.

36. The pharmaceutical composition of claim 23, wherein —[C(R²)(R³)]ₙ— is selected from —CH(CH₂F)CH(CH₂F)—; —CH(CHF₂)CH(CHF₂)—; —CH(CF₃)CH(CF₃)—; —CH₂CH(CF₃)—; —CH₂CH(CHF₂)—; —CH₂CH(CH₂F)—; —CH₂CH(F)CH₂—; —CH₂C(F₂)CH₂—; —CH₂CH(C(O)NR²⁰R²¹)—; —CH₂CH(C(O)OR²²)—; —CH₂CH(C(O)OH)—; —CH(CH₂F)CH₂CH(CH₂F)—; —CH(CHF₂)CH₂CH(CHF₂)—; —CH(CF₃)CH₂CH(CF₃)—; —CH₂CH₂CH(CF₃)—; —CH₂CH₂CH(CHF₂)—; —CH₂CH₂CH(CH₂F)—; —CH₂CH₂CH(C(O)NR²³R²⁴)—; —CH₂CH₂CH(C(O)OR²⁵)—; and —CH₂CH₂CH(C(O)OH)—, in which R²⁰, R²¹, R²² and R²³ each independently represents hydrogen or (1-6C)alkyl, and R²⁴ and R²⁵ each independently represents (1-6C)alkyl.

37. The pharmaceutical composition of claim 23, wherein one of R² and R³ is aminoacyl.

38. The pharmaceutical composition of claim 23, wherein one of R² and R³ is

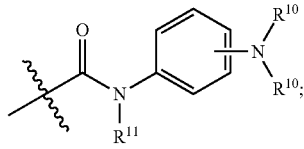

wherein each R¹⁰ is independently selected from hydrogen, alkyl, substituted alkyl, and acyl, and R¹¹ is alkyl or substituted alkyl.

39. The pharmaceutical composition of claim 23, wherein one of $R^2$ and $R^3$ is

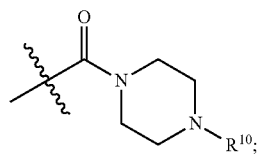

wherein $R^{10}$ is selected from hydrogen, alkyl, substituted alkyl, and acyl.

40. The pharmaceutical composition claim 39, wherein $R^{10}$ is acyl.

41. The pharmaceutical composition of claim 23, wherein the trypsin inhibitor is derived from soybean.

42. The pharmaceutical composition of claim 23, wherein the trypsin inhibitor is an arginine mimic or a lysine mimic.

43. The pharmaceutical composition of claim 42, wherein the arginine mimic or lysine mimic is a synthetic compound.

44. The pharmaceutical composition of claim 23, wherein the trypsin inhibitor is a compound of formula:

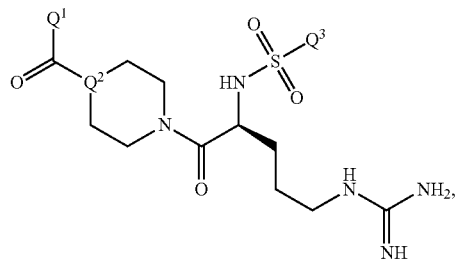

wherein:
$Q^1$ is selected from —O-$Q^4$ or -$Q^4$—COOH, where $Q^4$ is $C_1$-$C_4$ alkyl;
$Q^2$ is N or CH; and
$Q^3$ is aryl or substituted aryl.

45. The pharmaceutical composition of claim 23, wherein the trypsin inhibitor is a compound of formula:

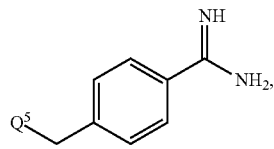

wherein:
$Q^5$ is —C(O)—COOH or —NH-$Q^6$-$Q^7$-$SO_2$—$C_6H_5$, where $Q^6$ is —$(CH_2)_p$—COOH;
$Q^7$ is —$(CH_2)_r$—$C_6H_5$; and
p is an integer from one to three; and
r is an integer from one to three.

46. The pharmaceutical composition of claim 23, wherein the trypsin inhibitor is selected from
(S)-ethyl 4-(5-guanidino-2-(naphthalene-2-sulfonamido) pentanoyl)piperazine-1-carboxylate;
(S)-ethyl 4-(5-guanidino-2-(2,4,6-triisopropylphenylsulfonamido)pentanoyl)piperazine-1-carboxylate;
(S)-ethyl 1-(5-guanidino-2-(naphthalene-2-sulfonamido) pentanoyl)piperidine-4-carboxylate;
(S)-ethyl 1-(5-guanidino-2-(2,4,6-triisopropylphenylsulfonamido)pentanoyl)piperidine-4-carboxylate;
(S)-6-(4-(5-guanidino-2-(naphthalene-2-sulfonamido) pentanoyl)piperazin-1-yl)-6-oxohexanoic acid;
4-aminobenzimidamide;
3-(4-carbamimidoylphenyl)-2-oxopropanoic acid;
(S)-5-(4-carbamimidoylbenzylamino)-5-oxo-4-(R)-4-phenyl-2-(phenylmethylsulfonamido)butanamido)pentanoic acid;
6-carbamimidoylnaphthalen-2-yl 4-(diaminomethyleneamino)benzoate; and
4,4'-(pentane-1,5-diylbis(oxy))dibenzimidamide.

47. The pharmaceutical composition of claim 25, wherein the compound of general formula (III) has a general formula (VI):

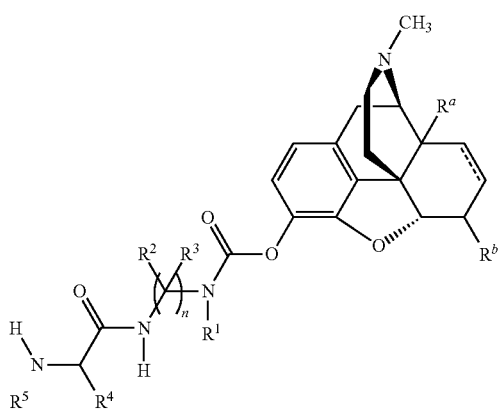

or a pharmaceutically acceptable salt thereof, in which:
$R^a$ is hydrogen or hydroxyl;
$R^b$ is oxo (=O) or hydroxyl;
the dashed line is a double bond or single bond;
$R^1$ represents a (1-4C)alkyl group;
$R^2$ and $R^3$ each independently represents a hydrogen atom or a (1-4C)alkyl group;
n represents 2 or 3;
$R^4$ represents —$CH_2CH_2CH_2NH(C=NH)NH_2$ or —$CH_2CH_2CH_2CH_2NH_2$, the configuration of the carbon atom to which $R^4$ is attached corresponding with that in an L-amino acid; and
$R^5$ represents a hydrogen atom, an N-acyl group, a residue of an amino acid, a dipeptide, or an N-acyl derivative of an amino acid or dipeptide.

48. The pharmaceutical composition of claim 25, wherein acyl is substituted acyl.

49. The pharmaceutical composition of claim 25, wherein $R^5$ is acetyl, benzoyl, malonyl, piperonyl, succinyl, N-acetylarginine or N-acetyllysine.

50. A pharmaceutical composition comprising:
a phenolic opioid prodrug comprising a trypsin-labile moiety that provides enzymatically-controlled release of a phenolic opioid, and
a trypsin inhibitor that mediates the enzymatically-controlled release of the phenolic opioid from the prodrug so as to attenuate enzymatic cleavage of the prodrug.

51. A method of treating or preventing pain in a patient in need thereof, which comprises administering to the patient an effective amount of a pharmaceutical composition of claim 1.

52. A method for reducing drug abuse potential of a composition containing a phenolic opioid prodrug, the method comprising:
combining a phenolic opioid prodrug comprising a trypsin-labile moiety that provides enzymatically-controlled release of a phenolic opioid with a trypsin inhibitor that interacts with the enzyme(s) that mediates the enzymatically-controlled release of the phenolic opioid from the prodrug, wherein the trypsin inhibitor reduces the ability of a user to release a phenolic opioid from the phenolic opioid prodrug by addition of the enzyme.

53. The method of claim 52, wherein the phenolic opioid prodrug is a compound of formulae I-VI and the enzyme inhibitor is a trypsin inhibitor.

54. A method of treating or preventing pain in a patient in need thereof, which comprises administering to the patient an effective amount of a pharmaceutical composition of claim 23.

* * * * *